(12) United States Patent
Thommen et al.

(10) Patent No.: US 10,940,016 B2
(45) Date of Patent: Mar. 9, 2021

(54) EXPANDABLE INTERVERTEBRAL FUSION CAGE

(71) Applicant: Medos International Sarl, Le Locle (CH)

(72) Inventors: Daniel Thommen, Oberdorf (CH); Joern Richter, Kandern (DE); Thomas M. DiMauro, Southboro, MA (US)

(73) Assignee: Medos International Sarl, Le Locle (CH)

( * ) Notice: Subject to any disclaimer, the term of this patent is extended or adjusted under 35 U.S.C. 154(b) by 0 days.

(21) Appl. No.: 15/642,044

(22) Filed: Jul. 5, 2017

(65) Prior Publication Data

US 2019/0008654 A1    Jan. 10, 2019

(51) Int. Cl.
*A61F 2/44* (2006.01)
*A61F 2/46* (2006.01)
*A61F 2/30* (2006.01)

(52) U.S. Cl.
CPC .......... *A61F 2/4465* (2013.01); *A61F 2/4455* (2013.01); *A61F 2/4611* (2013.01); *A61F 2002/308* (2013.01); *A61F 2002/30014* (2013.01); *A61F 2002/3055* (2013.01); *A61F 2002/3082* (2013.01); *A61F 2002/30115* (2013.01); *A61F 2002/30116* (2013.01); *A61F 2002/30462* (2013.01); *A61F 2002/30471* (2013.01); *A61F 2002/30545* (2013.01); *A61F 2002/30556* (2013.01); *A61F 2002/30565* (2013.01); *A61F 2002/30579* (2013.01); *A61F 2002/30733* (2013.01); *A61F 2002/30802* (2013.01); *A61F 2002/30841* (2013.01); *A61F 2002/443* (2013.01); *A61F 2002/4415* (2013.01); *A61F 2002/4687* (2013.01)

(58) Field of Classification Search
CPC ........ A61F 2/4465; A61F 2/446; A61F 2/447; A61F 2/4455; A62F 2002/4415
See application file for complete search history.

(56) References Cited

U.S. PATENT DOCUMENTS

| 1,636,636 A | 7/1927 | Humble |
| 1,677,337 A | 7/1928 | Grove |
| 1,802,560 A | 4/1931 | Kerwin |

(Continued)

FOREIGN PATENT DOCUMENTS

| AU | 2005314079 B2 | 7/2012 |
| CA | 2617872 A1 | 2/2007 |

(Continued)

OTHER PUBLICATIONS

Vandorpe, et al in the Handbook of Biodegradable Polymers. edited by Domb, et al, Hardwood Academic Press, pp. 161-182 (1997).

(Continued)

*Primary Examiner* — Amy R Sipp
(74) *Attorney, Agent, or Firm* — BakerHostetler

(57) ABSTRACT

An expandable intervertebral fusion cage is independently expandable vertically and laterally. The fusion cage includes a cage body that can receive an expansion member that causes the fusion cage to expand vertically. The cage body is responsive to a compressive force to move to an expanded lateral position, whereby the fusion cage defines a substantially circular annular profile.

23 Claims, 20 Drawing Sheets

(56) References Cited

U.S. PATENT DOCUMENTS

| | | |
|---|---|---|
| 1,924,695 A | 8/1933 | Olson |
| 1,965,653 A | 7/1934 | Kennedy |
| 2,077,804 A | 4/1937 | Morrison |
| 2,115,250 A | 4/1938 | Bruson |
| 2,121,193 A | 6/1938 | Hanicke |
| 2,170,111 A | 8/1939 | Bruson |
| 2,173,655 A | 9/1939 | Neracher et al. |
| 2,229,024 A | 1/1941 | Bruson |
| 2,243,717 A | 5/1941 | Moreira |
| 2,304,703 A | 12/1942 | O'Leary |
| 2,381,050 A | 8/1945 | Hardinge |
| 2,388,056 A | 10/1945 | Hendricks |
| 2,485,531 A | 10/1949 | William et al. |
| 2,489,870 A | 11/1949 | Dzus |
| 2,490,364 A | 12/1949 | Livingston |
| 2,541,972 A | 2/1951 | Wallace |
| 2,570,465 A | 10/1951 | Lundholm |
| 2,580,782 A | 1/1952 | Hoffmann et al. |
| 2,677,369 A | 5/1954 | Knowles |
| 2,706,701 A | 4/1955 | Hans et al. |
| 2,710,277 A | 6/1955 | Shelanski et al. |
| 2,746,385 A | 5/1956 | Muller |
| 2,826,532 A | 3/1958 | Hosmer |
| 2,900,305 A | 8/1959 | Siggia |
| 2,977,315 A | 3/1961 | Scheib et al. |
| 3,091,237 A | 5/1963 | Skinner |
| 3,112,743 A | 12/1963 | Cochran et al. |
| 3,115,804 A | 12/1963 | Johnson |
| 3,228,828 A | 1/1966 | Romano |
| 3,312,139 A | 4/1967 | Di Cristina |
| 3,486,505 A | 12/1969 | Morrison |
| 3,489,143 A | 1/1970 | Halloran |
| 3,648,294 A | 3/1972 | Shahrestani |
| 3,698,391 A | 10/1972 | Mahony |
| 3,717,655 A | 2/1973 | Godefroi et al. |
| 3,760,802 A | 9/1973 | Fischer et al. |
| 3,800,788 A | 4/1974 | White |
| 3,805,775 A | 4/1974 | Fischer et al. |
| 3,811,449 A | 5/1974 | Gravlee et al. |
| 3,842,825 A | 10/1974 | Wagner |
| 3,848,601 A | 11/1974 | Ma et al. |
| 3,855,638 A | 12/1974 | Pilliar |
| 3,867,728 A | 2/1975 | Stubstad et al. |
| 3,875,595 A | 4/1975 | Froning |
| 3,889,665 A | 6/1975 | Ling et al. |
| 3,964,480 A | 6/1976 | Froning |
| 3,986,504 A | 10/1976 | Avila |
| 4,013,071 A | 3/1977 | Rosenberg |
| 4,052,988 A | 10/1977 | Doddi et al. |
| 4,053,988 A | 10/1977 | Budic |
| 4,091,806 A | 5/1978 | Aginsky |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,175,555 A | 11/1979 | Herbert |
| 4,205,399 A | 6/1980 | Jamiolkowski et al. |
| 4,208,511 A | 6/1980 | Jamiolkowski et al. |
| 4,236,512 A | 12/1980 | Aginsky |
| 4,249,435 A | 2/1981 | Smith et al. |
| 4,262,665 A | 4/1981 | Roalstad et al. |
| 4,262,676 A | 4/1981 | Jamshidi |
| 4,274,163 A | 6/1981 | Malcom et al. |
| 4,275,717 A | 6/1981 | Bolesky |
| 4,312,337 A | 1/1982 | Donohue |
| 4,312,353 A | 1/1982 | Shahbabian |
| 4,313,434 A | 2/1982 | Segal |
| 4,341,206 A | 7/1982 | Perrett et al. |
| 4,349,921 A | 9/1982 | Kuntz |
| 4,350,151 A | 9/1982 | Scott |
| 4,351,069 A | 9/1982 | Ballintyn et al. |
| 4,352,883 A | 10/1982 | Lim |
| 4,369,790 A | 1/1983 | McCarthy |
| 4,399,814 A | 8/1983 | Pratt et al. |
| 4,401,112 A | 8/1983 | Rezaian |
| 4,401,433 A | 8/1983 | Luther |
| 4,409,974 A | 10/1983 | Freedland |
| 4,440,921 A | 4/1984 | Allcock et al. |
| 4,449,532 A | 5/1984 | Storz |
| 4,451,256 A | 5/1984 | Weikl et al. |
| 4,456,005 A | 6/1984 | Lichty |
| 4,462,394 A | 7/1984 | Jacobs |
| 4,463,753 A | 8/1984 | Gustilo |
| 4,466,435 A | 8/1984 | Murray |
| 4,467,479 A | 8/1984 | Brody |
| 4,488,543 A | 12/1984 | Tornier |
| 4,488,549 A | 12/1984 | Lee et al. |
| 4,494,535 A | 1/1985 | Haig |
| 4,495,174 A | 1/1985 | Allcock et al. |
| 4,532,660 A | 8/1985 | Field |
| 4,537,185 A | 8/1985 | Stednitz |
| 4,542,539 A | 9/1985 | Rowe et al. |
| 4,545,374 A | 10/1985 | Jacobson |
| 4,562,598 A | 1/1986 | Kranz |
| 4,573,448 A | 3/1986 | Kambin |
| 4,595,006 A | 6/1986 | Burke et al. |
| 4,601,710 A | 7/1986 | Moll |
| 4,625,722 A | 12/1986 | Murray |
| 4,625,725 A | 12/1986 | Davison et al. |
| 4,627,434 A | 12/1986 | Murray |
| 4,628,945 A | 12/1986 | Johnson, Jr. |
| 4,629,450 A | 12/1986 | Suzuki et al. |
| 4,630,616 A | 12/1986 | Tretinyak |
| 4,632,101 A | 12/1986 | Freedland |
| 4,640,271 A | 2/1987 | Lower |
| 4,641,640 A | 2/1987 | Griggs |
| 4,645,503 A | 2/1987 | Lin et al. |
| 4,651,717 A | 3/1987 | Jakubczak |
| 4,653,489 A | 3/1987 | Tronzo |
| 4,665,906 A | 5/1987 | Jervis |
| 4,667,663 A | 5/1987 | Miyata |
| 4,686,973 A | 8/1987 | Frisch |
| 4,686,984 A | 8/1987 | Bonnet |
| 4,688,561 A | 8/1987 | Reese |
| 4,697,584 A | 10/1987 | Haynes |
| 4,701,993 A | 10/1987 | Bradley et al. |
| 4,706,670 A | 11/1987 | Andersen et al. |
| 4,714,469 A | 12/1987 | Kenna |
| 4,714,478 A | 12/1987 | Fischer |
| 4,721,103 A | 1/1988 | Freedland |
| 4,723,544 A | 2/1988 | Moore et al. |
| 4,743,256 A | 5/1988 | Brantigan |
| 4,743,257 A | 5/1988 | Toermaelae et al. |
| 4,759,766 A | 7/1988 | Buettner-Janz et al. |
| 4,760,843 A | 8/1988 | Fischer et al. |
| 4,772,287 A | 9/1988 | Ray et al. |
| 4,790,304 A | 12/1988 | Rosenberg |
| 4,790,817 A | 12/1988 | Luther |
| 4,796,612 A | 1/1989 | Reese |
| 4,802,479 A | 2/1989 | Haber et al. |
| 4,815,909 A | 3/1989 | Simons |
| 4,827,917 A | 5/1989 | Brumfield |
| 4,834,069 A | 5/1989 | Umeda |
| 4,838,282 A | 6/1989 | Strasser et al. |
| 4,856,950 A | 8/1989 | Bushnell |
| 4,858,601 A | 8/1989 | Glisson |
| 4,862,891 A | 9/1989 | Smith |
| 4,863,476 A | 9/1989 | Shepperd |
| 4,870,153 A | 9/1989 | Matzner et al. |
| 4,871,366 A | 10/1989 | Von et al. |
| 4,873,976 A | 10/1989 | Schreiber |
| 4,878,915 A | 11/1989 | Brantigan |
| 4,880,622 A | 11/1989 | Allcock et al. |
| 4,888,022 A | 12/1989 | Huebsch |
| 4,888,024 A | 12/1989 | Powlan |
| 4,892,550 A | 1/1990 | Huebsch |
| 4,896,662 A | 1/1990 | Noble |
| 4,898,186 A | 2/1990 | Ikada et al. |
| 4,898,577 A | 2/1990 | Badger et al. |
| 4,903,692 A | 2/1990 | Reese |
| 4,904,261 A | 2/1990 | Dove et al. |
| 4,911,718 A | 3/1990 | Lee et al. |
| 4,917,554 A | 4/1990 | Bronn |
| 4,932,969 A | 6/1990 | Frey et al. |

(56) References Cited

U.S. PATENT DOCUMENTS

| | | |
|---|---|---|
| 4,940,467 A | 7/1990 | Tronzo |
| 4,941,466 A | 7/1990 | Romano |
| 4,946,378 A | 8/1990 | Hirayama et al. |
| 4,955,908 A | 9/1990 | Frey et al. |
| 4,959,064 A | 9/1990 | Engelhardt |
| 4,961,740 A | 10/1990 | Ray et al. |
| 4,963,144 A | 10/1990 | Huene |
| 4,966,587 A | 10/1990 | Baumgart |
| 4,968,317 A | 11/1990 | Toermaelae et al. |
| 4,969,888 A | 11/1990 | Scholten et al. |
| 4,978,334 A | 12/1990 | Toye et al. |
| 4,978,349 A | 12/1990 | Frigg |
| 4,981,482 A | 1/1991 | Ichikawa |
| 4,988,351 A | 1/1991 | Paulos et al. |
| 4,994,027 A | 2/1991 | Farrell |
| 5,002,557 A | 3/1991 | Hasson |
| 5,011,484 A | 4/1991 | Breard |
| 5,013,315 A | 5/1991 | Barrows |
| 5,013,316 A | 5/1991 | Goble et al. |
| 5,015,247 A | 5/1991 | Michelson |
| 5,015,255 A | 5/1991 | Kuslich |
| 5,030,233 A | 7/1991 | Ducheyne |
| 5,041,113 A | 8/1991 | Biedermann et al. |
| 5,051,189 A | 9/1991 | Farrah |
| 5,053,035 A | 10/1991 | McLaren |
| 5,055,104 A | 10/1991 | Ray |
| 5,059,193 A | 10/1991 | Kuslich |
| 5,062,849 A | 11/1991 | Schelhas |
| 5,071,435 A | 12/1991 | Fuchs et al. |
| 5,071,437 A | 12/1991 | Steffee |
| 5,080,662 A | 1/1992 | Paul |
| 5,084,043 A | 1/1992 | Hertzmann et al. |
| 5,092,891 A | 3/1992 | Kummer et al. |
| 5,098,241 A | 3/1992 | Aldridge et al. |
| 5,098,433 A | 3/1992 | Freedland |
| 5,098,435 A | 3/1992 | Stednitz et al. |
| 5,102,413 A | 4/1992 | Poddar |
| 5,108,404 A | 4/1992 | Scholten et al. |
| 5,114,407 A | 5/1992 | Burbank |
| 5,116,336 A | 5/1992 | Frigg |
| 5,120,171 A | 6/1992 | Lasner |
| 5,122,130 A | 6/1992 | Keller |
| 5,122,133 A | 6/1992 | Evans |
| 5,122,141 A | 6/1992 | Simpson et al. |
| 5,123,926 A | 6/1992 | Pisharodi |
| 5,133,755 A | 7/1992 | Brekke |
| 5,134,477 A | 7/1992 | Knauer et al. |
| 5,139,486 A | 8/1992 | Moss |
| 5,147,361 A | 9/1992 | Ojima et al. |
| 5,147,366 A | 9/1992 | Arroyo et al. |
| 5,158,543 A | 10/1992 | Lazarus |
| 5,163,989 A | 11/1992 | Campbell et al. |
| 5,167,663 A | 12/1992 | Brumfield |
| 5,167,664 A | 12/1992 | Hodorek |
| 5,167,665 A | 12/1992 | McKinney |
| 5,169,400 A | 12/1992 | Muehling et al. |
| 5,171,278 A | 12/1992 | Pisharodi |
| 5,171,279 A | 12/1992 | Mathews |
| 5,171,280 A | 12/1992 | Baumgartner |
| 5,176,651 A | 1/1993 | Allgood et al. |
| 5,176,683 A | 1/1993 | Kimsey et al. |
| 5,176,692 A | 1/1993 | Wilk et al. |
| 5,176,697 A | 1/1993 | Hasson et al. |
| 5,178,501 A | 1/1993 | Carstairs |
| 5,183,052 A | 2/1993 | Terwilliger |
| 5,183,464 A | 2/1993 | Dubrul et al. |
| 5,188,118 A | 2/1993 | Terwilliger |
| 5,192,327 A | 3/1993 | Brantigan |
| 5,195,506 A | 3/1993 | Hulfish |
| 5,201,742 A | 4/1993 | Hasson |
| 5,209,751 A | 5/1993 | Farris et al. |
| 5,217,462 A | 6/1993 | Asnis et al. |
| 5,217,486 A | 6/1993 | Rice et al. |
| 5,224,952 A | 7/1993 | Deniega et al. |
| 5,228,441 A | 7/1993 | Lundquist |
| 5,234,431 A | 8/1993 | Keller |
| 5,241,972 A | 9/1993 | Bonati |
| 5,242,410 A | 9/1993 | Melker |
| 5,242,447 A | 9/1993 | Borzone |
| 5,242,448 A | 9/1993 | Pettine et al. |
| 5,242,879 A | 9/1993 | Abe et al. |
| 5,246,441 A | 9/1993 | Ross et al. |
| 5,250,049 A | 10/1993 | Michael |
| 5,257,632 A | 11/1993 | Turkel et al. |
| 5,263,953 A | 11/1993 | Bagby |
| 5,269,797 A | 12/1993 | Bonati et al. |
| 5,280,782 A | 1/1994 | Wilk |
| 5,285,795 A | 2/1994 | Ryan et al. |
| 5,286,001 A | 2/1994 | Rafeld |
| 5,290,243 A | 3/1994 | Chodorow et al. |
| 5,290,312 A | 3/1994 | Kojimoto et al. |
| 5,300,074 A | 4/1994 | Frigg |
| 5,303,718 A | 4/1994 | Krajicek |
| 5,304,142 A | 4/1994 | Liebl et al. |
| 5,306,307 A | 4/1994 | Senter et al. |
| 5,306,308 A | 4/1994 | Gross et al. |
| 5,306,309 A | 4/1994 | Wagner et al. |
| 5,306,310 A | 4/1994 | Siebels |
| 5,308,327 A | 5/1994 | Heaven et al. |
| 5,308,352 A | 5/1994 | Koutrouvelis |
| 5,312,410 A | 5/1994 | Miller et al. |
| 5,312,417 A | 5/1994 | Wilk |
| 5,314,477 A | 5/1994 | Marnay |
| 5,322,505 A | 6/1994 | Krause et al. |
| 5,324,261 A | 6/1994 | Amundson et al. |
| 5,330,429 A | 7/1994 | Noguchi et al. |
| 5,331,975 A | 7/1994 | Bonutti |
| 5,334,184 A | 8/1994 | Bimman |
| 5,334,204 A | 8/1994 | Clewett et al. |
| 5,342,365 A | 8/1994 | Waldman |
| 5,342,382 A | 8/1994 | Brinkerhoff et al. |
| 5,344,252 A | 9/1994 | Kakimoto |
| 5,352,231 A | 10/1994 | Brumfield et al. |
| 5,354,298 A | 10/1994 | Lee et al. |
| 5,361,752 A | 11/1994 | Moll et al. |
| 5,364,398 A | 11/1994 | Chapman et al. |
| 5,370,646 A | 12/1994 | Reese et al. |
| 5,370,647 A | 12/1994 | Graber et al. |
| 5,370,661 A | 12/1994 | Branch |
| 5,370,697 A | 12/1994 | Baumgartner |
| 5,372,660 A | 12/1994 | Davidson et al. |
| 5,374,267 A | 12/1994 | Siegal |
| 5,382,248 A | 1/1995 | Jacobson et al. |
| 5,383,932 A | 1/1995 | Wilson et al. |
| 5,385,151 A | 1/1995 | Scarfone et al. |
| 5,387,213 A | 2/1995 | Breard et al. |
| 5,387,215 A | 2/1995 | Fisher |
| 5,390,683 A | 2/1995 | Pisharodi |
| 5,391,170 A | 2/1995 | McGuire et al. |
| 5,395,317 A | 3/1995 | Kambin |
| 5,395,371 A | 3/1995 | Miller et al. |
| 5,395,372 A | 3/1995 | Holt et al. |
| 5,397,364 A | 3/1995 | Kozak et al. |
| 5,401,269 A | 3/1995 | Buettner-Janz et al. |
| 5,407,430 A | 4/1995 | Peters |
| 5,410,016 A | 4/1995 | Hubbell et al. |
| 5,415,661 A | 5/1995 | Holmes |
| 5,423,816 A | 6/1995 | Lin |
| 5,423,817 A | 6/1995 | Lin |
| 5,423,850 A | 6/1995 | Berger |
| 5,424,773 A | 6/1995 | Saito |
| 5,425,773 A | 6/1995 | Boyd et al. |
| 5,431,658 A | 7/1995 | Moskovich |
| 5,441,538 A | 8/1995 | Bonutti |
| 5,443,514 A | 8/1995 | Steffee |
| 5,443,515 A | 8/1995 | Cohen et al. |
| 5,449,359 A | 9/1995 | Groiso |
| 5,449,361 A | 9/1995 | Preissman |
| 5,452,748 A | 9/1995 | Simmons et al. |
| 5,454,365 A | 10/1995 | Bonutti |
| 5,454,790 A | 10/1995 | Dubrul |
| 5,454,827 A | 10/1995 | Aust et al. |
| 5,456,686 A | 10/1995 | Klapper et al. |
| 5,458,641 A | 10/1995 | Ramirez Jimenez |

(56) References Cited

U.S. PATENT DOCUMENTS

| | | |
|---|---|---|
| 5,458,643 A | 10/1995 | Oka et al. |
| 5,462,563 A | 10/1995 | Shearer et al. |
| 5,464,407 A | 11/1995 | McGuire |
| 5,464,427 A | 11/1995 | Curtis et al. |
| 5,464,929 A | 11/1995 | Bezwada et al. |
| 5,468,245 A | 11/1995 | Vargas, III |
| 5,470,333 A | 11/1995 | Ray |
| 5,472,426 A | 12/1995 | Bonati et al. |
| 5,474,539 A | 12/1995 | Costa et al. |
| 5,480,400 A | 1/1996 | Berger |
| 5,484,437 A | 1/1996 | Michelson |
| 5,486,190 A | 1/1996 | Green |
| 5,496,318 A | 3/1996 | Howland et al. |
| 5,498,265 A | 3/1996 | Asnis et al. |
| 5,499,986 A | 3/1996 | Dimarco |
| 5,501,695 A | 3/1996 | Anspach et al. |
| 5,505,710 A | 4/1996 | Dorsey, III |
| 5,507,816 A | 4/1996 | Bullivant |
| 5,509,923 A | 4/1996 | Middleman et al. |
| 5,512,037 A | 4/1996 | Russell et al. |
| 5,514,143 A | 5/1996 | Bonutti et al. |
| 5,514,153 A | 5/1996 | Bonutti |
| 5,514,180 A | 5/1996 | Heggeness et al. |
| 5,520,690 A | 5/1996 | Errico et al. |
| 5,520,896 A | 5/1996 | De et al. |
| 5,522,398 A | 6/1996 | Goldenberg et al. |
| 5,522,790 A | 6/1996 | Moll et al. |
| 5,522,846 A | 6/1996 | Bonutti |
| 5,522,895 A | 6/1996 | Mikos |
| 5,522,899 A | 6/1996 | Michelson |
| 5,527,312 A | 6/1996 | Ray |
| 5,527,343 A | 6/1996 | Bonutti |
| 5,527,624 A | 6/1996 | Higgins et al. |
| 5,529,580 A | 6/1996 | Kusunoki et al. |
| 5,531,856 A | 7/1996 | Moll et al. |
| 5,534,023 A | 7/1996 | Henley |
| 5,534,029 A | 7/1996 | Shima |
| 5,534,030 A | 7/1996 | Navarro et al. |
| 5,534,031 A | 7/1996 | Matsuzaki et al. |
| 5,536,127 A | 7/1996 | Pennig |
| 5,538,009 A | 7/1996 | Byrne et al. |
| 5,540,688 A | 7/1996 | Navas |
| 5,540,693 A | 7/1996 | Fisher |
| 5,540,711 A | 7/1996 | Kieturakis et al. |
| 5,545,164 A | 8/1996 | Howland |
| 5,545,222 A | 8/1996 | Bonutti |
| 5,549,610 A | 8/1996 | Russell et al. |
| 5,549,679 A | 8/1996 | Kuslich |
| 5,554,191 A | 9/1996 | Lahille et al. |
| 5,556,431 A | 9/1996 | Buettner-Janz |
| 5,558,674 A | 9/1996 | Heggeness et al. |
| D374,287 S | 10/1996 | Goble et al. |
| 5,562,736 A | 10/1996 | Ray et al. |
| 5,562,738 A | 10/1996 | Boyd et al. |
| 5,564,926 A | 10/1996 | Braanemark |
| 5,569,248 A | 10/1996 | Mathews |
| 5,569,251 A | 10/1996 | Baker et al. |
| 5,569,290 A | 10/1996 | McAfee |
| 5,569,548 A | 10/1996 | Koike et al. |
| 5,571,109 A | 11/1996 | Bertagnoli |
| 5,571,189 A | 11/1996 | Kuslich |
| 5,571,190 A | 11/1996 | Ulrich et al. |
| 5,575,790 A | 11/1996 | Chen et al. |
| 5,578,034 A | 11/1996 | Estes |
| 5,591,166 A | 1/1997 | Bernhardt et al. |
| 5,591,168 A | 1/1997 | Judet et al. |
| 5,593,409 A | 1/1997 | Michelson |
| 5,595,751 A | 1/1997 | Bezwada et al. |
| 5,597,579 A | 1/1997 | Bezwada et al. |
| 5,601,553 A | 2/1997 | Trebing et al. |
| 5,601,556 A | 2/1997 | Pisharodi |
| 5,601,572 A | 2/1997 | Middleman et al. |
| 5,607,687 A | 3/1997 | Bezwada et al. |
| 5,609,634 A | 3/1997 | Voydeville |
| 5,609,635 A | 3/1997 | Michelson |
| 5,609,636 A | 3/1997 | Kohrs et al. |
| 5,613,950 A | 3/1997 | Yoon |
| 5,618,142 A | 4/1997 | Sonden et al. |
| 5,618,314 A | 4/1997 | Harwin et al. |
| 5,618,552 A | 4/1997 | Bezwada et al. |
| 5,620,458 A | 4/1997 | Green et al. |
| 5,620,698 A | 4/1997 | Bezwada et al. |
| 5,624,447 A | 4/1997 | Myers |
| 5,626,613 A | 5/1997 | Schmieding |
| 5,628,751 A | 5/1997 | Sander et al. |
| 5,628,752 A | 5/1997 | Asnis et al. |
| 5,632,746 A | 5/1997 | Middleman et al. |
| 5,639,276 A | 6/1997 | Weinstock et al. |
| 5,643,320 A | 7/1997 | Lower et al. |
| 5,645,589 A | 7/1997 | Li |
| 5,645,596 A | 7/1997 | Kim et al. |
| 5,645,597 A | 7/1997 | Krapiva |
| 5,645,598 A | 7/1997 | Brosnahan, III |
| 5,645,599 A | 7/1997 | Samani |
| 5,645,850 A | 7/1997 | Bezwada et al. |
| 5,647,857 A | 7/1997 | Anderson et al. |
| 5,648,088 A | 7/1997 | Bezwada et al. |
| 5,649,931 A | 7/1997 | Bryant et al. |
| 5,653,763 A | 8/1997 | Errico et al. |
| 5,658,335 A | 8/1997 | Allen |
| 5,662,655 A | 9/1997 | Laboureau et al. |
| 5,662,658 A | 9/1997 | Wenstrom, Jr. |
| 5,662,683 A | 9/1997 | Kay |
| 5,665,095 A | 9/1997 | Jacobson et al. |
| 5,665,122 A | 9/1997 | Kambin |
| 5,667,508 A | 9/1997 | Errico et al. |
| 5,669,915 A | 9/1997 | Caspar et al. |
| 5,669,926 A | 9/1997 | Aust et al. |
| 5,674,294 A | 10/1997 | Bainville et al. |
| 5,674,295 A | 10/1997 | Ray et al. |
| 5,674,296 A | 10/1997 | Bryan et al. |
| 5,676,666 A | 10/1997 | Oxland et al. |
| 5,676,701 A | 10/1997 | Yuan et al. |
| 5,679,723 A | 10/1997 | Cooper et al. |
| 5,681,263 A | 10/1997 | Flesch |
| 5,683,465 A | 11/1997 | Shinn et al. |
| 5,693,100 A | 12/1997 | Pisharodi |
| 5,695,513 A | 12/1997 | Johnson et al. |
| 5,697,977 A | 12/1997 | Pisharodi |
| 5,698,213 A | 12/1997 | Jamiolkowski et al. |
| 5,700,239 A | 12/1997 | Yoon |
| 5,700,583 A | 12/1997 | Jamiolkowski et al. |
| 5,702,391 A | 12/1997 | Lin |
| 5,702,449 A | 12/1997 | McKay |
| 5,702,450 A | 12/1997 | Bisserie |
| 5,702,453 A | 12/1997 | Rabbe et al. |
| 5,702,454 A | 12/1997 | Baumgartner |
| 5,707,359 A | 1/1998 | Bufalini |
| 5,713,870 A | 2/1998 | Yoon |
| 5,713,899 A | 2/1998 | Marnay et al. |
| 5,713,903 A | 2/1998 | Sander et al. |
| 5,716,415 A | 2/1998 | Steffee |
| 5,716,416 A | 2/1998 | Lin |
| 5,720,753 A | 2/1998 | Sander et al. |
| 5,725,541 A | 3/1998 | Anspach et al. |
| 5,725,588 A | 3/1998 | Errico et al. |
| 5,728,097 A | 3/1998 | Mathews |
| 5,728,116 A | 3/1998 | Rosenman |
| 5,735,853 A | 4/1998 | Olerud |
| 5,741,253 A | 4/1998 | Michelson |
| 5,741,282 A | 4/1998 | Anspach et al. |
| 5,743,881 A | 4/1998 | Demco |
| 5,743,912 A | 4/1998 | Lahille et al. |
| 5,743,914 A | 4/1998 | Skiba |
| 5,749,879 A | 5/1998 | Middleman et al. |
| 5,749,889 A | 5/1998 | Bacich et al. |
| 5,752,969 A | 5/1998 | Cunci et al. |
| 5,755,796 A | 5/1998 | Ibo et al. |
| 5,755,797 A | 5/1998 | Baumgartner |
| 5,755,798 A | 5/1998 | Papavero et al. |
| 5,756,127 A | 5/1998 | Grisoni et al. |
| 5,762,500 A | 6/1998 | Lazarof |
| 5,762,629 A | 6/1998 | Kambin |
| 5,766,252 A | 6/1998 | Henry et al. |

(56) References Cited

U.S. PATENT DOCUMENTS

| | | |
|---|---|---|
| 5,772,661 A | 6/1998 | Michelson |
| 5,772,662 A | 6/1998 | Chapman et al. |
| 5,772,678 A | 6/1998 | Thomason et al. |
| 5,776,156 A | 7/1998 | Shikhman |
| 5,776,196 A | 7/1998 | Matsuzaki et al. |
| 5,779,707 A | 7/1998 | Bertholet et al. |
| 5,782,800 A | 7/1998 | Yoon |
| 5,782,832 A | 7/1998 | Larsen et al. |
| 5,782,865 A | 7/1998 | Grotz |
| 5,785,713 A | 7/1998 | Jobe |
| 5,788,698 A | 8/1998 | Savornin |
| 5,788,703 A | 8/1998 | Mittelmeier et al. |
| 5,792,044 A | 8/1998 | Foley et al. |
| 5,797,909 A | 8/1998 | Michelson |
| 5,797,912 A | 8/1998 | Runciman et al. |
| 5,797,918 A | 8/1998 | McGuire et al. |
| 5,800,435 A | 9/1998 | Errico et al. |
| 5,800,440 A | 9/1998 | Stead |
| 5,800,549 A | 9/1998 | Bao et al. |
| 5,807,275 A | 9/1998 | Jamshidi |
| 5,807,327 A | 9/1998 | Green et al. |
| 5,810,721 A | 9/1998 | Mueller et al. |
| 5,810,821 A | 9/1998 | Vandewalle |
| 5,810,866 A | 9/1998 | Yoon |
| 5,814,084 A | 9/1998 | Grivas et al. |
| 5,820,628 A | 10/1998 | Middleman et al. |
| 5,823,979 A | 10/1998 | Mezo |
| 5,824,084 A | 10/1998 | Muschler |
| 5,824,093 A | 10/1998 | Ray et al. |
| 5,824,094 A | 10/1998 | Serhan et al. |
| 5,827,289 A | 10/1998 | Reiley et al. |
| 5,833,657 A | 11/1998 | Reinhardt et al. |
| 5,836,948 A | 11/1998 | Zucherman et al. |
| 5,837,752 A | 11/1998 | Shastri et al. |
| 5,846,259 A | 12/1998 | Berthiaume |
| 5,848,986 A | 12/1998 | Lundquist et al. |
| 5,849,004 A | 12/1998 | Bramlet |
| 5,851,212 A | 12/1998 | Zirps et al. |
| 5,851,216 A | 12/1998 | Allen |
| 5,859,150 A | 1/1999 | Jamiolkowski et al. |
| 5,860,973 A | 1/1999 | Michelson |
| 5,860,977 A | 1/1999 | Zucherman et al. |
| 5,865,846 A | 2/1999 | Bryan et al. |
| 5,865,848 A | 2/1999 | Baker |
| 5,871,485 A | 2/1999 | Rao et al. |
| 5,873,854 A | 2/1999 | Wolvek |
| 5,876,404 A | 3/1999 | Zucherman et al. |
| 5,888,220 A | 3/1999 | Felt et al. |
| 5,888,221 A | 3/1999 | Gelbard |
| 5,888,223 A | 3/1999 | Bray, Jr. |
| 5,888,224 A | 3/1999 | Beckers et al. |
| 5,888,226 A | 3/1999 | Rogozinski |
| 5,888,227 A | 3/1999 | Cottle |
| 5,888,228 A | 3/1999 | Knothe et al. |
| 5,893,850 A | 4/1999 | Cachia |
| 5,893,889 A | 4/1999 | Harrington |
| 5,893,890 A | 4/1999 | Pisharodi |
| 5,895,428 A | 4/1999 | Berry |
| 5,902,231 A | 5/1999 | Foley et al. |
| 5,904,689 A | 5/1999 | Jonjic |
| 5,904,690 A | 5/1999 | Middleman et al. |
| 5,904,696 A | 5/1999 | Rosenman |
| 5,908,422 A | 6/1999 | Bresina |
| 5,913,860 A | 6/1999 | Scholl |
| 5,919,235 A | 7/1999 | Husson et al. |
| 5,925,074 A | 7/1999 | Gingras et al. |
| 5,928,235 A | 7/1999 | Friedl |
| 5,928,244 A | 7/1999 | Tovey et al. |
| 5,928,422 A | 7/1999 | Uchiyama et al. |
| 5,931,870 A | 8/1999 | Cuckler et al. |
| 5,935,129 A | 8/1999 | McDevitt et al. |
| 5,947,999 A | 9/1999 | Groiso |
| 5,948,000 A | 9/1999 | Larsen et al. |
| 5,954,722 A | 9/1999 | Bono |
| 5,954,747 A | 9/1999 | Clark |
| 5,957,902 A | 9/1999 | Teves |
| 5,957,924 A | 9/1999 | Toermaelae et al. |
| 5,961,554 A | 10/1999 | Janson et al. |
| 5,964,730 A | 10/1999 | Williams et al. |
| 5,964,761 A | 10/1999 | Kambin |
| 5,967,783 A | 10/1999 | Ura |
| 5,967,970 A | 10/1999 | Cowan et al. |
| 5,968,044 A | 10/1999 | Nicholson et al. |
| 5,968,098 A | 10/1999 | Winslow |
| 5,972,015 A | 10/1999 | Scribner et al. |
| 5,972,385 A | 10/1999 | Liu et al. |
| 5,976,139 A | 11/1999 | Bramlet |
| 5,976,146 A | 11/1999 | Ogawa et al. |
| 5,976,186 A | 11/1999 | Bao et al. |
| 5,980,522 A | 11/1999 | Koros et al. |
| 5,984,927 A | 11/1999 | Wenstrom et al. |
| 5,984,966 A | 11/1999 | Kiema et al. |
| 5,985,307 A | 11/1999 | Hanson et al. |
| 5,989,255 A | 11/1999 | Pepper et al. |
| 5,989,291 A | 11/1999 | Ralph et al. |
| 5,993,459 A | 11/1999 | Larsen et al. |
| 5,997,510 A | 12/1999 | Schwemberger |
| 5,997,538 A | 12/1999 | Asnis et al. |
| 5,997,541 A | 12/1999 | Schenk |
| 6,001,100 A | 12/1999 | Sherman et al. |
| 6,001,101 A | 12/1999 | Augagneur et al. |
| 6,004,327 A | 12/1999 | Asnis et al. |
| 6,005,161 A | 12/1999 | Brekke |
| 6,007,519 A | 12/1999 | Rosselli |
| 6,007,566 A | 12/1999 | Wenstrom, Jr. |
| 6,007,580 A | 12/1999 | Lento et al. |
| 6,010,508 A | 1/2000 | Bradley |
| 6,010,513 A | 1/2000 | Toermaelae et al. |
| 6,012,494 A | 1/2000 | Balazs |
| 6,015,410 A | 1/2000 | Toermaelae et al. |
| 6,015,436 A | 1/2000 | Schoenhoeffer |
| 6,019,762 A | 2/2000 | Cole |
| 6,019,792 A | 2/2000 | Cauthen |
| 6,019,793 A | 2/2000 | Perren et al. |
| 6,022,350 A | 2/2000 | Ganem |
| 6,022,352 A | 2/2000 | Vandewalle |
| 6,030,162 A | 2/2000 | Huebner |
| 6,030,364 A | 2/2000 | Durgin et al. |
| 6,030,401 A | 2/2000 | Marino |
| 6,033,406 A | 3/2000 | Mathews |
| 6,033,412 A | 3/2000 | Losken et al. |
| 6,036,701 A | 3/2000 | Rosenman |
| 6,039,740 A | 3/2000 | Olerud |
| 6,039,761 A | 3/2000 | Li et al. |
| 6,039,763 A | 3/2000 | Shelokov |
| 6,045,552 A | 4/2000 | Zucherman et al. |
| 6,045,579 A | 4/2000 | Hochschuler et al. |
| 6,048,309 A | 4/2000 | Flom et al. |
| 6,048,342 A | 4/2000 | Zucherman et al. |
| 6,048,346 A | 4/2000 | Reiley et al. |
| 6,048,360 A | 4/2000 | Khosravi et al. |
| 6,049,026 A | 4/2000 | Muschler |
| 6,053,935 A | 4/2000 | Brenneman et al. |
| 6,056,749 A | 5/2000 | Kuslich |
| 6,063,121 A | 5/2000 | Xavier et al. |
| 6,066,142 A | 5/2000 | Serbousek et al. |
| 6,066,154 A | 5/2000 | Reiley et al. |
| 6,066,175 A | 5/2000 | Henderson et al. |
| 6,068,630 A | 5/2000 | Zucherman et al. |
| 6,068,648 A | 5/2000 | Cole et al. |
| 6,071,982 A | 6/2000 | Wise et al. |
| 6,073,051 A | 6/2000 | Sharkey et al. |
| 6,074,390 A | 6/2000 | Zucherman et al. |
| 6,080,155 A | 6/2000 | Michelson |
| 6,080,193 A | 6/2000 | Hochschuler et al. |
| 6,083,225 A | 7/2000 | Winslow et al. |
| 6,083,244 A | 7/2000 | Lubbers et al. |
| 6,086,593 A | 7/2000 | Bonutti |
| 6,090,112 A | 7/2000 | Zucherman et al. |
| 6,090,143 A | 7/2000 | Meriwether et al. |
| 6,093,205 A | 7/2000 | McLeod et al. |
| 6,096,038 A | 8/2000 | Michelson |
| 6,096,080 A | 8/2000 | Nicholson et al. |
| 6,099,531 A | 8/2000 | Bonutti |

(56) References Cited

U.S. PATENT DOCUMENTS

| | | |
|---|---|---|
| 6,102,914 A | 8/2000 | Bulstra et al. |
| 6,102,950 A | 8/2000 | Vaccaro |
| 6,106,557 A | 8/2000 | Robioneck et al. |
| 6,110,210 A | 8/2000 | Norton et al. |
| 6,113,624 A | 9/2000 | Bezwada et al. |
| 6,113,636 A | 9/2000 | Ogle |
| 6,113,637 A | 9/2000 | Gill et al. |
| 6,113,638 A | 9/2000 | Williams et al. |
| 6,113,640 A | 9/2000 | Toermaelae et al. |
| 6,117,174 A | 9/2000 | Nolan |
| 6,119,044 A | 9/2000 | Kuzma |
| 6,120,503 A | 9/2000 | Michelson |
| 6,123,705 A | 9/2000 | Michelson |
| 6,123,711 A | 9/2000 | Winters |
| 6,126,660 A | 10/2000 | Dietz |
| 6,126,661 A | 10/2000 | Faccioli et al. |
| 6,126,663 A | 10/2000 | Hair |
| 6,126,686 A | 10/2000 | Badylak et al. |
| 6,126,689 A | 10/2000 | Brett |
| 6,127,597 A | 10/2000 | Beyar et al. |
| 6,129,762 A | 10/2000 | Li |
| 6,129,763 A | 10/2000 | Chauvin et al. |
| 6,132,435 A | 10/2000 | Young |
| 6,136,031 A | 10/2000 | Middleton |
| 6,139,550 A | 10/2000 | Michelson |
| 6,139,579 A | 10/2000 | Steffee et al. |
| 6,146,384 A | 11/2000 | Lee et al. |
| 6,146,387 A | 11/2000 | Trott et al. |
| 6,146,420 A | 11/2000 | McKay |
| 6,146,421 A | 11/2000 | Gordon et al. |
| 6,147,135 A | 11/2000 | Yuan et al. |
| 6,149,652 A | 11/2000 | Zucherman et al. |
| 6,152,926 A | 11/2000 | Zucherman et al. |
| 6,156,037 A | 12/2000 | Lehuec et al. |
| 6,156,038 A | 12/2000 | Zucherman et al. |
| 6,159,179 A | 12/2000 | Simonson |
| 6,159,211 A | 12/2000 | Boriani et al. |
| 6,159,244 A | 12/2000 | Suddaby |
| 6,161,350 A | 12/2000 | Espinosa |
| 6,162,234 A | 12/2000 | Freedland et al. |
| 6,162,236 A | 12/2000 | Osada |
| 6,162,252 A | 12/2000 | Kuras et al. |
| 6,165,218 A | 12/2000 | Husson et al. |
| 6,165,486 A | 12/2000 | Marra et al. |
| 6,168,595 B1 | 1/2001 | Durham et al. |
| 6,168,597 B1 | 1/2001 | Biedermann et al. |
| 6,171,610 B1 | 1/2001 | Vacanti et al. |
| 6,174,311 B1 | 1/2001 | Branch et al. |
| 6,174,337 B1 | 1/2001 | Keenan |
| 6,175,758 B1 | 1/2001 | Kambin |
| 6,176,882 B1 | 1/2001 | Biedermann et al. |
| 6,179,794 B1 | 1/2001 | Burras |
| 6,179,873 B1 | 1/2001 | Zientek |
| 6,179,875 B1 | 1/2001 | Von Strempel |
| 6,183,471 B1 | 2/2001 | Zucherman et al. |
| 6,183,472 B1 | 2/2001 | Lutz |
| 6,183,474 B1 | 2/2001 | Bramlet et al. |
| 6,183,517 B1 | 2/2001 | Suddaby |
| 6,187,043 B1 | 2/2001 | Ledergerber |
| 6,187,048 B1 | 2/2001 | Milner et al. |
| 6,190,387 B1 | 2/2001 | Zucherman et al. |
| 6,190,414 B1 | 2/2001 | Young et al. |
| 6,193,757 B1 | 2/2001 | Foley et al. |
| 6,197,033 B1 | 3/2001 | Haid et al. |
| 6,197,041 B1 | 3/2001 | Shichman et al. |
| 6,197,065 B1 | 3/2001 | Martin et al. |
| 6,197,325 B1 | 3/2001 | MacPhee et al. |
| 6,200,306 B1 | 3/2001 | Klostermeyer et al. |
| 6,200,322 B1 | 3/2001 | Branch et al. |
| 6,203,565 B1 | 3/2001 | Bonutti et al. |
| 6,206,826 B1 | 3/2001 | Mathews et al. |
| 6,206,922 B1 | 3/2001 | Zdeblick et al. |
| D439,980 S | 4/2001 | Reiley et al. |
| 6,213,957 B1 | 4/2001 | Milliman et al. |
| 6,214,368 B1 | 4/2001 | Lee et al. |
| 6,217,509 B1 | 4/2001 | Foley et al. |
| 6,217,579 B1 | 4/2001 | Koros |
| 6,221,082 B1 | 4/2001 | Marino et al. |
| 6,224,602 B1 | 5/2001 | Hayes |
| 6,224,603 B1 | 5/2001 | Marino |
| 6,224,631 B1 | 5/2001 | Kohrs |
| 6,224,894 B1 | 5/2001 | Jamiolkowski et al. |
| 6,228,058 B1 | 5/2001 | Dennis et al. |
| 6,231,606 B1 | 5/2001 | Graf et al. |
| 6,231,610 B1 | 5/2001 | Geisler |
| 6,235,030 B1 | 5/2001 | Zucherman et al. |
| 6,235,043 B1 | 5/2001 | Reiley et al. |
| 6,235,059 B1 | 5/2001 | Benezech et al. |
| 6,238,397 B1 | 5/2001 | Zucherman et al. |
| 6,238,491 B1 | 5/2001 | Davidson et al. |
| 6,241,732 B1 | 6/2001 | Overaker et al. |
| 6,241,734 B1 | 6/2001 | Scribner et al. |
| 6,241,769 B1 | 6/2001 | Nicholson et al. |
| 6,245,107 B1 | 6/2001 | Ferree |
| 6,248,108 B1 | 6/2001 | Toermaelae et al. |
| 6,248,110 B1 | 6/2001 | Reiley et al. |
| 6,248,131 B1 | 6/2001 | Felt et al. |
| 6,251,111 B1 | 6/2001 | Barker et al. |
| 6,251,140 B1 | 6/2001 | Marino et al. |
| 6,261,289 B1 | 7/2001 | Levy |
| 6,264,676 B1 | 7/2001 | Gellman et al. |
| 6,264,695 B1 | 7/2001 | Stoy |
| 6,267,763 B1 | 7/2001 | Castro |
| 6,267,765 B1 | 7/2001 | Taylor et al. |
| 6,267,767 B1 | 7/2001 | Strobel et al. |
| 6,273,893 B1 | 8/2001 | McAllen et al. |
| 6,277,149 B1 | 8/2001 | Boyle et al. |
| 6,280,444 B1 | 8/2001 | Zucherman et al. |
| 6,280,456 B1 | 8/2001 | Scribner et al. |
| 6,280,474 B1 | 8/2001 | Cassidy et al. |
| 6,280,475 B1 | 8/2001 | Bao et al. |
| 6,287,313 B1 | 9/2001 | Sasso |
| 6,290,701 B1 | 9/2001 | Enayati |
| 6,290,724 B1 | 9/2001 | Marino |
| 6,293,909 B1 | 9/2001 | Chu et al. |
| 6,293,952 B1 | 9/2001 | Brosens et al. |
| D449,691 S | 10/2001 | Reiley et al. |
| 6,296,647 B1 | 10/2001 | Robioneck et al. |
| 6,302,914 B1 | 10/2001 | Michelson |
| 6,306,136 B1 | 10/2001 | Baccelli |
| 6,306,170 B2 | 10/2001 | Ray |
| 6,306,177 B1 | 10/2001 | Felt et al. |
| 6,312,443 B1 | 11/2001 | Stone |
| 6,319,252 B1 | 11/2001 | McDevitt et al. |
| 6,319,254 B1 | 11/2001 | Giet et al. |
| 6,319,272 B1 | 11/2001 | Brenneman et al. |
| 6,330,845 B1 | 12/2001 | Meulink |
| 6,331,312 B1 | 12/2001 | Lee et al. |
| 6,332,882 B1 | 12/2001 | Zucherman et al. |
| 6,332,883 B1 | 12/2001 | Zucherman et al. |
| 6,332,894 B1 | 12/2001 | Stalcup et al. |
| 6,332,895 B1 | 12/2001 | Suddaby |
| 6,336,928 B1 | 1/2002 | Guerin et al. |
| 6,342,055 B1 | 1/2002 | Eisermann et al. |
| 6,342,074 B1 | 1/2002 | Simpson |
| 6,346,092 B1 | 2/2002 | Leschinsky |
| 6,348,053 B1 | 2/2002 | Cachia |
| 6,355,043 B1 | 3/2002 | Adam |
| 6,361,537 B1 | 3/2002 | Anderson |
| 6,361,538 B1 | 3/2002 | Fenaroli et al. |
| 6,361,557 B1 | 3/2002 | Gittings et al. |
| 6,364,828 B1 | 4/2002 | Yeung et al. |
| 6,364,880 B1 | 4/2002 | Michelson |
| 6,364,897 B1 | 4/2002 | Bonutti |
| 6,368,325 B1 | 4/2002 | McKinley et al. |
| 6,368,350 B1 | 4/2002 | Erickson et al. |
| 6,368,351 B1 | 4/2002 | Glenn et al. |
| 6,371,971 B1 | 4/2002 | Tsugita et al. |
| 6,371,989 B1 | 4/2002 | Chauvin et al. |
| 6,374,971 B1 | 4/2002 | Siciliano et al. |
| 6,375,462 B2 | 4/2002 | Holweg et al. |
| 6,375,681 B1 | 4/2002 | Truscott |
| 6,375,682 B1 | 4/2002 | Fleischmann et al. |
| 6,379,355 B1 | 4/2002 | Zucherman et al. |

(56) References Cited

U.S. PATENT DOCUMENTS

| | | |
|---|---|---|
| 6,379,363 B1 | 4/2002 | Herrington et al. |
| 6,387,130 B1 | 5/2002 | Stone et al. |
| 6,395,031 B1 | 5/2002 | Foley et al. |
| 6,402,750 B1 | 6/2002 | Atkinson et al. |
| 6,406,234 B2 | 6/2002 | Frigg |
| 6,406,478 B1 | 6/2002 | Kuo |
| 6,409,766 B1 | 6/2002 | Brett |
| 6,409,767 B1 | 6/2002 | Perice et al. |
| 6,413,278 B1 | 7/2002 | Marchosky |
| 6,416,551 B1 | 7/2002 | Keller |
| 6,419,641 B1 | 7/2002 | Mark et al. |
| 6,419,676 B1 | 7/2002 | Zucherman et al. |
| 6,419,677 B2 | 7/2002 | Zucherman et al. |
| 6,419,704 B1 | 7/2002 | Ferree |
| 6,419,705 B1 | 7/2002 | Erickson |
| 6,419,706 B1 | 7/2002 | Graf |
| 6,423,061 B1 | 7/2002 | Bryant |
| 6,423,063 B1 | 7/2002 | Bonutti |
| 6,423,067 B1 | 7/2002 | Eisermann |
| 6,423,071 B1 | 7/2002 | Lawson |
| 6,423,083 B2 | 7/2002 | Reiley et al. |
| 6,423,089 B1 | 7/2002 | Gingras et al. |
| 6,425,887 B1 | 7/2002 | McGuckin et al. |
| 6,425,919 B1 | 7/2002 | Lambrecht |
| 6,425,920 B1 | 7/2002 | Hamada |
| 6,428,541 B1 | 8/2002 | Boyd et al. |
| 6,428,556 B1 | 8/2002 | Chin |
| 6,428,575 B2 | 8/2002 | Koo et al. |
| 6,432,106 B1 | 8/2002 | Fraser |
| 6,436,140 B1 | 8/2002 | Liu et al. |
| 6,436,143 B1 | 8/2002 | Ross et al. |
| 6,440,138 B1 | 8/2002 | Reiley et al. |
| 6,440,154 B2 | 8/2002 | Gellman et al. |
| 6,440,169 B1 | 8/2002 | Elberg et al. |
| 6,443,989 B1 | 9/2002 | Jackson |
| 6,447,527 B1 | 9/2002 | Thompson et al. |
| 6,447,540 B1 | 9/2002 | Fontaine et al. |
| 6,447,544 B1 | 9/2002 | Michelson |
| 6,447,546 B1 | 9/2002 | Bramlet et al. |
| 6,450,989 B2 | 9/2002 | Dubrul et al. |
| 6,451,019 B1 | 9/2002 | Zucherman et al. |
| 6,451,020 B1 | 9/2002 | Zucherman et al. |
| 6,454,769 B2 | 9/2002 | Wagner et al. |
| 6,454,806 B1 | 9/2002 | Cohen et al. |
| 6,454,807 B1 | 9/2002 | Jackson |
| 6,458,134 B1 | 10/2002 | Songer et al. |
| 6,461,359 B1 | 10/2002 | Tribus et al. |
| 6,468,277 B1 | 10/2002 | Justin et al. |
| 6,468,279 B1 | 10/2002 | Reo |
| 6,468,309 B1 | 10/2002 | Lieberman |
| 6,468,310 B1 | 10/2002 | Ralph et al. |
| 6,471,724 B2 | 10/2002 | Zdeblick et al. |
| 6,475,226 B1 | 11/2002 | Belef et al. |
| 6,478,029 B1 | 11/2002 | Boyd et al. |
| 6,478,796 B2 | 11/2002 | Zucherman et al. |
| 6,478,805 B1 | 11/2002 | Marino et al. |
| 6,482,235 B1 | 11/2002 | Lambrecht et al. |
| 6,485,491 B1 | 11/2002 | Farris et al. |
| 6,485,518 B1 | 11/2002 | Cornwall et al. |
| D467,657 S | 12/2002 | Scribner |
| 6,488,693 B2 | 12/2002 | Gannoe et al. |
| 6,488,710 B2 | 12/2002 | Besselink |
| 6,489,309 B1 | 12/2002 | Singh et al. |
| 6,491,626 B1 | 12/2002 | Stone et al. |
| 6,491,695 B1 | 12/2002 | Roggenbuck |
| 6,491,714 B1 | 12/2002 | Bennett |
| 6,491,724 B1 | 12/2002 | Ferree |
| 6,494,860 B2 | 12/2002 | Rocamora et al. |
| 6,494,883 B1 | 12/2002 | Ferree |
| 6,494,893 B2 | 12/2002 | Dubrul et al. |
| 6,498,421 B1 | 12/2002 | Oh et al. |
| 6,500,178 B2 | 12/2002 | Zucherman et al. |
| 6,500,205 B1 | 12/2002 | Michelson |
| 6,506,192 B1 | 1/2003 | Gertzman et al. |
| 6,508,818 B2 | 1/2003 | Steiner et al. |
| 6,508,839 B1 | 1/2003 | Lambrecht et al. |
| 6,511,471 B2 | 1/2003 | Rosenman et al. |
| 6,511,481 B2 | 1/2003 | Von et al. |
| 6,512,958 B1 | 1/2003 | Swoyer et al. |
| D469,871 S | 2/2003 | Sand |
| 6,514,256 B2 | 2/2003 | Zucherman et al. |
| 6,517,543 B1 | 2/2003 | Berrevoets et al. |
| 6,517,580 B1 | 2/2003 | Ramadan et al. |
| 6,520,907 B1 | 2/2003 | Foley et al. |
| 6,520,991 B2 | 2/2003 | Huene |
| D472,323 S | 3/2003 | Sand |
| 6,527,772 B2 | 3/2003 | Enayati |
| 6,527,774 B2 | 3/2003 | Lieberman |
| 6,527,803 B1 | 3/2003 | Crozet et al. |
| 6,527,804 B1 | 3/2003 | Gauchet et al. |
| 6,530,930 B1 | 3/2003 | Marino et al. |
| 6,533,791 B1 | 3/2003 | Betz et al. |
| 6,533,797 B1 | 3/2003 | Stone et al. |
| 6,533,818 B1 | 3/2003 | Weber et al. |
| 6,540,747 B1 | 4/2003 | Marino |
| 6,544,265 B2 | 4/2003 | Lieberman |
| 6,547,793 B1 | 4/2003 | McGuire |
| 6,547,795 B2 | 4/2003 | Schneiderman |
| 6,547,823 B2 | 4/2003 | Scarborough et al. |
| 6,551,319 B2 | 4/2003 | Lieberman |
| 6,551,322 B1 | 4/2003 | Lieberman |
| 6,554,831 B1 | 4/2003 | Rivard et al. |
| 6,554,833 B2 | 4/2003 | Levy et al. |
| 6,554,852 B1 | 4/2003 | Oberlander |
| 6,558,387 B2 | 5/2003 | Errico et al. |
| 6,558,389 B2 | 5/2003 | Clark et al. |
| 6,558,390 B2 | 5/2003 | Cragg |
| 6,558,423 B1 | 5/2003 | Michelson |
| 6,558,424 B2 | 5/2003 | Thalgott |
| 6,562,046 B2 | 5/2003 | Sasso |
| 6,562,049 B1 | 5/2003 | Norlander et al. |
| 6,562,072 B1 | 5/2003 | Fuss et al. |
| 6,562,073 B2 | 5/2003 | Foley |
| 6,562,074 B2 | 5/2003 | Gerbec et al. |
| 6,565,570 B2 | 5/2003 | Sterett et al. |
| 6,572,619 B2 | 6/2003 | Santilli |
| 6,575,919 B1 | 6/2003 | Reiley et al. |
| 6,575,976 B2 | 6/2003 | Grafton |
| 6,575,979 B1 | 6/2003 | Cragg |
| 6,576,016 B1 | 6/2003 | Hochshuler et al. |
| 6,579,290 B1 | 6/2003 | Hardcastle et al. |
| 6,579,291 B1 | 6/2003 | Keith et al. |
| 6,579,293 B1 | 6/2003 | Chandran |
| 6,579,320 B1 | 6/2003 | Gauchet et al. |
| 6,582,390 B1 | 6/2003 | Sanderson |
| 6,582,431 B1 | 6/2003 | Ray |
| 6,582,433 B2 | 6/2003 | Yun |
| 6,582,437 B2 | 6/2003 | Dorchak et al. |
| 6,582,441 B1 | 6/2003 | He et al. |
| 6,582,453 B1 | 6/2003 | Tran et al. |
| 6,582,466 B1 | 6/2003 | Gauchet |
| 6,582,467 B1 | 6/2003 | Teitelbaum et al. |
| 6,582,468 B1 | 6/2003 | Gauchet |
| 6,585,730 B1 | 7/2003 | Foerster |
| 6,585,740 B2 | 7/2003 | Schlapfer et al. |
| 6,589,240 B2 | 7/2003 | Hinchliffe |
| 6,589,244 B1 | 7/2003 | Sevrain et al. |
| 6,589,249 B2 | 7/2003 | Sater et al. |
| 6,592,553 B2 | 7/2003 | Zhang et al. |
| 6,592,624 B1 | 7/2003 | Fraser et al. |
| 6,592,625 B2 | 7/2003 | Cauthen |
| 6,595,998 B2 | 7/2003 | Johnson et al. |
| 6,596,008 B1 | 7/2003 | Kambin |
| 6,599,294 B2 | 7/2003 | Fuss et al. |
| 6,599,297 B1 | 7/2003 | Carlsson et al. |
| 6,602,257 B1 | 8/2003 | Thramann |
| 6,602,293 B1 | 8/2003 | Biermann et al. |
| 6,607,230 B2 | 8/2003 | Voves |
| 6,607,530 B1 | 8/2003 | Carl et al. |
| 6,607,544 B1 | 8/2003 | Boucher et al. |
| 6,607,558 B2 | 8/2003 | Kuras |
| 6,610,091 B1 | 8/2003 | Reiley |
| 6,610,094 B2 | 8/2003 | Husson |
| 6,613,050 B1 | 9/2003 | Wagner et al. |

(56) References Cited

U.S. PATENT DOCUMENTS

| | | |
|---|---|---|
| 6,613,054 B2 | 9/2003 | Scribner et al. |
| 6,616,678 B2 | 9/2003 | Nishtala et al. |
| 6,620,196 B1 | 9/2003 | Trieu |
| 6,623,505 B2 | 9/2003 | Scribner et al. |
| 6,626,943 B2 | 9/2003 | Eberlein et al. |
| 6,626,944 B1 | 9/2003 | Taylor |
| 6,629,998 B1 | 10/2003 | Lin |
| 6,632,224 B2 | 10/2003 | Cachia et al. |
| 6,632,235 B2 | 10/2003 | Weikel et al. |
| 6,635,059 B2 | 10/2003 | Randall et al. |
| 6,635,362 B2 | 10/2003 | Zheng |
| D482,787 S | 11/2003 | Reiss |
| 6,641,534 B2 | 11/2003 | Smith et al. |
| 6,641,564 B1 | 11/2003 | Kraus |
| 6,641,587 B2 | 11/2003 | Scribner et al. |
| 6,641,614 B1 | 11/2003 | Wagner et al. |
| 6,645,213 B2 | 11/2003 | Sand et al. |
| 6,645,248 B2 | 11/2003 | Casutt |
| 6,648,890 B2 | 11/2003 | Culbert et al. |
| 6,648,893 B2 | 11/2003 | Dudasik |
| 6,648,917 B2 | 11/2003 | Gerbec et al. |
| 6,652,527 B2 | 11/2003 | Zucherman et al. |
| 6,652,592 B1 | 11/2003 | Grooms et al. |
| D483,495 S | 12/2003 | Sand |
| 6,655,962 B1 | 12/2003 | Kennard |
| 6,656,178 B1 | 12/2003 | Veldhuizen et al. |
| 6,656,180 B2 | 12/2003 | Stahurski |
| 6,660,037 B1 | 12/2003 | Husson et al. |
| 6,663,647 B2 | 12/2003 | Reiley et al. |
| 6,666,890 B2 | 12/2003 | Michelson |
| 6,666,891 B2 | 12/2003 | Boehm et al. |
| 6,669,698 B1 | 12/2003 | Tromanhauser et al. |
| 6,669,729 B2 | 12/2003 | Chin |
| 6,669,732 B2 | 12/2003 | Serhan et al. |
| 6,672,977 B1 | 1/2004 | Colbo et al. |
| 6,673,074 B2 | 1/2004 | Shluzas |
| 6,676,663 B2 | 1/2004 | Higueras et al. |
| 6,676,664 B1 | 1/2004 | Al-Assir |
| 6,676,665 B2 | 1/2004 | Foley et al. |
| 6,679,833 B2 | 1/2004 | Smith et al. |
| 6,682,535 B2 | 1/2004 | Hoogland |
| 6,682,561 B2 | 1/2004 | Songer et al. |
| 6,682,562 B2 | 1/2004 | Viart et al. |
| 6,682,563 B2 | 1/2004 | Scharf |
| 6,685,706 B2 | 2/2004 | Padget et al. |
| 6,685,742 B1 | 2/2004 | Jackson |
| 6,689,125 B1 | 2/2004 | Keith et al. |
| 6,689,152 B2 | 2/2004 | Balceta et al. |
| 6,689,168 B2 | 2/2004 | Lieberman |
| 6,692,499 B2 | 2/2004 | Toermaelae et al. |
| 6,692,563 B2 | 2/2004 | Zimmermann |
| 6,695,842 B2 | 2/2004 | Zucherman et al. |
| 6,695,846 B2 | 2/2004 | Richelsoph et al. |
| 6,695,851 B2 | 2/2004 | Zdeblick et al. |
| 6,699,246 B2 | 3/2004 | Zucherman et al. |
| 6,699,247 B2 | 3/2004 | Zucherman et al. |
| 6,706,070 B1 | 3/2004 | Wagner et al. |
| 6,709,458 B2 | 3/2004 | Michelson |
| 6,712,819 B2 | 3/2004 | Zucherman et al. |
| 6,716,216 B1 | 4/2004 | Boucher et al. |
| 6,716,247 B2 | 4/2004 | Michelson |
| 6,716,957 B2 | 4/2004 | Tunc |
| 6,719,760 B2 | 4/2004 | Dorchak et al. |
| 6,719,761 B1 | 4/2004 | Reiley et al. |
| 6,719,773 B1 | 4/2004 | Boucher et al. |
| 6,719,796 B2 | 4/2004 | Cohen et al. |
| 6,723,096 B1 | 4/2004 | Dorchak et al. |
| 6,723,126 B1 | 4/2004 | Berry |
| 6,723,127 B2 | 4/2004 | Ralph et al. |
| 6,723,128 B2 | 4/2004 | Uk |
| 6,726,691 B2 | 4/2004 | Osorio et al. |
| D490,159 S | 5/2004 | Sand |
| 6,730,125 B1 | 5/2004 | Lin |
| 6,730,126 B2 | 5/2004 | Boehm et al. |
| 6,730,127 B2 | 5/2004 | Michelson |
| 6,733,093 B2 | 5/2004 | Deland et al. |
| 6,733,460 B2 | 5/2004 | Ogura |
| 6,733,531 B1 | 5/2004 | Trieu |
| 6,733,532 B1 | 5/2004 | Gauchet et al. |
| 6,733,534 B2 | 5/2004 | Sherman |
| 6,733,535 B2 | 5/2004 | Michelson |
| 6,733,635 B1 | 5/2004 | Ozawa et al. |
| 6,736,850 B2 | 5/2004 | Davis |
| 6,740,090 B1 | 5/2004 | Cragg et al. |
| 6,740,093 B2 | 5/2004 | Hochschuler et al. |
| 6,740,117 B2 | 5/2004 | Ralph et al. |
| D492,032 S | 6/2004 | Muller et al. |
| 6,743,166 B2 | 6/2004 | Berci et al. |
| 6,743,255 B2 | 6/2004 | Ferree |
| 6,743,257 B2 | 6/2004 | Castro |
| 6,745,255 B2 | 6/2004 | Yen et al. |
| 6,746,451 B2 | 6/2004 | Middleton et al. |
| 6,749,560 B1 | 6/2004 | Konstorum et al. |
| 6,752,831 B2 | 6/2004 | Sybert et al. |
| 6,755,841 B2 | 6/2004 | Fraser et al. |
| D492,775 S | 7/2004 | Doelling et al. |
| D493,533 S | 7/2004 | Blain |
| 6,758,673 B2 | 7/2004 | Fromovich et al. |
| 6,758,861 B2 | 7/2004 | Ralph et al. |
| 6,758,862 B2 | 7/2004 | Berry et al. |
| 6,761,720 B1 | 7/2004 | Senegas |
| 6,761,738 B1 | 7/2004 | Boyd |
| 6,764,514 B1 | 7/2004 | Li et al. |
| D495,417 S | 8/2004 | Doelling et al. |
| 6,770,075 B2 | 8/2004 | Howland |
| 6,770,096 B2 | 8/2004 | Bolger et al. |
| 6,773,437 B2 | 8/2004 | Ogilvie et al. |
| 6,773,460 B2 | 8/2004 | Jackson |
| 6,776,781 B1 | 8/2004 | Uwaydah |
| 6,780,151 B2 | 8/2004 | Grabover et al. |
| 6,783,530 B1 | 8/2004 | Levy |
| 6,790,210 B1 | 9/2004 | Cragg et al. |
| 6,793,656 B1 | 9/2004 | Mathews |
| 6,793,678 B2 | 9/2004 | Hawkins |
| 6,793,679 B2 | 9/2004 | Michelson |
| 6,796,983 B1 | 9/2004 | Zucherman et al. |
| 6,805,685 B2 | 10/2004 | Taylor |
| 6,805,695 B2 | 10/2004 | Keith et al. |
| 6,805,697 B1 | 10/2004 | Helm et al. |
| 6,805,714 B2 | 10/2004 | Sutcliffe |
| 6,808,526 B1 | 10/2004 | Magerl et al. |
| 6,808,537 B2 | 10/2004 | Michelson |
| 6,810,094 B1 | 10/2004 | Lu |
| 6,811,567 B2 | 11/2004 | Reiley |
| 6,814,736 B2 | 11/2004 | Reiley et al. |
| 6,814,756 B1 | 11/2004 | Michelson |
| 6,821,298 B1 | 11/2004 | Jackson |
| 6,824,564 B2 | 11/2004 | Crozet |
| 6,824,565 B2 | 11/2004 | Muhanna et al. |
| 6,830,589 B2 | 12/2004 | Erickson |
| 6,833,006 B2 | 12/2004 | Foley et al. |
| 6,835,205 B2 | 12/2004 | Atkinson et al. |
| 6,835,206 B2 | 12/2004 | Jackson |
| 6,835,208 B2 | 12/2004 | Marchosky |
| 6,837,905 B1 | 1/2005 | Lieberman |
| 6,840,944 B2 | 1/2005 | Suddaby |
| 6,849,093 B2 | 2/2005 | Michelson |
| 6,852,126 B2 | 2/2005 | Ahlgren |
| 6,852,129 B2 | 2/2005 | Gerbec et al. |
| 6,855,167 B2 | 2/2005 | Shimp et al. |
| 6,863,668 B2 | 3/2005 | Gillespie et al. |
| 6,863,672 B2 | 3/2005 | Reiley et al. |
| 6,863,673 B2 | 3/2005 | Gerbec et al. |
| 6,866,682 B1 | 3/2005 | An et al. |
| 6,875,215 B2 | 4/2005 | Taras et al. |
| 6,881,228 B2 | 4/2005 | Zdeblick et al. |
| 6,881,229 B2 | 4/2005 | Khandkar et al. |
| 6,883,520 B2 | 4/2005 | Lambrecht et al. |
| 6,887,243 B2 | 5/2005 | Culbert |
| 6,887,248 B2 | 5/2005 | McKinley et al. |
| 6,890,333 B2 | 5/2005 | Von et al. |
| 6,890,335 B2 | 5/2005 | Grabowski et al. |
| 6,890,355 B2 | 5/2005 | Michelson |
| 6,893,464 B2 | 5/2005 | Kiester |

(56) References Cited

U.S. PATENT DOCUMENTS

| | | |
|---|---|---|
| 6,893,466 B2 | 5/2005 | Trieu |
| 6,899,716 B2 | 5/2005 | Cragg |
| 6,899,719 B2 | 5/2005 | Reiley et al. |
| 6,899,735 B2 | 5/2005 | Coates et al. |
| D506,828 S | 6/2005 | Layne et al. |
| 6,902,566 B2 | 6/2005 | Zucherman et al. |
| 6,905,512 B2 | 6/2005 | Paes et al. |
| 6,908,465 B2 | 6/2005 | Von et al. |
| 6,908,506 B2 | 6/2005 | Zimmermann |
| 6,916,323 B2 | 7/2005 | Kitchens |
| 6,921,403 B2 | 7/2005 | Cragg et al. |
| 6,923,810 B1 | 8/2005 | Michelson |
| 6,923,811 B1 | 8/2005 | Carl et al. |
| 6,923,813 B2 | 8/2005 | Phillips et al. |
| 6,923,814 B1 | 8/2005 | Hildebrand et al. |
| 6,929,606 B2 | 8/2005 | Ritland |
| 6,929,647 B2 | 8/2005 | Cohen |
| 6,936,071 B1 | 8/2005 | Marnay et al. |
| 6,936,072 B2 | 8/2005 | Lambrecht et al. |
| 6,942,668 B2 | 9/2005 | Padget et al. |
| 6,945,973 B2 | 9/2005 | Bray |
| 6,945,975 B2 | 9/2005 | Dalton |
| 6,946,000 B2 | 9/2005 | Senegas et al. |
| 6,949,100 B1 | 9/2005 | Venturini |
| 6,951,561 B2 | 10/2005 | Warren et al. |
| 6,952,129 B2 | 10/2005 | Lin et al. |
| 6,953,477 B2 | 10/2005 | Berry |
| 6,955,691 B2 | 10/2005 | Chae et al. |
| 6,962,606 B2 | 11/2005 | Michelson |
| 6,964,674 B1 | 11/2005 | Matsuura et al. |
| 6,964,686 B2 | 11/2005 | Gordon |
| 6,966,910 B2 | 11/2005 | Ritland |
| 6,969,404 B2 | 11/2005 | Ferree |
| 6,969,405 B2 | 11/2005 | Suddaby |
| D512,506 S | 12/2005 | Layne et al. |
| 6,972,019 B2 | 12/2005 | Michelson |
| 6,972,035 B2 | 12/2005 | Michelson |
| 6,974,479 B2 | 12/2005 | Trieu |
| 6,974,480 B2 | 12/2005 | Messerli et al. |
| 6,979,341 B2 | 12/2005 | Scribner et al. |
| 6,979,352 B2 | 12/2005 | Reynolds |
| 6,979,353 B2 | 12/2005 | Bresina |
| 6,981,981 B2 | 1/2006 | Reiley et al. |
| 6,984,234 B2 | 1/2006 | Bray |
| 6,997,929 B2 | 2/2006 | Manzi et al. |
| 7,001,385 B2 | 2/2006 | Bonutti |
| 7,004,945 B2 | 2/2006 | Boyd et al. |
| 7,004,971 B2 | 2/2006 | Serhan et al. |
| 7,008,431 B2 | 3/2006 | Simonson |
| 7,008,453 B1 | 3/2006 | Michelson |
| 7,014,633 B2 | 3/2006 | Cragg |
| 7,018,089 B2 | 3/2006 | Wenz et al. |
| 7,018,412 B2 | 3/2006 | Ferreira et al. |
| 7,018,415 B1 | 3/2006 | McKay |
| 7,018,416 B2 | 3/2006 | Hanson et al. |
| 7,018,453 B2 | 3/2006 | Klein et al. |
| 7,022,138 B2 | 4/2006 | Mashburn |
| 7,025,746 B2 | 4/2006 | Tal |
| 7,025,787 B2 | 4/2006 | Bryan et al. |
| 7,029,473 B2 | 4/2006 | Zucherman et al. |
| 7,029,498 B2 | 4/2006 | Boehm et al. |
| 7,033,394 B2 | 4/2006 | Michelson |
| 7,037,339 B2 | 5/2006 | Houfburg |
| 7,041,107 B2 | 5/2006 | Pohjonen et al. |
| 7,041,135 B2 | 5/2006 | Michelson |
| 7,044,954 B2 | 5/2006 | Reiley et al. |
| 7,044,971 B2 | 5/2006 | Suddaby |
| 7,048,694 B2 | 5/2006 | Mark et al. |
| 7,048,736 B2 | 5/2006 | Robinson et al. |
| 7,056,341 B2 | 6/2006 | Crozet |
| 7,060,068 B2 | 6/2006 | Tromanhauser et al. |
| 7,063,491 B2 | 6/2006 | French |
| 7,063,701 B2 | 6/2006 | Michelson |
| 7,063,702 B2 | 6/2006 | Michelson |
| 7,063,703 B2 | 6/2006 | Reo |
| 7,066,960 B1 | 6/2006 | Dickman |
| 7,066,961 B2 | 6/2006 | Michelson |
| 7,069,087 B2 | 6/2006 | Sharkey et al. |
| 7,070,598 B2 | 7/2006 | Lim et al. |
| 7,070,601 B2 | 7/2006 | Culbert et al. |
| 7,074,203 B1 | 7/2006 | Johanson et al. |
| 7,074,226 B2 | 7/2006 | Roehm et al. |
| 7,077,864 B2 | 7/2006 | Byrd et al. |
| 7,081,120 B2 | 7/2006 | Li et al. |
| 7,081,122 B1 | 7/2006 | Reiley et al. |
| 7,083,650 B2 | 8/2006 | Moskowitz et al. |
| 7,087,055 B2 | 8/2006 | Lim et al. |
| 7,087,083 B2 | 8/2006 | Pasquet et al. |
| 7,094,239 B1 | 8/2006 | Michelson |
| 7,094,257 B2 | 8/2006 | Mujwid et al. |
| 7,094,258 B2 | 8/2006 | Lambrecht et al. |
| 7,101,375 B2 | 9/2006 | Zucherman et al. |
| 7,112,222 B2 | 9/2006 | Fraser et al. |
| 7,112,223 B2 | 9/2006 | Davis |
| 7,114,501 B2 | 10/2006 | Johnson et al. |
| 7,115,128 B2 | 10/2006 | Michelson |
| 7,115,163 B2 | 10/2006 | Zimmermann |
| 7,118,572 B2 | 10/2006 | Bramlet et al. |
| 7,118,579 B2 | 10/2006 | Michelson |
| 7,118,580 B1 | 10/2006 | Beyersdorff et al. |
| 7,118,598 B2 | 10/2006 | Michelson |
| 7,124,761 B2 | 10/2006 | Lambrecht et al. |
| 7,128,744 B2 | 10/2006 | Weaver et al. |
| 7,128,760 B2 | 10/2006 | Michelson |
| 7,135,024 B2 | 11/2006 | Cook et al. |
| 7,135,043 B2 | 11/2006 | Nakahara et al. |
| 7,135,424 B2 | 11/2006 | Worley et al. |
| 7,153,304 B2 | 12/2006 | Robie et al. |
| 7,153,305 B2 | 12/2006 | Johnson et al. |
| 7,153,306 B2 | 12/2006 | Ralph et al. |
| 7,153,307 B2 | 12/2006 | Scribner et al. |
| D536,096 S | 1/2007 | Hoogland et al. |
| 7,156,874 B2 | 1/2007 | Paponneau et al. |
| 7,156,875 B2 | 1/2007 | Michelson |
| 7,156,876 B2 | 1/2007 | Moumene et al. |
| 7,163,558 B2 | 1/2007 | Senegas et al. |
| 7,163,561 B2 | 1/2007 | Michelson |
| 7,166,107 B2 | 1/2007 | Anderson |
| 7,172,612 B2 | 2/2007 | Ishikawa |
| 7,172,627 B2 | 2/2007 | Fiere et al. |
| 7,179,293 B2 | 2/2007 | McKay |
| 7,179,294 B2 | 2/2007 | Eisermann et al. |
| 7,189,242 B2 | 3/2007 | Boyd et al. |
| 7,201,751 B2 | 4/2007 | Zucherman et al. |
| 7,204,851 B2 | 4/2007 | Trieu et al. |
| 7,207,991 B2 | 4/2007 | Michelson |
| 7,211,112 B2 | 5/2007 | Baynham et al. |
| 7,214,227 B2 | 5/2007 | Colleran et al. |
| 7,217,291 B2 | 5/2007 | Zucherman et al. |
| 7,217,293 B2 | 5/2007 | Branch, Jr. |
| 7,220,280 B2 | 5/2007 | Kast et al. |
| 7,220,281 B2 | 5/2007 | Lambrecht et al. |
| 7,223,227 B2 | 5/2007 | Pflueger |
| 7,223,292 B2 | 5/2007 | Messerli et al. |
| 7,226,481 B2 | 6/2007 | Kuslich |
| 7,226,482 B2 | 6/2007 | Messerli et al. |
| 7,226,483 B2 | 6/2007 | Gerber et al. |
| 7,232,463 B2 | 6/2007 | Falahee |
| 7,232,464 B2 | 6/2007 | Mathieu et al. |
| 7,235,101 B2 | 6/2007 | Berry et al. |
| 7,237,424 B2 | 7/2007 | Crutchley |
| 7,238,203 B2 | 7/2007 | Bagga et al. |
| 7,238,204 B2 | 7/2007 | Le et al. |
| 7,238,206 B2 | 7/2007 | Lange et al. |
| 7,241,297 B2 | 7/2007 | Shaolian et al. |
| 7,244,273 B2 | 7/2007 | Pedersen et al. |
| 7,250,060 B2 | 7/2007 | Trieu |
| 7,252,671 B2 | 8/2007 | Scribner et al. |
| 7,255,698 B2 | 8/2007 | Michelson |
| 7,267,683 B2 | 9/2007 | Sharkey et al. |
| 7,267,687 B2 | 9/2007 | McGuckin, Jr. |
| 7,270,679 B2 | 9/2007 | Istephanous et al. |
| 7,276,062 B2 | 10/2007 | McDaniel et al. |
| 7,276,081 B1 | 10/2007 | Coates et al. |

(56) References Cited

U.S. PATENT DOCUMENTS

| | | |
|---|---|---|
| 7,282,061 B2 | 10/2007 | Sharkey et al. |
| 7,288,094 B2 | 10/2007 | Lindemann et al. |
| 7,288,095 B2 | 10/2007 | Baynham et al. |
| 7,288,114 B2 | 10/2007 | Lange |
| 7,291,173 B2 | 11/2007 | Richelsoph et al. |
| 7,300,440 B2 | 11/2007 | Zdeblick et al. |
| 7,306,605 B2 | 12/2007 | Ross |
| 7,306,628 B2 | 12/2007 | Zucherman et al. |
| 7,309,357 B2 | 12/2007 | Kim |
| 7,309,358 B2 | 12/2007 | Berry et al. |
| 7,311,713 B2 | 12/2007 | Johnson et al. |
| 7,311,734 B2 | 12/2007 | Van et al. |
| 7,316,714 B2 | 1/2008 | Gordon et al. |
| 7,318,839 B2 | 1/2008 | Malberg et al. |
| 7,318,840 B2 | 1/2008 | McKay |
| 7,320,689 B2 | 1/2008 | Keller |
| 7,320,708 B1 | 1/2008 | Bernstein |
| 7,322,962 B2 | 1/2008 | Forrest |
| 7,323,011 B2 | 1/2008 | Shepard et al. |
| 7,326,211 B2 | 2/2008 | Padget et al. |
| 7,326,248 B2 | 2/2008 | Michelson |
| 7,332,209 B2 | 2/2008 | Yokouchi et al. |
| 7,335,203 B2 | 2/2008 | Winslow et al. |
| 7,338,525 B2 | 3/2008 | Ferree |
| 7,341,413 B2 | 3/2008 | Morris et al. |
| 7,341,587 B2 | 3/2008 | Molz et al. |
| 7,341,589 B2 | 3/2008 | Weaver et al. |
| 7,341,590 B2 | 3/2008 | Ferree |
| 7,354,452 B2 | 4/2008 | Foley |
| 7,361,140 B2 | 4/2008 | Ries et al. |
| 7,361,193 B2 | 4/2008 | Frey et al. |
| 7,371,238 B2 | 5/2008 | Soboleski et al. |
| 7,377,942 B2 | 5/2008 | Berry |
| 7,383,639 B2 | 6/2008 | Malandain |
| 7,400,930 B2 | 7/2008 | Sharkey et al. |
| 7,410,501 B2 | 8/2008 | Michelson |
| 7,413,576 B2 | 8/2008 | Sybert et al. |
| 7,422,594 B2 | 9/2008 | Zander |
| 7,434,325 B2 | 10/2008 | Foley et al. |
| 7,435,262 B2 | 10/2008 | Michelson |
| 7,438,715 B2 | 10/2008 | Doubler et al. |
| 7,442,209 B2 | 10/2008 | Michelson |
| 7,442,211 B2 | 10/2008 | De et al. |
| 7,445,636 B2 | 11/2008 | Michelson |
| 7,445,637 B2 | 11/2008 | Taylor |
| 7,452,370 B2 | 11/2008 | Anderson |
| D584,812 S | 1/2009 | Ries |
| 7,473,256 B2 | 1/2009 | Assell et al. |
| 7,473,268 B2 | 1/2009 | Zucherman et al. |
| 7,473,568 B2 | 1/2009 | Co et al. |
| 7,476,251 B2 | 1/2009 | Zucherman et al. |
| 7,485,134 B2 | 2/2009 | Simonson |
| 7,485,135 B2 | 2/2009 | Steiger et al. |
| 7,488,326 B2 | 2/2009 | Elliott |
| 7,491,237 B2 | 2/2009 | Randall et al. |
| 7,500,991 B2 | 3/2009 | Bartish et al. |
| 7,503,920 B2 | 3/2009 | Siegal |
| 7,503,933 B2 | 3/2009 | Michelson |
| 7,507,241 B2 | 3/2009 | Levy et al. |
| 7,513,900 B2 | 4/2009 | Carrison et al. |
| 7,517,363 B2 | 4/2009 | Rogers et al. |
| 7,520,888 B2 | 4/2009 | Trieu |
| 7,527,641 B2 | 5/2009 | Suh |
| 7,547,317 B2 | 6/2009 | Cragg |
| 7,556,629 B2 | 7/2009 | Von et al. |
| 7,556,651 B2 | 7/2009 | Humphreys et al. |
| 7,569,054 B2 | 8/2009 | Michelson |
| 7,569,074 B2 | 8/2009 | Eisermann et al. |
| 7,575,599 B2 | 8/2009 | Villiers et al. |
| 7,588,574 B2 | 9/2009 | Assell et al. |
| 7,593,931 B2 | 9/2009 | Zuzarte et al. |
| 7,594,931 B2 | 9/2009 | Louis et al. |
| 7,594,932 B2 | 9/2009 | Aferzon et al. |
| 7,601,171 B2 | 10/2009 | Ainsworth et al. |
| 7,601,173 B2 | 10/2009 | Messerli et al. |
| 7,608,062 B2 | 10/2009 | Sweeney |
| 7,608,083 B2 | 10/2009 | Lee et al. |
| 7,618,456 B2 | 11/2009 | Mathieu et al. |
| 7,618,458 B2 | 11/2009 | Biedermann et al. |
| 7,621,950 B1 | 11/2009 | Globerman et al. |
| 7,621,960 B2 | 11/2009 | Boyd et al. |
| 7,625,378 B2 | 12/2009 | Foley |
| 7,628,816 B2 | 12/2009 | Magerl et al. |
| 7,637,905 B2 | 12/2009 | Saadat et al. |
| 7,637,949 B2 | 12/2009 | Hart |
| 7,641,657 B2 | 1/2010 | Cragg |
| 7,641,665 B2 | 1/2010 | Zubok et al. |
| 7,641,670 B2 | 1/2010 | Davison et al. |
| 7,641,692 B2 | 1/2010 | Bryan et al. |
| 7,647,123 B2 | 1/2010 | Sharkey et al. |
| 7,648,523 B2 | 1/2010 | Mirkovic et al. |
| 7,655,010 B2 | 2/2010 | Serhan et al. |
| 7,655,042 B2 | 2/2010 | Foley et al. |
| 7,658,766 B2 | 2/2010 | Melkent et al. |
| 7,662,182 B2 | 2/2010 | Zubok et al. |
| 7,666,266 B2 | 2/2010 | Izawa et al. |
| 7,670,354 B2 | 3/2010 | Davison et al. |
| 7,670,374 B2 | 3/2010 | Schaller |
| 7,674,273 B2 | 3/2010 | Davison et al. |
| 7,674,279 B2 | 3/2010 | Johnson |
| 7,682,370 B2 | 3/2010 | Pagliuca et al. |
| 7,691,120 B2 | 4/2010 | Shluzas et al. |
| 7,691,147 B2 | 4/2010 | Guetlin et al. |
| 7,699,878 B2 | 4/2010 | Pavlov et al. |
| 7,703,727 B2 | 4/2010 | Selness |
| 7,704,255 B2 | 4/2010 | Michelson |
| 7,717,944 B2 | 5/2010 | Foley et al. |
| 7,722,530 B2 | 5/2010 | Davison |
| 7,722,612 B2 | 5/2010 | Sala et al. |
| 7,722,674 B1 | 5/2010 | Grotz |
| 7,726,002 B2 | 6/2010 | Shimp et al. |
| 7,727,263 B2 | 6/2010 | Cragg |
| 7,740,633 B2 | 6/2010 | Assell et al. |
| 7,744,599 B2 | 6/2010 | Cragg |
| 7,744,650 B2 | 6/2010 | Lindner et al. |
| 7,749,270 B2 | 7/2010 | Peterman |
| 7,762,995 B2 | 7/2010 | Eversull et al. |
| 7,763,025 B2 | 7/2010 | Ainsworth |
| 7,763,055 B2 | 7/2010 | Foley |
| 7,766,930 B2 | 8/2010 | Dipoto et al. |
| 7,771,473 B2 | 8/2010 | Thramann |
| 7,771,479 B2 | 8/2010 | Humphreys et al. |
| 7,785,368 B2 | 8/2010 | Schaller |
| 7,789,914 B2 | 9/2010 | Michelson |
| 7,794,463 B2 | 9/2010 | Cragg |
| 7,794,502 B2 | 9/2010 | Michelson |
| 7,799,032 B2 | 9/2010 | Assell et al. |
| 7,799,033 B2 | 9/2010 | Assell et al. |
| 7,799,036 B2 | 9/2010 | Davison et al. |
| 7,799,080 B2 | 9/2010 | Doty |
| 7,799,081 B2 | 9/2010 | McKinley |
| 7,799,083 B2 | 9/2010 | Smith et al. |
| D626,233 S | 10/2010 | Cipoletti et al. |
| 7,814,429 B2 | 10/2010 | Buffet et al. |
| 7,815,643 B2 | 10/2010 | Johnson et al. |
| 7,815,681 B2 | 10/2010 | Ferguson |
| 7,819,921 B2 | 10/2010 | Grotz |
| 7,824,410 B2 | 11/2010 | Simonson et al. |
| 7,824,429 B2 | 11/2010 | Culbert et al. |
| 7,824,445 B2 | 11/2010 | Biro et al. |
| 7,828,807 B2 | 11/2010 | Lehuec et al. |
| 7,837,734 B2 | 11/2010 | Zucherman et al. |
| 7,846,106 B2 | 12/2010 | Andrews et al. |
| 7,846,183 B2 | 12/2010 | Blain |
| 7,846,206 B2 | 12/2010 | Oglaza et al. |
| 7,846,207 B2 | 12/2010 | Lechmann et al. |
| 7,846,210 B2 | 12/2010 | Perez-Cruet et al. |
| 7,850,695 B2 | 12/2010 | Pagliuca et al. |
| 7,850,733 B2 | 12/2010 | Baynham et al. |
| 7,854,766 B2 | 12/2010 | Moskowitz et al. |
| 7,857,832 B2 | 12/2010 | Culbert et al. |
| 7,857,840 B2 | 12/2010 | Krebs et al. |
| 7,862,590 B2 | 1/2011 | Lim et al. |
| 7,862,595 B2 | 1/2011 | Foley et al. |

(56) References Cited

U.S. PATENT DOCUMENTS

| | | |
|---|---|---|
| 7,862,616 B2 | 1/2011 | Lechmann et al. |
| 7,867,259 B2 | 1/2011 | Foley et al. |
| 7,871,441 B2 | 1/2011 | Eckman |
| 7,874,980 B2 | 1/2011 | Sonnenschein et al. |
| 7,875,062 B2 | 1/2011 | Lindemann et al. |
| 7,875,076 B2 | 1/2011 | Mathieu et al. |
| 7,875,077 B2 | 1/2011 | Humphreys et al. |
| 7,879,098 B1 | 2/2011 | Simmons, Jr. |
| 7,883,531 B2 | 2/2011 | De Coninck |
| 7,887,589 B2 | 2/2011 | Glenn et al. |
| 7,887,591 B2 | 2/2011 | Aebi et al. |
| 7,887,595 B1 | 2/2011 | Pimenta |
| 7,892,171 B2 | 2/2011 | Davison et al. |
| 7,892,249 B2 | 2/2011 | Davison et al. |
| 7,901,438 B2 | 3/2011 | Culbert et al. |
| 7,901,459 B2 | 3/2011 | Hodges et al. |
| 7,909,832 B2 | 3/2011 | Michelson |
| 7,909,870 B2 | 3/2011 | Kraus |
| 7,909,874 B2 | 3/2011 | Zielinski |
| 7,909,877 B2 | 3/2011 | Krueger et al. |
| 7,918,874 B2 | 4/2011 | Siegal |
| 7,922,729 B2 | 4/2011 | Michelson |
| 7,931,689 B2 | 4/2011 | Hochschuler et al. |
| 7,935,051 B2 | 5/2011 | Miles et al. |
| 7,938,832 B2 | 5/2011 | Culbert et al. |
| 7,942,903 B2 | 5/2011 | Moskowitz et al. |
| 7,947,078 B2 | 5/2011 | Siegal |
| 7,951,199 B2 | 5/2011 | Miller |
| 7,955,391 B2 | 6/2011 | Schaller |
| 7,959,675 B2 | 6/2011 | Gately |
| 7,963,993 B2 | 6/2011 | Schaller |
| 7,967,864 B2 | 6/2011 | Schaller |
| 7,967,865 B2 | 6/2011 | Schaller |
| 7,985,231 B2 | 7/2011 | Sankaran |
| 7,993,403 B2 | 8/2011 | Foley et al. |
| 7,998,176 B2 | 8/2011 | Culbert |
| 8,002,808 B2 | 8/2011 | Morrison et al. |
| 8,007,523 B2 | 8/2011 | Wagner et al. |
| 8,007,535 B2 | 8/2011 | Hudgins et al. |
| 8,021,424 B2 | 9/2011 | Beger et al. |
| 8,021,426 B2 | 9/2011 | Segal et al. |
| 8,025,697 B2 | 9/2011 | McClellan et al. |
| 8,034,109 B2 | 10/2011 | Zwirkoski |
| 8,043,381 B2 | 10/2011 | Hestad et al. |
| 8,052,754 B2 | 11/2011 | Froehlich |
| 8,057,544 B2 | 11/2011 | Schaller |
| 8,057,545 B2 | 11/2011 | Hughes et al. |
| 8,062,375 B2 | 11/2011 | Glerum et al. |
| 8,075,621 B2 | 12/2011 | Michelson |
| 8,097,036 B2 | 1/2012 | Cordaro et al. |
| 8,100,978 B2 | 1/2012 | Bass |
| 8,105,382 B2 | 1/2012 | Olmos et al. |
| 8,109,977 B2 | 2/2012 | Culbert et al. |
| 8,114,088 B2 | 2/2012 | Miller |
| 8,118,871 B2 | 2/2012 | Gordon |
| 8,128,700 B2 | 3/2012 | Delurio et al. |
| 8,133,232 B2 | 3/2012 | Levy et al. |
| 8,177,812 B2 | 5/2012 | Sankaran |
| 8,187,327 B2 | 5/2012 | Edidin et al. |
| 8,187,329 B2 | 5/2012 | Theofilos |
| 8,192,495 B2 | 6/2012 | Simpson et al. |
| 8,202,322 B2 | 6/2012 | Doty |
| 8,206,423 B2 | 6/2012 | Siegal |
| 8,216,312 B2 | 7/2012 | Gray |
| 8,216,314 B2 | 7/2012 | Richelsoph |
| 8,221,501 B2 | 7/2012 | Eisermann et al. |
| 8,221,502 B2 | 7/2012 | Branch, Jr. |
| 8,221,503 B2 | 7/2012 | Garcia et al. |
| 8,231,681 B2 | 7/2012 | Castleman et al. |
| 8,236,029 B2 | 8/2012 | Siegal |
| 8,236,058 B2 | 8/2012 | Fabian et al. |
| 8,240,358 B2 | 8/2012 | Lomax et al. |
| 8,241,328 B2 | 8/2012 | Siegal |
| 8,241,358 B2 | 8/2012 | Butler et al. |
| 8,241,361 B2 | 8/2012 | Link |
| 8,246,622 B2 | 8/2012 | Siegal et al. |
| 8,257,440 B2 | 9/2012 | Gordon et al. |
| 8,257,442 B2 | 9/2012 | Edie et al. |
| 8,262,666 B2 | 9/2012 | Baynham et al. |
| 8,262,736 B2 | 9/2012 | Michelson |
| 8,267,939 B2 | 9/2012 | Cipoletti et al. |
| 8,267,965 B2 | 9/2012 | Gimbel et al. |
| 8,273,128 B2 | 9/2012 | Oh et al. |
| 8,273,129 B2 | 9/2012 | Baynham et al. |
| 8,287,599 B2 | 10/2012 | McGuckin, Jr. |
| 8,292,959 B2 | 10/2012 | Webb et al. |
| 8,303,663 B2 | 11/2012 | Jimenez et al. |
| 8,317,866 B2 | 11/2012 | Palmatier et al. |
| 8,323,342 B2 | 12/2012 | Schwab |
| 8,323,345 B2 | 12/2012 | Sledge |
| 8,328,812 B2 | 12/2012 | Siegal et al. |
| 8,328,852 B2 | 12/2012 | Zehavi et al. |
| 8,336,559 B2 | 12/2012 | Kallabat et al. |
| 8,337,559 B2 | 12/2012 | Hansell et al. |
| 8,343,193 B2 | 1/2013 | Johnson et al. |
| 8,343,219 B2 | 1/2013 | Allain et al. |
| 8,349,015 B2 | 1/2013 | Bae et al. |
| 8,353,961 B2 | 1/2013 | McClintock et al. |
| 8,357,200 B2 | 1/2013 | Adl |
| 8,361,154 B2 | 1/2013 | Reo |
| 8,366,777 B2 | 2/2013 | Matthis et al. |
| 8,377,098 B2 | 2/2013 | Landry et al. |
| 8,377,133 B2 | 2/2013 | Yuan et al. |
| 8,382,842 B2 | 2/2013 | Greenhalgh et al. |
| 8,394,129 B2 | 3/2013 | Morgenstern et al. |
| 8,398,712 B2 | 3/2013 | De et al. |
| 8,398,713 B2 | 3/2013 | Weiman |
| 8,403,990 B2 | 3/2013 | Dryer et al. |
| 8,409,290 B2 | 4/2013 | Zamani et al. |
| 8,409,291 B2 | 4/2013 | Blackwell et al. |
| 8,414,650 B2 | 4/2013 | Bertele et al. |
| 8,435,298 B2 | 5/2013 | Weiman |
| 8,454,617 B2 | 6/2013 | Schaller et al. |
| 8,454,694 B2 | 6/2013 | Armstrong et al. |
| 8,454,698 B2 | 6/2013 | De et al. |
| 8,460,385 B1 | 6/2013 | Wensel |
| 8,460,387 B2 | 6/2013 | Theofilos |
| 8,465,524 B2 | 6/2013 | Siegal |
| 8,470,044 B2 | 6/2013 | Bertholet et al. |
| 8,480,715 B2 | 7/2013 | Gray |
| 8,480,742 B2 | 7/2013 | Pisharodi |
| 8,480,747 B2 | 7/2013 | Melkent et al. |
| 8,486,109 B2 | 7/2013 | Siegal |
| 8,486,148 B2 | 7/2013 | Butler et al. |
| 8,491,591 B2 | 7/2013 | Fuerderer |
| 8,491,657 B2 | 7/2013 | Attia et al. |
| 8,491,658 B1 | 7/2013 | Etminan |
| 8,491,659 B2 | 7/2013 | Weiman |
| 8,496,691 B2 | 7/2013 | Blain |
| 8,496,708 B2 | 7/2013 | Blain |
| 8,500,783 B2 | 8/2013 | Baynham |
| 8,506,635 B2 | 8/2013 | Palmatier et al. |
| 8,518,087 B2 | 8/2013 | Lopez et al. |
| 8,518,120 B2 | 8/2013 | Glerum et al. |
| 8,535,380 B2 | 9/2013 | Greenhalgh et al. |
| 8,540,769 B2 | 9/2013 | Janowski et al. |
| 8,545,567 B1 | 10/2013 | Krueger |
| 8,551,173 B2 | 10/2013 | Lechmann et al. |
| 8,551,175 B1 | 10/2013 | Wensel |
| 8,556,978 B2 | 10/2013 | Schaller |
| 8,556,979 B2 | 10/2013 | Glerum et al. |
| 8,562,651 B2 | 10/2013 | Metcalf et al. |
| 8,568,481 B2 | 10/2013 | Olmos et al. |
| 8,579,977 B2 | 11/2013 | Fabian |
| 8,579,981 B2 | 11/2013 | Lim et al. |
| 8,591,583 B2 | 11/2013 | Schaller et al. |
| 8,591,585 B2 | 11/2013 | McLaughlin et al. |
| 8,597,330 B2 | 12/2013 | Siegal |
| 8,597,333 B2 | 12/2013 | Morgenstern et al. |
| 8,597,360 B2 | 12/2013 | McLuen et al. |
| 8,603,168 B2 | 12/2013 | Gordon et al. |
| 8,603,170 B2 | 12/2013 | Cipoletti et al. |
| 8,603,177 B2 | 12/2013 | Gray |
| 8,610,091 B2 | 12/2013 | Matsumoto |

(56) References Cited

U.S. PATENT DOCUMENTS

| | | |
|---|---|---|
| 8,613,772 B2 | 12/2013 | Bray et al. |
| 8,617,245 B2 | 12/2013 | Brett |
| 8,623,091 B2 | 1/2014 | Suedkamp et al. |
| 8,628,576 B2 | 1/2014 | Triplett et al. |
| 8,628,578 B2 | 1/2014 | Miller et al. |
| 8,632,595 B2 | 1/2014 | Weiman |
| 8,641,764 B2 | 2/2014 | Gately |
| 8,641,765 B2 | 2/2014 | Muhanna |
| 8,663,329 B2 | 3/2014 | Ernst |
| 8,668,740 B2 | 3/2014 | Rhoda et al. |
| 8,672,977 B2 | 3/2014 | Siegal et al. |
| 8,679,183 B2 | 3/2014 | Glerum et al. |
| 8,685,095 B2 | 4/2014 | Miller et al. |
| 8,685,098 B2 | 4/2014 | Glerum et al. |
| 8,690,928 B1 | 4/2014 | Walkenhorst et al. |
| 8,690,948 B2 | 4/2014 | Armstrong et al. |
| 8,696,751 B2 | 4/2014 | Ashley et al. |
| 8,709,086 B2 | 4/2014 | Glerum |
| 8,715,351 B1 | 5/2014 | Pinto |
| 8,721,723 B2 | 5/2014 | Hansell et al. |
| 8,728,160 B2 | 5/2014 | Globerman et al. |
| 8,728,166 B2 | 5/2014 | Schwab |
| 8,747,443 B2 | 6/2014 | Aferzon |
| 8,753,398 B2 | 6/2014 | Gordon et al. |
| 8,758,439 B2 | 6/2014 | Linares |
| 8,758,441 B2 | 6/2014 | Hovda et al. |
| 8,764,806 B2 | 7/2014 | Abdou |
| 8,764,831 B2 | 7/2014 | Lechmann et al. |
| 8,771,360 B2 | 7/2014 | Jimenez et al. |
| 8,777,993 B2 | 7/2014 | Siegal et al. |
| 8,778,025 B2 | 7/2014 | Ragab et al. |
| 8,795,366 B2 | 8/2014 | Varela |
| 8,795,374 B2 | 8/2014 | Chee |
| 8,801,787 B2 | 8/2014 | Schaller |
| 8,801,792 B2 | 8/2014 | De et al. |
| 8,808,376 B2 | 8/2014 | Schaller |
| 8,821,555 B2 | 9/2014 | Bae et al. |
| 8,828,085 B1 | 9/2014 | Jensen |
| 8,845,638 B2 | 9/2014 | Siegal et al. |
| 8,845,728 B1 | 9/2014 | Abdou |
| 8,845,731 B2 | 9/2014 | Weiman |
| 8,845,732 B2 | 9/2014 | Weiman |
| 8,845,734 B2 | 9/2014 | Weiman |
| 8,852,242 B2 | 10/2014 | Morgenstern et al. |
| 8,852,243 B2 | 10/2014 | Morgenstern et al. |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,894,711 B2 | 11/2014 | Varela |
| 8,900,235 B2 | 12/2014 | Siegal |
| 8,900,307 B2 | 12/2014 | Hawkins et al. |
| 8,906,098 B2 | 12/2014 | Siegal |
| 8,926,704 B2 | 1/2015 | Glerum et al. |
| 8,932,358 B1 | 1/2015 | Nehls |
| 8,932,359 B2 | 1/2015 | Brett |
| 8,936,641 B2 | 1/2015 | Cain |
| 8,940,052 B2 | 1/2015 | Lechmann et al. |
| 8,956,416 B2 | 2/2015 | McCarthy |
| 8,961,609 B2 | 2/2015 | Schaller |
| 8,974,508 B2 | 3/2015 | Stephan et al. |
| 8,979,860 B2 | 3/2015 | Voellmicke et al. |
| 8,979,929 B2 | 3/2015 | Schaller |
| 8,986,387 B1 | 3/2015 | To et al. |
| 8,986,388 B2 | 3/2015 | Siegal et al. |
| 9,005,291 B2 | 4/2015 | Loebl et al. |
| 9,005,293 B2 | 4/2015 | Moskowitz et al. |
| 9,005,295 B2 | 4/2015 | Kueenzi et al. |
| 9,017,408 B2 | 4/2015 | Siegal et al. |
| 9,017,413 B2 | 4/2015 | Siegal et al. |
| 9,039,767 B2 | 5/2015 | Raymond et al. |
| 9,039,768 B2 | 5/2015 | Voellmicke |
| 9,039,771 B2 | 5/2015 | Glerum et al. |
| 9,044,334 B2 | 6/2015 | Siegal et al. |
| 9,044,338 B2 | 6/2015 | Schaller |
| 9,060,876 B1 | 6/2015 | To et al. |
| 9,066,808 B2 | 6/2015 | Schaller |
| 9,078,767 B1 | 7/2015 | McLean |
| 9,089,428 B2 | 7/2015 | Bertele et al. |
| 9,095,446 B2 | 8/2015 | Landry et al. |
| 9,095,447 B2 | 8/2015 | Barreiro et al. |
| 9,101,488 B2 | 8/2015 | Malandain |
| 9,101,489 B2 | 8/2015 | Protopsaltis et al. |
| 9,107,766 B1 | 8/2015 | McLean et al. |
| 9,138,330 B2 | 9/2015 | Hansell et al. |
| 9,192,419 B2 | 11/2015 | McDonough et al. |
| 9,248,028 B2 | 2/2016 | Gamache |
| 9,254,138 B2 | 2/2016 | Siegal et al. |
| 9,259,326 B2 | 2/2016 | Schaller |
| 9,265,261 B2 | 2/2016 | Haas et al. |
| 9,265,546 B2 | 2/2016 | Blain |
| 9,265,621 B2 | 2/2016 | Voellmicke |
| 9,271,836 B2 | 3/2016 | Pavento et al. |
| 9,277,928 B2 | 3/2016 | Morgenstern Lopez |
| 9,278,009 B2 | 3/2016 | Bray et al. |
| 9,283,091 B2 | 3/2016 | Melkent et al. |
| 9,283,092 B2 | 3/2016 | Siegal et al. |
| 9,289,311 B1 | 3/2016 | Whipple |
| 9,295,562 B2 | 3/2016 | Lechmann et al. |
| 9,320,610 B2 | 4/2016 | Alheidt et al. |
| 9,320,615 B2 | 4/2016 | Suedkamp et al. |
| 9,326,866 B2 | 5/2016 | Schaller et al. |
| 9,333,091 B2 | 5/2016 | Dimauro |
| 9,364,272 B2 | 6/2016 | Binder et al. |
| 9,387,087 B2 | 7/2016 | Tyber |
| 9,402,735 B2 | 8/2016 | McDonough et al. |
| 9,402,738 B2 | 8/2016 | Niemiec et al. |
| 9,402,739 B2 | 8/2016 | Ineiman et al. |
| 9,408,712 B2 | 8/2016 | Siegal et al. |
| 9,414,923 B2 | 8/2016 | Studer et al. |
| 9,414,934 B2 | 8/2016 | Cain |
| 9,433,510 B2 | 9/2016 | Lechmann et al. |
| 9,439,776 B2 | 9/2016 | Dimauro et al. |
| 9,439,777 B2 | 9/2016 | Dimauro |
| 9,445,918 B1 | 9/2016 | Lin et al. |
| 9,463,099 B2 | 10/2016 | Levy et al. |
| 9,492,286 B2 | 11/2016 | Biedermann et al. |
| 9,492,288 B2 | 11/2016 | Wagner et al. |
| 9,510,954 B2 | 12/2016 | Glerum et al. |
| 9,522,070 B2 | 12/2016 | Flower et al. |
| 9,566,165 B2 | 2/2017 | Lee et al. |
| 9,592,129 B2 | 3/2017 | Slivka et al. |
| 9,597,197 B2 | 3/2017 | Lechmann et al. |
| 9,662,225 B2 | 5/2017 | Pavento et al. |
| 9,668,877 B2 | 6/2017 | Pavento et al. |
| 9,724,207 B2 | 8/2017 | Dimauro et al. |
| 9,730,803 B2 | 8/2017 | Dimauro et al. |
| 9,788,963 B2 | 10/2017 | Aquino et al. |
| 9,801,729 B2 | 10/2017 | Dimauro et al. |
| 9,808,351 B2 | 11/2017 | Kelly et al. |
| 9,814,589 B2 | 11/2017 | Dimauro |
| 9,814,590 B2 | 11/2017 | Serhan et al. |
| 9,833,334 B2 | 12/2017 | Voellmicke et al. |
| 9,848,992 B2 | 12/2017 | Mcdonough et al. |
| 9,867,718 B2 | 1/2018 | Schmura et al. |
| 9,895,236 B2 | 2/2018 | Voellmicke et al. |
| 9,918,851 B2 | 3/2018 | Willis et al. |
| 9,925,060 B2 | 3/2018 | Dimauro et al. |
| 9,949,769 B2 | 4/2018 | Serhan et al. |
| 9,987,142 B2 | 6/2018 | McConnell |
| 10,085,843 B2 | 10/2018 | Dimauro |
| 10,238,500 B2 | 3/2019 | Rogers et al. |
| 10,307,254 B2 | 6/2019 | Levy et al. |
| 10,376,372 B2 | 8/2019 | Serhan et al. |
| 10,398,563 B2 | 9/2019 | Engstrom |
| 10,405,986 B2 | 9/2019 | Kelly et al. |
| 10,420,651 B2 | 9/2019 | Serhan et al. |
| 10,433,971 B2 | 10/2019 | Dimauro et al. |
| 10,433,974 B2 | 10/2019 | O'Neil |
| 10,492,918 B2 | 12/2019 | Dimauro |
| 10,512,489 B2 | 12/2019 | Serhan et al. |
| 10,555,817 B2 | 2/2020 | Dimauro et al. |
| 10,575,959 B2 | 3/2020 | Dimauro et al. |
| 10,583,013 B2 | 3/2020 | Dimauro et al. |

(56) References Cited

U.S. PATENT DOCUMENTS

| | | |
|---|---|---|
| 10,639,164 B2 | 5/2020 | Dimauro et al. |
| 2001/0005475 A1 | 6/2001 | Frigg |
| 2001/0011174 A1 | 8/2001 | Reiley et al. |
| 2001/0012950 A1 | 8/2001 | Nishtala et al. |
| 2001/0016741 A1 | 8/2001 | Burkus et al. |
| 2001/0027320 A1 | 10/2001 | Sasso |
| 2001/0031968 A1 | 10/2001 | Dorchak et al. |
| 2001/0032020 A1 | 10/2001 | Besselink |
| 2001/0037126 A1 | 11/2001 | Stack et al. |
| 2001/0039452 A1 | 11/2001 | Zucherman et al. |
| 2001/0039453 A1 | 11/2001 | Gresser et al. |
| 2001/0049529 A1 | 12/2001 | Cachia et al. |
| 2001/0049530 A1 | 12/2001 | Culbert et al. |
| 2001/0049531 A1 | 12/2001 | Reiley et al. |
| 2001/0056302 A1 | 12/2001 | Boyer et al. |
| 2002/0001476 A1 | 1/2002 | Nagamine et al. |
| 2002/0010070 A1 | 1/2002 | Cales et al. |
| 2002/0016583 A1 | 2/2002 | Cragg |
| 2002/0026195 A1 | 2/2002 | Layne et al. |
| 2002/0026244 A1 | 2/2002 | Trieu |
| 2002/0029044 A1 | 3/2002 | Monassevitch et al. |
| 2002/0029082 A1 | 3/2002 | Muhanna |
| 2002/0029084 A1 | 3/2002 | Paul et al. |
| 2002/0032462 A1 | 3/2002 | Houser et al. |
| 2002/0032483 A1 | 3/2002 | Nicholson et al. |
| 2002/0035400 A1 | 3/2002 | Bryan et al. |
| 2002/0037799 A1 | 3/2002 | Li et al. |
| 2002/0045904 A1 | 4/2002 | Fuss et al. |
| 2002/0045942 A1 | 4/2002 | Ham |
| 2002/0055740 A1 | 5/2002 | Lieberman |
| 2002/0055781 A1 | 5/2002 | Sazy |
| 2002/0058947 A1 | 5/2002 | Hochschuler et al. |
| 2002/0068974 A1 | 6/2002 | Kuslich et al. |
| 2002/0068976 A1 | 6/2002 | Jackson |
| 2002/0068977 A1 | 6/2002 | Jackson |
| 2002/0077700 A1 | 6/2002 | Varga et al. |
| 2002/0077701 A1 | 6/2002 | Kuslich |
| 2002/0082584 A1 | 6/2002 | Rosenman et al. |
| 2002/0082608 A1 | 6/2002 | Reiley et al. |
| 2002/0087152 A1 | 7/2002 | Mikus et al. |
| 2002/0087163 A1 | 7/2002 | Dixon et al. |
| 2002/0091387 A1 | 7/2002 | Hoogland |
| 2002/0091390 A1 | 7/2002 | Michelson |
| 2002/0095155 A1 | 7/2002 | Michelson |
| 2002/0099376 A1 | 7/2002 | Michelson |
| 2002/0099385 A1 | 7/2002 | Ralph et al. |
| 2002/0107519 A1 | 8/2002 | Dixon et al. |
| 2002/0107573 A1 | 8/2002 | Steinberg |
| 2002/0120335 A1 | 8/2002 | Angelucci et al. |
| 2002/0128713 A1 | 9/2002 | Ferree |
| 2002/0128715 A1 | 9/2002 | Bryan et al. |
| 2002/0128716 A1 | 9/2002 | Cohen et al. |
| 2002/0138146 A1 | 9/2002 | Jackson |
| 2002/0143328 A1 | 10/2002 | Shluzas et al. |
| 2002/0143331 A1 | 10/2002 | Zucherman et al. |
| 2002/0143334 A1 | 10/2002 | Hoffmann et al. |
| 2002/0143335 A1 | 10/2002 | Von et al. |
| 2002/0151895 A1 | 10/2002 | Soboleski et al. |
| 2002/0151976 A1 | 10/2002 | Foley et al. |
| 2002/0156475 A1 | 10/2002 | Lerch et al. |
| 2002/0156482 A1 | 10/2002 | Scribner et al. |
| 2002/0161444 A1 | 10/2002 | Choi |
| 2002/0165612 A1 | 11/2002 | Gerber et al. |
| 2002/0169471 A1 | 11/2002 | Ferdinand |
| 2002/0172851 A1 | 11/2002 | Corey et al. |
| 2002/0173796 A1 | 11/2002 | Cragg |
| 2002/0173841 A1 | 11/2002 | Ortiz et al. |
| 2002/0173851 A1 | 11/2002 | McKay |
| 2002/0183761 A1 | 12/2002 | Johnson et al. |
| 2002/0183778 A1 | 12/2002 | Reiley et al. |
| 2002/0183848 A1 | 12/2002 | Ray et al. |
| 2002/0191487 A1 | 12/2002 | Sand |
| 2002/0193883 A1 | 12/2002 | Wironen |
| 2002/0198526 A1 | 12/2002 | Shaolian et al. |
| 2003/0004575 A1 | 1/2003 | Erickson |
| 2003/0004576 A1 | 1/2003 | Thalgott |
| 2003/0006942 A1 | 1/2003 | Searls et al. |
| 2003/0014112 A1 | 1/2003 | Ralph et al. |
| 2003/0014116 A1 | 1/2003 | Ralph et al. |
| 2003/0018390 A1 | 1/2003 | Husson |
| 2003/0023305 A1 | 1/2003 | McKay |
| 2003/0028197 A1 | 2/2003 | Hanson et al. |
| 2003/0028250 A1 | 2/2003 | Reiley et al. |
| 2003/0028251 A1 | 2/2003 | Mathews |
| 2003/0032963 A1 | 2/2003 | Reiss et al. |
| 2003/0040796 A1 | 2/2003 | Ferree |
| 2003/0040799 A1 | 2/2003 | Boyd et al. |
| 2003/0045937 A1 | 3/2003 | Ginn |
| 2003/0045939 A1 | 3/2003 | Casutt |
| 2003/0045940 A1 | 3/2003 | Eberlein et al. |
| 2003/0050644 A1 | 3/2003 | Boucher et al. |
| 2003/0050645 A1 | 3/2003 | Parker et al. |
| 2003/0063582 A1 | 4/2003 | Mizell et al. |
| 2003/0065330 A1 | 4/2003 | Zucherman et al. |
| 2003/0065396 A1 | 4/2003 | Michelson |
| 2003/0069582 A1 | 4/2003 | Culbert |
| 2003/0069593 A1 | 4/2003 | Tremulis et al. |
| 2003/0069642 A1 | 4/2003 | Ralph et al. |
| 2003/0073998 A1 | 4/2003 | Pagliuca et al. |
| 2003/0074063 A1 | 4/2003 | Gerbec et al. |
| 2003/0074075 A1 | 4/2003 | Thomas et al. |
| 2003/0078667 A1 | 4/2003 | Manasas et al. |
| 2003/0083642 A1 | 5/2003 | Boyd et al. |
| 2003/0083688 A1 | 5/2003 | Simonson |
| 2003/0083748 A1 | 5/2003 | Lee et al. |
| 2003/0100949 A1 | 5/2003 | Michelson |
| 2003/0108588 A1 | 6/2003 | Chen et al. |
| 2003/0125739 A1 | 7/2003 | Bagga et al. |
| 2003/0130664 A1 | 7/2003 | Boucher et al. |
| 2003/0130739 A1 | 7/2003 | Gerbec et al. |
| 2003/0135275 A1 | 7/2003 | Garcia et al. |
| 2003/0139648 A1 | 7/2003 | Foley et al. |
| 2003/0139812 A1 | 7/2003 | Garcia et al. |
| 2003/0139813 A1 | 7/2003 | Messerli et al. |
| 2003/0153874 A1 | 8/2003 | Tal |
| 2003/0153975 A1 | 8/2003 | Byrd et al. |
| 2003/0158555 A1 | 8/2003 | Sanders et al. |
| 2003/0171812 A1 | 9/2003 | Grunberg et al. |
| 2003/0187431 A1 | 10/2003 | Simonson |
| 2003/0187440 A1 | 10/2003 | Richelsoph et al. |
| 2003/0187445 A1 | 10/2003 | Keith et al. |
| 2003/0187506 A1 | 10/2003 | Ross et al. |
| 2003/0191414 A1 | 10/2003 | Reiley et al. |
| 2003/0191489 A1 | 10/2003 | Reiley et al. |
| 2003/0195518 A1 | 10/2003 | Cragg |
| 2003/0195547 A1 | 10/2003 | Scribner et al. |
| 2003/0195630 A1 | 10/2003 | Ferree |
| 2003/0195632 A1 | 10/2003 | Foley et al. |
| 2003/0199979 A1 | 10/2003 | McGuckin |
| 2003/0204261 A1 | 10/2003 | Eisermann et al. |
| 2003/0208122 A1 | 11/2003 | Melkent et al. |
| 2003/0208136 A1 | 11/2003 | Mark et al. |
| 2003/0208203 A1 | 11/2003 | Lim et al. |
| 2003/0208220 A1 | 11/2003 | Worley et al. |
| 2003/0215344 A1 | 11/2003 | Condon et al. |
| 2003/0220643 A1 | 11/2003 | Ferree |
| 2003/0220648 A1 | 11/2003 | Osorio et al. |
| 2003/0220695 A1 | 11/2003 | Sevrain |
| 2003/0225409 A1 | 12/2003 | Freid et al. |
| 2003/0229350 A1 | 12/2003 | Kay |
| 2003/0229372 A1 | 12/2003 | Reiley et al. |
| 2003/0233096 A1 | 12/2003 | Osorio et al. |
| 2003/0233102 A1 | 12/2003 | Nakamura et al. |
| 2003/0233145 A1 | 12/2003 | Landry et al. |
| 2003/0233146 A1 | 12/2003 | Grinberg et al. |
| 2004/0002761 A1 | 1/2004 | Rogers et al. |
| 2004/0006391 A1 | 1/2004 | Reiley |
| 2004/0008949 A1 | 1/2004 | Liu et al. |
| 2004/0010251 A1 | 1/2004 | Pitaru et al. |
| 2004/0010260 A1 | 1/2004 | Scribner et al. |
| 2004/0010263 A1 | 1/2004 | Boucher et al. |
| 2004/0010318 A1 | 1/2004 | Ferree |
| 2004/0019354 A1 | 1/2004 | Johnson et al. |
| 2004/0019359 A1 | 1/2004 | Worley et al. |

(56) References Cited

U.S. PATENT DOCUMENTS

| | | |
|---|---|---|
| 2004/0024408 A1 | 2/2004 | Burkus et al. |
| 2004/0024409 A1 | 2/2004 | Sand et al. |
| 2004/0024410 A1 | 2/2004 | Olson et al. |
| 2004/0024463 A1 | 2/2004 | Thomas et al. |
| 2004/0024464 A1 | 2/2004 | Errico et al. |
| 2004/0024465 A1 | 2/2004 | Lambrecht et al. |
| 2004/0030387 A1 | 2/2004 | Landry et al. |
| 2004/0034343 A1 | 2/2004 | Gillespie et al. |
| 2004/0034429 A1 | 2/2004 | Lambrecht et al. |
| 2004/0034430 A1 | 2/2004 | Falahee |
| 2004/0049190 A1 | 3/2004 | Biedermann et al. |
| 2004/0049203 A1 | 3/2004 | Scribner et al. |
| 2004/0049223 A1 | 3/2004 | Nishtala et al. |
| 2004/0049270 A1 | 3/2004 | Gewirtz |
| 2004/0054412 A1 | 3/2004 | Gerbec et al. |
| 2004/0059333 A1 | 3/2004 | Carl et al. |
| 2004/0059339 A1 | 3/2004 | Roehm et al. |
| 2004/0059350 A1 | 3/2004 | Gordon et al. |
| 2004/0059418 A1 | 3/2004 | McKay et al. |
| 2004/0064144 A1 | 4/2004 | Johnson et al. |
| 2004/0073213 A1 | 4/2004 | Serhan et al. |
| 2004/0073308 A1 | 4/2004 | Kuslich et al. |
| 2004/0073310 A1 | 4/2004 | Moumene et al. |
| 2004/0082953 A1 | 4/2004 | Petit |
| 2004/0087947 A1 | 5/2004 | Lim et al. |
| 2004/0088055 A1 | 5/2004 | Hanson et al. |
| 2004/0092929 A1 | 5/2004 | Zindrick |
| 2004/0092933 A1 | 5/2004 | Shaolian et al. |
| 2004/0092948 A1 | 5/2004 | Stevens et al. |
| 2004/0092988 A1 | 5/2004 | Shaolian et al. |
| 2004/0093083 A1 | 5/2004 | Branch et al. |
| 2004/0097924 A1 | 5/2004 | Lambrecht et al. |
| 2004/0097930 A1 | 5/2004 | Justis et al. |
| 2004/0097932 A1 | 5/2004 | Ray et al. |
| 2004/0097941 A1 | 5/2004 | Weiner et al. |
| 2004/0097973 A1 | 5/2004 | Loshakove et al. |
| 2004/0098131 A1 | 5/2004 | Bryan et al. |
| 2004/0102774 A1 | 5/2004 | Trieu |
| 2004/0106925 A1 | 6/2004 | Culbert |
| 2004/0106940 A1 | 6/2004 | Shaolian et al. |
| 2004/0106996 A1 | 6/2004 | Liu et al. |
| 2004/0111089 A1 | 6/2004 | Stevens et al. |
| 2004/0111161 A1 | 6/2004 | Trieu |
| 2004/0116997 A1 | 6/2004 | Taylor et al. |
| 2004/0117019 A1 | 6/2004 | Trieu et al. |
| 2004/0117022 A1 | 6/2004 | Marnay et al. |
| 2004/0127902 A1 | 7/2004 | Suzuki et al. |
| 2004/0127906 A1 | 7/2004 | Culbert et al. |
| 2004/0127990 A1 | 7/2004 | Bartish et al. |
| 2004/0127991 A1 | 7/2004 | Ferree |
| 2004/0133124 A1 | 7/2004 | Bates et al. |
| 2004/0133229 A1 | 7/2004 | Lambrecht et al. |
| 2004/0133279 A1 | 7/2004 | Krueger et al. |
| 2004/0133280 A1 | 7/2004 | Trieu |
| 2004/0138662 A1 | 7/2004 | Landry et al. |
| 2004/0138748 A1 | 7/2004 | Boyer et al. |
| 2004/0143284 A1 | 7/2004 | Chin |
| 2004/0143332 A1 | 7/2004 | Krueger et al. |
| 2004/0143734 A1 | 7/2004 | Buer et al. |
| 2004/0147877 A1 | 7/2004 | Heuser |
| 2004/0147950 A1 | 7/2004 | Mueller et al. |
| 2004/0148027 A1 | 7/2004 | Errico et al. |
| 2004/0153064 A1 | 8/2004 | Foley et al. |
| 2004/0153065 A1 | 8/2004 | Lim |
| 2004/0153072 A1 | 8/2004 | Bonutti |
| 2004/0153115 A1 | 8/2004 | Reiley et al. |
| 2004/0153156 A1 | 8/2004 | Cohen et al. |
| 2004/0153160 A1 | 8/2004 | Carrasco |
| 2004/0158206 A1 | 8/2004 | Aboul-Hosn et al. |
| 2004/0158258 A1 | 8/2004 | Bonati et al. |
| 2004/0162617 A1 | 8/2004 | Zucherman et al. |
| 2004/0162618 A1 | 8/2004 | Mujwid et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0172133 A1 | 9/2004 | Gerber et al. |
| 2004/0172134 A1 | 9/2004 | Berry |
| 2004/0176775 A1 | 9/2004 | Burkus et al. |
| 2004/0186052 A1 | 9/2004 | Iyer et al. |
| 2004/0186471 A1 | 9/2004 | Trieu |
| 2004/0186482 A1 | 9/2004 | Kolb et al. |
| 2004/0186528 A1 | 9/2004 | Ries et al. |
| 2004/0186570 A1 | 9/2004 | Rapp |
| 2004/0186573 A1 | 9/2004 | Ferree |
| 2004/0186577 A1 | 9/2004 | Ferree |
| 2004/0193269 A1 | 9/2004 | Fraser et al. |
| 2004/0193277 A1 | 9/2004 | Long et al. |
| 2004/0199162 A1 | 10/2004 | Von et al. |
| 2004/0199253 A1 | 10/2004 | Link et al. |
| 2004/0199254 A1 | 10/2004 | Louis et al. |
| 2004/0210219 A1 | 10/2004 | Bray |
| 2004/0210231 A1 | 10/2004 | Boucher et al. |
| 2004/0210310 A1 | 10/2004 | Trieu |
| 2004/0215343 A1 | 10/2004 | Hochschuler et al. |
| 2004/0215344 A1 | 10/2004 | Hochschuler et al. |
| 2004/0220580 A1 | 11/2004 | Johnson et al. |
| 2004/0220669 A1 | 11/2004 | Studer |
| 2004/0220672 A1 | 11/2004 | Shadduck |
| 2004/0225292 A1 | 11/2004 | Sasso et al. |
| 2004/0225296 A1 | 11/2004 | Reiss et al. |
| 2004/0225361 A1 | 11/2004 | Glenn et al. |
| 2004/0230191 A1 | 11/2004 | Frey et al. |
| 2004/0230309 A1 | 11/2004 | Dimauro et al. |
| 2004/0243229 A1 | 12/2004 | Vidlund et al. |
| 2004/0243239 A1 | 12/2004 | Taylor |
| 2004/0243241 A1 | 12/2004 | Istephanous et al. |
| 2004/0249377 A1 | 12/2004 | Kaes et al. |
| 2004/0249466 A1 | 12/2004 | Liu et al. |
| 2004/0254520 A1 | 12/2004 | Porteous et al. |
| 2004/0254575 A1 | 12/2004 | Obenchain et al. |
| 2004/0254644 A1 | 12/2004 | Taylor |
| 2004/0260286 A1 | 12/2004 | Ferree |
| 2004/0260297 A1 | 12/2004 | Padget et al. |
| 2004/0260300 A1 | 12/2004 | Gorensek et al. |
| 2004/0260397 A1 | 12/2004 | Lambrecht et al. |
| 2004/0266257 A1 | 12/2004 | Ries et al. |
| 2004/0267271 A9 | 12/2004 | Scribner et al. |
| 2004/0267367 A1 | 12/2004 | O'Neil |
| 2005/0004578 A1 | 1/2005 | Lambrecht et al. |
| 2005/0010292 A1 | 1/2005 | Carrasco |
| 2005/0010293 A1 | 1/2005 | Zucherman et al. |
| 2005/0010298 A1 | 1/2005 | Zucherman et al. |
| 2005/0015147 A1 | 1/2005 | Schwardt et al. |
| 2005/0015148 A1 | 1/2005 | Jansen et al. |
| 2005/0015152 A1 | 1/2005 | Sweeney |
| 2005/0019365 A1 | 1/2005 | Frauchiger et al. |
| 2005/0021041 A1 | 1/2005 | Michelson |
| 2005/0021144 A1 | 1/2005 | Malberg et al. |
| 2005/0033289 A1 | 2/2005 | Warren et al. |
| 2005/0033295 A1 | 2/2005 | Wisnewski |
| 2005/0033433 A1 | 2/2005 | Michelson |
| 2005/0033434 A1 | 2/2005 | Berry |
| 2005/0033440 A1 | 2/2005 | Lambrecht et al. |
| 2005/0038513 A1 | 2/2005 | Michelson |
| 2005/0038515 A1 | 2/2005 | Kunzler |
| 2005/0038517 A1 | 2/2005 | Carrison et al. |
| 2005/0043737 A1 | 2/2005 | Reiley et al. |
| 2005/0043796 A1 | 2/2005 | Grant et al. |
| 2005/0043800 A1 | 2/2005 | Paul et al. |
| 2005/0054948 A1 | 3/2005 | Goldenberg |
| 2005/0055097 A1 | 3/2005 | Grunberg et al. |
| 2005/0060036 A1 | 3/2005 | Schultz et al. |
| 2005/0060038 A1 | 3/2005 | Lambrecht et al. |
| 2005/0065519 A1 | 3/2005 | Michelson |
| 2005/0065608 A1 | 3/2005 | Michelson |
| 2005/0065609 A1 | 3/2005 | Wardlaw |
| 2005/0065610 A1 | 3/2005 | Pisharodi |
| 2005/0069571 A1 | 3/2005 | Slivka et al. |
| 2005/0070908 A1 | 3/2005 | Cragg |
| 2005/0070911 A1 | 3/2005 | Carrison et al. |
| 2005/0070913 A1 | 3/2005 | Milbocker et al. |
| 2005/0071006 A1 | 3/2005 | Kirschman |
| 2005/0071008 A1 | 3/2005 | Kirschman |
| 2005/0071011 A1 | 3/2005 | Ralph et al. |

(56) References Cited

U.S. PATENT DOCUMENTS

| | | |
|---|---|---|
| 2005/0080488 A1 | 4/2005 | Schultz |
| 2005/0085912 A1 | 4/2005 | Arnin et al. |
| 2005/0085913 A1 | 4/2005 | Fraser et al. |
| 2005/0090443 A1 | 4/2005 | Michael John |
| 2005/0090833 A1 | 4/2005 | Dipoto |
| 2005/0090852 A1 | 4/2005 | Layne et al. |
| 2005/0090899 A1 | 4/2005 | Dipoto |
| 2005/0096657 A1 | 5/2005 | Autericque et al. |
| 2005/0101960 A1 | 5/2005 | Fiere et al. |
| 2005/0102202 A1 | 5/2005 | Linden et al. |
| 2005/0107880 A1 | 5/2005 | Shimp et al. |
| 2005/0113916 A1 | 5/2005 | Branch, Jr. |
| 2005/0113917 A1 | 5/2005 | Chae et al. |
| 2005/0113918 A1 | 5/2005 | Messerli et al. |
| 2005/0113919 A1 | 5/2005 | Cragg et al. |
| 2005/0113920 A1 | 5/2005 | Foley et al. |
| 2005/0113927 A1 | 5/2005 | Malek |
| 2005/0113928 A1 | 5/2005 | Cragg et al. |
| 2005/0118228 A1 | 6/2005 | Trieu |
| 2005/0118550 A1 | 6/2005 | Turri |
| 2005/0119657 A1 | 6/2005 | Goldsmith |
| 2005/0119662 A1 | 6/2005 | Reiley et al. |
| 2005/0119750 A1 | 6/2005 | Studer |
| 2005/0119751 A1 | 6/2005 | Lawson |
| 2005/0119752 A1 | 6/2005 | Williams et al. |
| 2005/0119754 A1 | 6/2005 | Trieu et al. |
| 2005/0124989 A1 | 6/2005 | Suddaby |
| 2005/0124992 A1 | 6/2005 | Ferree |
| 2005/0124999 A1 | 6/2005 | Teitelbaum et al. |
| 2005/0125062 A1 | 6/2005 | Biedermann et al. |
| 2005/0125066 A1 | 6/2005 | McAfee |
| 2005/0130929 A1 | 6/2005 | Boyd |
| 2005/0131267 A1 | 6/2005 | Talmadge |
| 2005/0131268 A1 | 6/2005 | Talmadge |
| 2005/0131269 A1 | 6/2005 | Talmadge |
| 2005/0131406 A1 | 6/2005 | Reiley et al. |
| 2005/0131409 A1 | 6/2005 | Chervitz et al. |
| 2005/0131411 A1 | 6/2005 | Culbert |
| 2005/0131536 A1 | 6/2005 | Eisermann et al. |
| 2005/0131538 A1 | 6/2005 | Chervitz et al. |
| 2005/0131540 A1 | 6/2005 | Trieu |
| 2005/0131541 A1 | 6/2005 | Trieu |
| 2005/0137595 A1 | 6/2005 | Hoffmann et al. |
| 2005/0137602 A1 | 6/2005 | Assell et al. |
| 2005/0142211 A1 | 6/2005 | Wenz |
| 2005/0143734 A1 | 6/2005 | Cachia et al. |
| 2005/0143749 A1 | 6/2005 | Zalenski et al. |
| 2005/0143763 A1 | 6/2005 | Ortiz et al. |
| 2005/0143818 A1 | 6/2005 | Yuan et al. |
| 2005/0143827 A1 | 6/2005 | Globerman et al. |
| 2005/0149022 A1 | 7/2005 | Shaolian et al. |
| 2005/0149030 A1 | 7/2005 | Serhan et al. |
| 2005/0149191 A1 | 7/2005 | Cragg et al. |
| 2005/0149192 A1 | 7/2005 | Zucherman et al. |
| 2005/0149193 A1 | 7/2005 | Zucherman et al. |
| 2005/0149194 A1 | 7/2005 | Ahlgren |
| 2005/0149197 A1 | 7/2005 | Cauthen |
| 2005/0154391 A1 | 7/2005 | Doherty et al. |
| 2005/0154396 A1 | 7/2005 | Foley et al. |
| 2005/0154463 A1 | 7/2005 | Trieu |
| 2005/0154467 A1 | 7/2005 | Peterman et al. |
| 2005/0159813 A1 | 7/2005 | Molz, IV |
| 2005/0159819 A1 | 7/2005 | McCormack et al. |
| 2005/0165398 A1 | 7/2005 | Reiley |
| 2005/0165406 A1 | 7/2005 | Assell et al. |
| 2005/0165483 A1 | 7/2005 | Ray et al. |
| 2005/0165485 A1 | 7/2005 | Trieu |
| 2005/0171539 A1 | 8/2005 | Braun et al. |
| 2005/0171552 A1 | 8/2005 | Johnson et al. |
| 2005/0171608 A1 | 8/2005 | Peterman et al. |
| 2005/0171610 A1 | 8/2005 | Humphreys et al. |
| 2005/0177235 A1 | 8/2005 | Baynham et al. |
| 2005/0177236 A1 | 8/2005 | Mathieu et al. |
| 2005/0177240 A1 | 8/2005 | Blain |
| 2005/0177245 A1 | 8/2005 | Leatherbury et al. |
| 2005/0182412 A1 | 8/2005 | Johnson et al. |
| 2005/0182413 A1 | 8/2005 | Johnson et al. |
| 2005/0182414 A1 | 8/2005 | Manzi et al. |
| 2005/0182416 A1 | 8/2005 | Lim et al. |
| 2005/0182418 A1 | 8/2005 | Boyd et al. |
| 2005/0187556 A1 | 8/2005 | Stack et al. |
| 2005/0187558 A1 | 8/2005 | Johnson et al. |
| 2005/0187559 A1 | 8/2005 | Raymond et al. |
| 2005/0187564 A1 | 8/2005 | Jayaraman |
| 2005/0197702 A1 | 9/2005 | Coppes et al. |
| 2005/0197707 A1 | 9/2005 | Trieu et al. |
| 2005/0203512 A1 | 9/2005 | Hawkins et al. |
| 2005/0209696 A1 | 9/2005 | Lin et al. |
| 2005/0216018 A1 | 9/2005 | Sennett |
| 2005/0216026 A1 | 9/2005 | Culbert |
| 2005/0216087 A1 | 9/2005 | Zucherman et al. |
| 2005/0222681 A1 | 10/2005 | Richley et al. |
| 2005/0222684 A1 | 10/2005 | Ferree |
| 2005/0228383 A1 | 10/2005 | Zucherman et al. |
| 2005/0228391 A1 | 10/2005 | Levy et al. |
| 2005/0228397 A1 | 10/2005 | Malandain et al. |
| 2005/0234425 A1 | 10/2005 | Miller et al. |
| 2005/0234451 A1 | 10/2005 | Markworth |
| 2005/0234452 A1 | 10/2005 | Malandain |
| 2005/0234456 A1 | 10/2005 | Malandain |
| 2005/0240182 A1 | 10/2005 | Zucherman et al. |
| 2005/0240189 A1 | 10/2005 | Rousseau et al. |
| 2005/0240193 A1 | 10/2005 | Layne et al. |
| 2005/0240269 A1 | 10/2005 | Lambrecht et al. |
| 2005/0251142 A1 | 11/2005 | Hoffmann et al. |
| 2005/0251149 A1 | 11/2005 | Wenz |
| 2005/0251260 A1 | 11/2005 | Gerber et al. |
| 2005/0256525 A1 | 11/2005 | Culbert et al. |
| 2005/0256576 A1 | 11/2005 | Moskowitz et al. |
| 2005/0261682 A1 | 11/2005 | Ferree |
| 2005/0261684 A1 | 11/2005 | Shaolian et al. |
| 2005/0261695 A1 | 11/2005 | Cragg et al. |
| 2005/0261768 A1 | 11/2005 | Trieu |
| 2005/0261769 A1 | 11/2005 | Moskowitz et al. |
| 2005/0261781 A1 | 11/2005 | Sennett et al. |
| 2005/0267471 A1 | 12/2005 | Biedermann et al. |
| 2005/0273166 A1 | 12/2005 | Sweeney |
| 2005/0273173 A1 | 12/2005 | Gordon et al. |
| 2005/0277938 A1 | 12/2005 | Parsons |
| 2005/0278023 A1 | 12/2005 | Zwirkoski |
| 2005/0278026 A1 | 12/2005 | Gordon et al. |
| 2005/0278027 A1 | 12/2005 | Hyde, Jr. |
| 2005/0278029 A1 | 12/2005 | Trieu |
| 2005/0278036 A1 | 12/2005 | Leonard et al. |
| 2005/0283238 A1 | 12/2005 | Reiley |
| 2005/0283244 A1 | 12/2005 | Gordon et al. |
| 2005/0287071 A1 | 12/2005 | Wenz |
| 2006/0004326 A1 | 1/2006 | Collins et al. |
| 2006/0004456 A1 | 1/2006 | McKay |
| 2006/0004457 A1 | 1/2006 | Collins et al. |
| 2006/0004458 A1 | 1/2006 | Collins et al. |
| 2006/0009778 A1 | 1/2006 | Collins et al. |
| 2006/0009779 A1 | 1/2006 | Collins et al. |
| 2006/0009851 A1 | 1/2006 | Collins et al. |
| 2006/0015105 A1 | 1/2006 | Warren et al. |
| 2006/0015119 A1 | 1/2006 | Plassky et al. |
| 2006/0020284 A1 | 1/2006 | Foley et al. |
| 2006/0020872 A1 | 1/2006 | Richardson et al. |
| 2006/0022180 A1 | 2/2006 | Selness |
| 2006/0025860 A1 | 2/2006 | Li |
| 2006/0030850 A1 | 2/2006 | Keegan et al. |
| 2006/0030851 A1 | 2/2006 | Bray et al. |
| 2006/0030872 A1 | 2/2006 | Culbert et al. |
| 2006/0030933 A1 | 2/2006 | Delegge et al. |
| 2006/0030943 A1 | 2/2006 | Peterman |
| 2006/0036241 A1 | 2/2006 | Siegal |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036261 A1 | 2/2006 | McDonnell |
| 2006/0036273 A1 | 2/2006 | Siegal |
| 2006/0036323 A1 | 2/2006 | Carl et al. |
| 2006/0036324 A1 | 2/2006 | Sachs et al. |
| 2006/0041258 A1 | 2/2006 | Galea |

(56) References Cited

U.S. PATENT DOCUMENTS

| | | |
|---|---|---|
| 2006/0041314 A1 | 2/2006 | Millard |
| 2006/0045904 A1 | 3/2006 | Aronson |
| 2006/0052788 A1 | 3/2006 | Thelen et al. |
| 2006/0058790 A1 | 3/2006 | Carl et al. |
| 2006/0058801 A1 | 3/2006 | Schlienger et al. |
| 2006/0058807 A1 | 3/2006 | Landry et al. |
| 2006/0058876 A1 | 3/2006 | McKinley |
| 2006/0058880 A1 | 3/2006 | Wysocki et al. |
| 2006/0064171 A1 | 3/2006 | Trieu |
| 2006/0064172 A1 | 3/2006 | Trieu |
| 2006/0069439 A1 | 3/2006 | Zucherman et al. |
| 2006/0069440 A1 | 3/2006 | Zucherman et al. |
| 2006/0079908 A1 | 4/2006 | Lieberman |
| 2006/0079961 A1 | 4/2006 | Michelson |
| 2006/0084867 A1 | 4/2006 | Tremblay et al. |
| 2006/0084977 A1 | 4/2006 | Lieberman |
| 2006/0084988 A1 | 4/2006 | Kim |
| 2006/0085002 A1 | 4/2006 | Trieu et al. |
| 2006/0085009 A1 | 4/2006 | Truckai et al. |
| 2006/0085010 A1 | 4/2006 | Lieberman |
| 2006/0085071 A1 | 4/2006 | Lechmann et al. |
| 2006/0089642 A1 | 4/2006 | Diaz et al. |
| 2006/0089646 A1 | 4/2006 | Bonutti |
| 2006/0089654 A1 | 4/2006 | Lins et al. |
| 2006/0089715 A1 | 4/2006 | Truckai et al. |
| 2006/0089718 A1 | 4/2006 | Zucherman et al. |
| 2006/0089719 A1 | 4/2006 | Trieu |
| 2006/0095045 A1 | 5/2006 | Trieu |
| 2006/0095046 A1 | 5/2006 | Trieu et al. |
| 2006/0095134 A1 | 5/2006 | Trieu et al. |
| 2006/0095138 A1 | 5/2006 | Truckai et al. |
| 2006/0100706 A1 | 5/2006 | Shadduck et al. |
| 2006/0100707 A1 | 5/2006 | Stinson et al. |
| 2006/0106381 A1 | 5/2006 | Ferree et al. |
| 2006/0106397 A1 | 5/2006 | Lins |
| 2006/0106459 A1 | 5/2006 | Truckai et al. |
| 2006/0111785 A1 | 5/2006 | O'Neil |
| 2006/0116768 A1 | 6/2006 | Krueger et al. |
| 2006/0119629 A1 | 6/2006 | An et al. |
| 2006/0122609 A1 | 6/2006 | Mirkovic et al. |
| 2006/0122610 A1 | 6/2006 | Culbert et al. |
| 2006/0122701 A1 | 6/2006 | Kiester |
| 2006/0122703 A1 | 6/2006 | Aebi et al. |
| 2006/0122704 A1 | 6/2006 | Vresilovic et al. |
| 2006/0129244 A1 | 6/2006 | Ensign |
| 2006/0129424 A1 | 6/2006 | Chan |
| 2006/0136062 A1 | 6/2006 | Dinello et al. |
| 2006/0136064 A1 | 6/2006 | Sherman |
| 2006/0142759 A1 | 6/2006 | Arnin et al. |
| 2006/0142765 A9 | 6/2006 | Dixon et al. |
| 2006/0142776 A1 | 6/2006 | Iwanari |
| 2006/0142858 A1 | 6/2006 | Colleran et al. |
| 2006/0142863 A1 | 6/2006 | Fraser et al. |
| 2006/0142864 A1 | 6/2006 | Cauthen |
| 2006/0149136 A1 | 7/2006 | Seto et al. |
| 2006/0149237 A1 | 7/2006 | Markworth et al. |
| 2006/0149252 A1 | 7/2006 | Markworth et al. |
| 2006/0149379 A1 | 7/2006 | Kuslich et al. |
| 2006/0149380 A1 | 7/2006 | Lotz et al. |
| 2006/0152863 A1 | 7/2006 | Freitag et al. |
| 2006/0155379 A1 | 7/2006 | Heneveld et al. |
| 2006/0161162 A1 | 7/2006 | Lambrecht et al. |
| 2006/0161166 A1 | 7/2006 | Johnson et al. |
| 2006/0167553 A1 | 7/2006 | Cauthen et al. |
| 2006/0173545 A1 | 8/2006 | Cauthen et al. |
| 2006/0178743 A1 | 8/2006 | Carter |
| 2006/0178745 A1 | 8/2006 | Bartish et al. |
| 2006/0178746 A1 | 8/2006 | Bartish et al. |
| 2006/0184192 A1 | 8/2006 | Markworth et al. |
| 2006/0184247 A1 | 8/2006 | Edidin et al. |
| 2006/0184248 A1 | 8/2006 | Edidin et al. |
| 2006/0189999 A1 | 8/2006 | Zwirkoski |
| 2006/0190083 A1 | 8/2006 | Arnin et al. |
| 2006/0190085 A1 | 8/2006 | Cauthen |
| 2006/0195102 A1 | 8/2006 | Malandain |
| 2006/0195103 A1 | 8/2006 | Padget et al. |
| 2006/0195191 A1 | 8/2006 | Sweeney et al. |
| 2006/0200139 A1 | 9/2006 | Michelson |
| 2006/0200164 A1 | 9/2006 | Michelson |
| 2006/0200239 A1 | 9/2006 | Rothman et al. |
| 2006/0200240 A1 | 9/2006 | Rothman et al. |
| 2006/0200241 A1 | 9/2006 | Rothman et al. |
| 2006/0200242 A1 | 9/2006 | Rothman et al. |
| 2006/0200243 A1 | 9/2006 | Rothman et al. |
| 2006/0206116 A1 | 9/2006 | Yeung |
| 2006/0206207 A1 | 9/2006 | Dryer et al. |
| 2006/0211952 A1 | 9/2006 | Kennedy, II |
| 2006/0215343 A1 | 9/2006 | Camagna et al. |
| 2006/0217711 A1 | 9/2006 | Stevens et al. |
| 2006/0229609 A1 | 10/2006 | Wang |
| 2006/0229629 A1 | 10/2006 | Manzi et al. |
| 2006/0229724 A1 | 10/2006 | Lechmann et al. |
| 2006/0229725 A1 | 10/2006 | Lechmann et al. |
| 2006/0229729 A1 | 10/2006 | Gordon et al. |
| 2006/0235403 A1 | 10/2006 | Blain |
| 2006/0235409 A1 | 10/2006 | Blain |
| 2006/0235411 A1 | 10/2006 | Blain et al. |
| 2006/0235412 A1 | 10/2006 | Blain |
| 2006/0235423 A1 | 10/2006 | Cantu |
| 2006/0235518 A1 | 10/2006 | Blain |
| 2006/0235521 A1 | 10/2006 | Zucherman et al. |
| 2006/0235531 A1 | 10/2006 | Buettner-Janz |
| 2006/0235535 A1 | 10/2006 | Ferree et al. |
| 2006/0241597 A1 | 10/2006 | Mitchell et al. |
| 2006/0241663 A1 | 10/2006 | Rice et al. |
| 2006/0241761 A1 | 10/2006 | Gately |
| 2006/0241770 A1 | 10/2006 | Rhoda et al. |
| 2006/0247634 A1 | 11/2006 | Warner et al. |
| 2006/0247650 A1 | 11/2006 | Yerby et al. |
| 2006/0247770 A1 | 11/2006 | Peterman |
| 2006/0247771 A1 | 11/2006 | Peterman et al. |
| 2006/0247781 A1 | 11/2006 | Francis |
| 2006/0253201 A1 | 11/2006 | McLuen |
| 2006/0259147 A1 | 11/2006 | Krishna et al. |
| 2006/0264896 A1 | 11/2006 | Palmer |
| 2006/0264939 A1 | 11/2006 | Zucherman et al. |
| 2006/0264945 A1 | 11/2006 | Edidin et al. |
| 2006/0265067 A1 | 11/2006 | Zucherman et al. |
| 2006/0265068 A1 | 11/2006 | Schwab |
| 2006/0265075 A1 | 11/2006 | Baumgartner et al. |
| 2006/0265077 A1 | 11/2006 | Zwirkoski |
| 2006/0271049 A1 | 11/2006 | Zucherman et al. |
| 2006/0271061 A1 | 11/2006 | Beyar et al. |
| 2006/0276897 A1 | 12/2006 | Winslow et al. |
| 2006/0276899 A1 | 12/2006 | Zipnick et al. |
| 2006/0276901 A1 | 12/2006 | Zipnick et al. |
| 2006/0276902 A1 | 12/2006 | Zipnick et al. |
| 2006/0282167 A1 | 12/2006 | Lambrecht et al. |
| 2006/0287726 A1 | 12/2006 | Segal et al. |
| 2006/0287727 A1 | 12/2006 | Segal et al. |
| 2006/0293662 A1 | 12/2006 | Boyer et al. |
| 2006/0293663 A1 | 12/2006 | Walkenhorst et al. |
| 2006/0293753 A1 | 12/2006 | Thramann |
| 2007/0006692 A1 | 1/2007 | Phan |
| 2007/0010716 A1 | 1/2007 | Malandain et al. |
| 2007/0010717 A1 | 1/2007 | Cragg |
| 2007/0010824 A1 | 1/2007 | Malandain et al. |
| 2007/0010826 A1 | 1/2007 | Rhoda et al. |
| 2007/0010844 A1 | 1/2007 | Gong et al. |
| 2007/0010845 A1 | 1/2007 | Gong et al. |
| 2007/0010846 A1 | 1/2007 | Leung et al. |
| 2007/0010848 A1 | 1/2007 | Leung et al. |
| 2007/0010886 A1 | 1/2007 | Banick et al. |
| 2007/0010889 A1 | 1/2007 | Francis |
| 2007/0016191 A1 | 1/2007 | Culbert et al. |
| 2007/0032703 A1 | 2/2007 | Sankaran et al. |
| 2007/0032790 A1 | 2/2007 | Aschmann et al. |
| 2007/0032791 A1 | 2/2007 | Greenhalgh |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2007/0043440 A1 | 2/2007 | William et al. |
| 2007/0048382 A1 | 3/2007 | Meyer et al. |
| 2007/0049849 A1 | 3/2007 | Schwardt et al. |

(56) References Cited

U.S. PATENT DOCUMENTS

| | | |
|---|---|---|
| 2007/0049934 A1 | 3/2007 | Edidin et al. |
| 2007/0049935 A1 | 3/2007 | Edidin et al. |
| 2007/0049941 A1 | 3/2007 | Thramann |
| 2007/0050034 A1 | 3/2007 | Schwardt et al. |
| 2007/0050035 A1 | 3/2007 | Schwardt et al. |
| 2007/0055201 A1 | 3/2007 | Seto et al. |
| 2007/0055236 A1 | 3/2007 | Hudgins et al. |
| 2007/0055237 A1 | 3/2007 | Edidin et al. |
| 2007/0055246 A1 | 3/2007 | Zucherman et al. |
| 2007/0055252 A1 | 3/2007 | Blain et al. |
| 2007/0055265 A1 | 3/2007 | Schaller |
| 2007/0055266 A1 | 3/2007 | Osorio et al. |
| 2007/0055267 A1 | 3/2007 | Osorio et al. |
| 2007/0055271 A1 | 3/2007 | Schaller |
| 2007/0055272 A1 | 3/2007 | Schaller |
| 2007/0055273 A1 | 3/2007 | Schaller |
| 2007/0055274 A1 | 3/2007 | Appenzeller et al. |
| 2007/0055275 A1 | 3/2007 | Schaller |
| 2007/0055276 A1 | 3/2007 | Edidin |
| 2007/0055277 A1 | 3/2007 | Osorio et al. |
| 2007/0055278 A1 | 3/2007 | Osorio et al. |
| 2007/0055281 A1 | 3/2007 | Osorio et al. |
| 2007/0055284 A1 | 3/2007 | Osorio et al. |
| 2007/0055300 A1 | 3/2007 | Osorio et al. |
| 2007/0055377 A1 | 3/2007 | Hanson et al. |
| 2007/0060933 A1 | 3/2007 | Sankaran et al. |
| 2007/0060935 A1 | 3/2007 | Schwardt et al. |
| 2007/0067034 A1 | 3/2007 | Chirico et al. |
| 2007/0067035 A1 | 3/2007 | Falahee |
| 2007/0068329 A1 | 3/2007 | Phan et al. |
| 2007/0073292 A1 | 3/2007 | Kohm et al. |
| 2007/0073398 A1 | 3/2007 | Fabian et al. |
| 2007/0073399 A1 | 3/2007 | Zipnick et al. |
| 2007/0078436 A1 | 4/2007 | Leung et al. |
| 2007/0078463 A1 | 4/2007 | Malandain |
| 2007/0093689 A1 | 4/2007 | Steinberg |
| 2007/0093899 A1 | 4/2007 | Dutoit et al. |
| 2007/0093906 A1 | 4/2007 | Hudgins et al. |
| 2007/0106384 A1 | 5/2007 | Bray et al. |
| 2007/0106388 A1 | 5/2007 | Michelson |
| 2007/0118132 A1 | 5/2007 | Culbert et al. |
| 2007/0118222 A1 | 5/2007 | Lang |
| 2007/0118223 A1 | 5/2007 | Allard et al. |
| 2007/0123868 A1 | 5/2007 | Culbert et al. |
| 2007/0123891 A1 | 5/2007 | Ries et al. |
| 2007/0123892 A1 | 5/2007 | Ries et al. |
| 2007/0123986 A1 | 5/2007 | Schaller |
| 2007/0129730 A1 | 6/2007 | Woods et al. |
| 2007/0129804 A1 | 6/2007 | Bentley et al. |
| 2007/0135922 A1 | 6/2007 | Trieu |
| 2007/0149978 A1 | 6/2007 | Shezifi et al. |
| 2007/0150059 A1 | 6/2007 | Ruberte et al. |
| 2007/0150060 A1 | 6/2007 | Trieu |
| 2007/0150061 A1 | 6/2007 | Trieu |
| 2007/0150063 A1 | 6/2007 | Ruberte et al. |
| 2007/0150064 A1 | 6/2007 | Ruberte et al. |
| 2007/0162005 A1 | 7/2007 | Peterson et al. |
| 2007/0162127 A1 | 7/2007 | Peterman et al. |
| 2007/0162138 A1 | 7/2007 | Heinz |
| 2007/0167945 A1 | 7/2007 | Lange et al. |
| 2007/0168036 A1 | 7/2007 | Ainsworth et al. |
| 2007/0168038 A1 | 7/2007 | Trieu |
| 2007/0173939 A1 | 7/2007 | Kim et al. |
| 2007/0173940 A1 | 7/2007 | Hestad et al. |
| 2007/0178222 A1 | 8/2007 | Storey et al. |
| 2007/0179612 A1 | 8/2007 | Johnson et al. |
| 2007/0179615 A1 | 8/2007 | Heinz et al. |
| 2007/0179616 A1 | 8/2007 | Braddock et al. |
| 2007/0179618 A1 | 8/2007 | Trieu et al. |
| 2007/0185578 A1 | 8/2007 | O'Neil et al. |
| 2007/0191953 A1 | 8/2007 | Trieu |
| 2007/0191954 A1 | 8/2007 | Hansell et al. |
| 2007/0191959 A1 | 8/2007 | Hartmann et al. |
| 2007/0197935 A1 | 8/2007 | Reiley et al. |
| 2007/0198016 A1 | 8/2007 | Zang et al. |
| 2007/0198023 A1 | 8/2007 | Sand et al. |
| 2007/0198025 A1 | 8/2007 | Trieu et al. |
| 2007/0198089 A1 | 8/2007 | Moskowitz et al. |
| 2007/0203491 A1 | 8/2007 | Pasquet et al. |
| 2007/0208423 A1 | 9/2007 | Messerli et al. |
| 2007/0208426 A1 | 9/2007 | Trieu |
| 2007/0213717 A1 | 9/2007 | Trieu et al. |
| 2007/0213737 A1 | 9/2007 | Schermerhorn et al. |
| 2007/0213820 A1 | 9/2007 | Magerl et al. |
| 2007/0219634 A1 | 9/2007 | Greenhalgh et al. |
| 2007/0219635 A1 | 9/2007 | Mathieu et al. |
| 2007/0233074 A1 | 10/2007 | Anderson et al. |
| 2007/0233083 A1 | 10/2007 | Abdou |
| 2007/0233089 A1 | 10/2007 | Dipoto et al. |
| 2007/0233118 A1 | 10/2007 | McLain |
| 2007/0233244 A1 | 10/2007 | Lopez et al. |
| 2007/0233253 A1 | 10/2007 | Bray et al. |
| 2007/0233254 A1 | 10/2007 | Grotz et al. |
| 2007/0233261 A1 | 10/2007 | Lopez et al. |
| 2007/0233263 A1 | 10/2007 | Melkent et al. |
| 2007/0250167 A1 | 10/2007 | Bray et al. |
| 2007/0255146 A1 | 11/2007 | Andrews et al. |
| 2007/0255416 A1 | 11/2007 | Melkent et al. |
| 2007/0260255 A1 | 11/2007 | Haddock et al. |
| 2007/0265631 A1 | 11/2007 | Fox |
| 2007/0270954 A1 | 11/2007 | Wu |
| 2007/0270957 A1 | 11/2007 | Heinz |
| 2007/0270965 A1 | 11/2007 | Ferguson |
| 2007/0270968 A1 | 11/2007 | Baynham et al. |
| 2007/0276375 A1 | 11/2007 | Rapp |
| 2007/0276490 A1 | 11/2007 | Mateyka |
| 2007/0282443 A1 | 12/2007 | Globerman et al. |
| 2007/0282449 A1 | 12/2007 | De et al. |
| 2007/0293948 A1 | 12/2007 | Bagga et al. |
| 2007/0299521 A1 | 12/2007 | Glenn et al. |
| 2008/0009877 A1 | 1/2008 | Sankaran et al. |
| 2008/0015694 A1 | 1/2008 | Tribus |
| 2008/0015701 A1 | 1/2008 | Garcia et al. |
| 2008/0021556 A1 | 1/2008 | Edie |
| 2008/0021557 A1 | 1/2008 | Trieu |
| 2008/0021558 A1 | 1/2008 | Thramann |
| 2008/0027437 A1 | 1/2008 | Johnson et al. |
| 2008/0027453 A1 | 1/2008 | Johnson et al. |
| 2008/0027454 A1 | 1/2008 | Johnson et al. |
| 2008/0027550 A1 | 1/2008 | Link et al. |
| 2008/0033440 A1 | 2/2008 | Moskowitz et al. |
| 2008/0039846 A1 | 2/2008 | Lee et al. |
| 2008/0051890 A1 | 2/2008 | Waugh et al. |
| 2008/0051897 A1 | 2/2008 | Lopez et al. |
| 2008/0051902 A1 | 2/2008 | Dwyer |
| 2008/0058598 A1 | 3/2008 | Ries et al. |
| 2008/0058944 A1 | 3/2008 | Duplessis et al. |
| 2008/0065219 A1 | 3/2008 | Dye |
| 2008/0071356 A1 | 3/2008 | Greenhalgh et al. |
| 2008/0077148 A1 | 3/2008 | Ries et al. |
| 2008/0077247 A1 | 3/2008 | Murillo et al. |
| 2008/0082172 A1 | 4/2008 | Jackson |
| 2008/0082173 A1 | 4/2008 | Delurio et al. |
| 2008/0097436 A1 | 4/2008 | Culbert et al. |
| 2008/0097611 A1 | 4/2008 | Mastrorio et al. |
| 2008/0103597 A1 | 5/2008 | Lechmann et al. |
| 2008/0103598 A1 | 5/2008 | Trudeau et al. |
| 2008/0103601 A1 | 5/2008 | Biro et al. |
| 2008/0108996 A1 | 5/2008 | Padget et al. |
| 2008/0109005 A1 | 5/2008 | Trudeau et al. |
| 2008/0119933 A1 | 5/2008 | Aebi et al. |
| 2008/0125865 A1 | 5/2008 | Abdelgany |
| 2008/0132934 A1 | 6/2008 | Reiley et al. |
| 2008/0132949 A1 | 6/2008 | Aferzon et al. |
| 2008/0132958 A1 | 6/2008 | Pech et al. |
| 2008/0133012 A1 | 6/2008 | McGuckin |
| 2008/0133014 A1 | 6/2008 | Gately et al. |
| 2008/0133017 A1 | 6/2008 | Beyar et al. |
| 2008/0140085 A1 | 6/2008 | Gately et al. |
| 2008/0140207 A1 | 6/2008 | Olmos et al. |
| 2008/0147193 A1 | 6/2008 | Matthis et al. |
| 2008/0154377 A1 | 6/2008 | Voellmicke |
| 2008/0161922 A1 | 7/2008 | Rhoda |
| 2008/0161925 A1 | 7/2008 | Brittan et al. |

(56) References Cited

U.S. PATENT DOCUMENTS

| | | |
|---|---|---|
| 2008/0161927 A1 | 7/2008 | Savage et al. |
| 2008/0167657 A1 | 7/2008 | Greenhalgh |
| 2008/0167666 A1 | 7/2008 | Fiere et al. |
| 2008/0172128 A1 | 7/2008 | Perez-Cruet et al. |
| 2008/0177306 A1 | 7/2008 | Lamborne et al. |
| 2008/0177307 A1 | 7/2008 | Moskowitz et al. |
| 2008/0177388 A1 | 7/2008 | Patterson et al. |
| 2008/0183204 A1 | 7/2008 | Greenhalgh et al. |
| 2008/0183293 A1 | 7/2008 | Parry et al. |
| 2008/0183294 A1 | 7/2008 | Adl |
| 2008/0188945 A1 | 8/2008 | Boyce et al. |
| 2008/0195096 A1 | 8/2008 | Frei |
| 2008/0195209 A1 | 8/2008 | Garcia et al. |
| 2008/0195210 A1 | 8/2008 | Milijasevic et al. |
| 2008/0208255 A1 | 8/2008 | Siegal |
| 2008/0221687 A1 | 9/2008 | Viker |
| 2008/0221690 A1 | 9/2008 | Chaput et al. |
| 2008/0221694 A1 | 9/2008 | Warnick et al. |
| 2008/0228225 A1 | 9/2008 | Trautwein et al. |
| 2008/0229597 A1 | 9/2008 | Malandain |
| 2008/0234682 A1 | 9/2008 | Park |
| 2008/0234822 A1 | 9/2008 | Govil et al. |
| 2008/0243136 A1 | 10/2008 | Prager et al. |
| 2008/0243251 A1 | 10/2008 | Stad et al. |
| 2008/0243254 A1 | 10/2008 | Butler |
| 2008/0249569 A1 | 10/2008 | Waugh et al. |
| 2008/0249575 A1 | 10/2008 | Waugh et al. |
| 2008/0249622 A1 | 10/2008 | Gray |
| 2008/0249625 A1 | 10/2008 | Waugh et al. |
| 2008/0255618 A1 | 10/2008 | Fisher et al. |
| 2008/0255620 A1 | 10/2008 | Strauss et al. |
| 2008/0262619 A1 | 10/2008 | Ray |
| 2008/0269806 A1 | 10/2008 | Zhang et al. |
| 2008/0269904 A1 | 10/2008 | Voorhies |
| 2008/0281346 A1 | 11/2008 | Greenhalgh et al. |
| 2008/0281364 A1 | 11/2008 | Chirico et al. |
| 2008/0281425 A1 | 11/2008 | Thalgott et al. |
| 2008/0287981 A1 | 11/2008 | Culbert et al. |
| 2008/0287997 A1 | 11/2008 | Altarac et al. |
| 2008/0294262 A1 | 11/2008 | Levieux |
| 2008/0300601 A1 | 12/2008 | Fabian et al. |
| 2008/0300634 A1 | 12/2008 | Gray |
| 2008/0300685 A1 | 12/2008 | Carls et al. |
| 2008/0306537 A1 | 12/2008 | Culbert |
| 2008/0306596 A1 | 12/2008 | Jones et al. |
| 2008/0306598 A1 | 12/2008 | Hansen et al. |
| 2008/0312698 A1 | 12/2008 | Bergeron et al. |
| 2008/0312742 A1 | 12/2008 | Abernathie |
| 2008/0312743 A1 | 12/2008 | Vila et al. |
| 2008/0319477 A1 | 12/2008 | Justis et al. |
| 2009/0005870 A1 | 1/2009 | Hawkins et al. |
| 2009/0005873 A1 | 1/2009 | Slivka et al. |
| 2009/0012529 A1 | 1/2009 | Blain et al. |
| 2009/0018524 A1 | 1/2009 | Greenhalgh et al. |
| 2009/0030421 A1 | 1/2009 | Hawkins et al. |
| 2009/0030423 A1 | 1/2009 | Puno |
| 2009/0030519 A1 | 1/2009 | Falahee |
| 2009/0030520 A1 | 1/2009 | Biedermann et al. |
| 2009/0048631 A1 | 2/2009 | Bhatnagar et al. |
| 2009/0048678 A1 | 2/2009 | Saal et al. |
| 2009/0054991 A1 | 2/2009 | Biyani et al. |
| 2009/0062921 A1 | 3/2009 | Michelson |
| 2009/0069813 A1 | 3/2009 | Von et al. |
| 2009/0069895 A1 | 3/2009 | Gittings et al. |
| 2009/0074538 A1 | 3/2009 | Richie |
| 2009/0076610 A1 | 3/2009 | Afzal |
| 2009/0088849 A1 | 4/2009 | Armstrong et al. |
| 2009/0099554 A1 | 4/2009 | Forster et al. |
| 2009/0099568 A1 | 4/2009 | Lowry et al. |
| 2009/0099610 A1 | 4/2009 | Johnson et al. |
| 2009/0099661 A1 | 4/2009 | Bhattacharya et al. |
| 2009/0105712 A1 | 4/2009 | Dauster et al. |
| 2009/0105745 A1 | 4/2009 | Culbert |
| 2009/0105771 A1 | 4/2009 | Lei et al. |
| 2009/0105774 A1 | 4/2009 | Jones et al. |
| 2009/0105830 A1 | 4/2009 | Jones et al. |
| 2009/0105831 A1 | 4/2009 | Jones et al. |
| 2009/0105832 A1 | 4/2009 | Allain et al. |
| 2009/0112320 A1 | 4/2009 | Kraus |
| 2009/0112324 A1 | 4/2009 | Refai et al. |
| 2009/0125028 A1 | 5/2009 | Teisen et al. |
| 2009/0131986 A1 | 5/2009 | Lee et al. |
| 2009/0131988 A1 | 5/2009 | Bush et al. |
| 2009/0132054 A1 | 5/2009 | Zeegers |
| 2009/0143859 A1 | 6/2009 | McClellan et al. |
| 2009/0149857 A1 | 6/2009 | Culbert et al. |
| 2009/0164020 A1 | 6/2009 | Janowski et al. |
| 2009/0177281 A1 | 7/2009 | Swanson et al. |
| 2009/0177284 A1 | 7/2009 | Rogers et al. |
| 2009/0182428 A1 | 7/2009 | McClellan et al. |
| 2009/0182429 A1 | 7/2009 | Humphreys et al. |
| 2009/0182430 A1 | 7/2009 | Tyber et al. |
| 2009/0192549 A1 | 7/2009 | Sanders et al. |
| 2009/0192613 A1 | 7/2009 | Wing et al. |
| 2009/0192614 A1 | 7/2009 | Beger et al. |
| 2009/0192615 A1 | 7/2009 | Tyber et al. |
| 2009/0192616 A1 | 7/2009 | Zielinski |
| 2009/0198245 A1 | 8/2009 | Phan |
| 2009/0198287 A1 | 8/2009 | Chiu |
| 2009/0198339 A1 | 8/2009 | Kleiner et al. |
| 2009/0210062 A1 | 8/2009 | Thalgott et al. |
| 2009/0210064 A1 | 8/2009 | Lechmann et al. |
| 2009/0222096 A1 | 9/2009 | Trieu |
| 2009/0222099 A1 | 9/2009 | Liu et al. |
| 2009/0222100 A1 | 9/2009 | Cipoletti et al. |
| 2009/0224023 A1 | 9/2009 | Moskowitz et al. |
| 2009/0234364 A1 | 9/2009 | Crook |
| 2009/0234398 A1 | 9/2009 | Chirico et al. |
| 2009/0240333 A1 | 9/2009 | Trudeau et al. |
| 2009/0240334 A1 | 9/2009 | Richelsoph |
| 2009/0240335 A1 | 9/2009 | Arcenio et al. |
| 2009/0248092 A1 | 10/2009 | Bellas et al. |
| 2009/0248159 A1 | 10/2009 | Aflatoon |
| 2009/0248163 A1 | 10/2009 | King et al. |
| 2009/0259316 A1 | 10/2009 | Ginn et al. |
| 2009/0265007 A1 | 10/2009 | Colleran |
| 2009/0270873 A1 | 10/2009 | Fabian |
| 2009/0275890 A1 | 11/2009 | Leibowitz et al. |
| 2009/0276051 A1 | 11/2009 | Arramon et al. |
| 2009/0281580 A1 | 11/2009 | Emannuel |
| 2009/0287251 A1 | 11/2009 | Bae et al. |
| 2009/0292361 A1 | 11/2009 | Lopez |
| 2009/0306779 A1 | 12/2009 | Ahn |
| 2009/0326543 A1 | 12/2009 | Fabian, Jr. |
| 2009/0326580 A1 | 12/2009 | Anderson et al. |
| 2009/0326589 A1 | 12/2009 | Lemoine et al. |
| 2010/0004747 A1 | 1/2010 | Lin |
| 2010/0016901 A1 | 1/2010 | Robinson |
| 2010/0016905 A1 | 1/2010 | Greenhalgh et al. |
| 2010/0016973 A1 | 1/2010 | De et al. |
| 2010/0023128 A1 | 1/2010 | Malberg |
| 2010/0030334 A1 | 2/2010 | Molz, IV |
| 2010/0036496 A1 | 2/2010 | Yu et al. |
| 2010/0040332 A1 | 2/2010 | Van et al. |
| 2010/0042159 A1 | 2/2010 | Butler |
| 2010/0042218 A1 | 2/2010 | Nebosky et al. |
| 2010/0057206 A1 | 3/2010 | Duffield et al. |
| 2010/0069969 A1 | 3/2010 | Ampuero et al. |
| 2010/0070037 A1 | 3/2010 | Parry et al. |
| 2010/0076492 A1 | 3/2010 | Warner et al. |
| 2010/0076559 A1 | 3/2010 | Bagga et al. |
| 2010/0078372 A1 | 4/2010 | Kerfoot |
| 2010/0082109 A1 | 4/2010 | Greenhalgh et al. |
| 2010/0087925 A1 | 4/2010 | Kostuik et al. |
| 2010/0094424 A1 | 4/2010 | Woodburn et al. |
| 2010/0094426 A1 | 4/2010 | Grohowski et al. |
| 2010/0106249 A1 | 4/2010 | Tyber et al. |
| 2010/0114105 A1 | 5/2010 | Butters et al. |
| 2010/0114147 A1 | 5/2010 | Biyani |
| 2010/0137987 A1 | 6/2010 | Diao et al. |
| 2010/0145457 A1 | 6/2010 | Felt et al. |
| 2010/0145459 A1 | 6/2010 | McDonough et al. |
| 2010/0145460 A1 | 6/2010 | McDonough et al. |
| 2010/0150301 A1 | 6/2010 | Chan et al. |

(56) References Cited

U.S. PATENT DOCUMENTS

| | | |
|---|---|---|
| 2010/0174314 A1 | 7/2010 | Mirkovic et al. |
| 2010/0179594 A1 | 7/2010 | Theofilos et al. |
| 2010/0179656 A1 | 7/2010 | Theofilos |
| 2010/0185287 A1 | 7/2010 | Allard et al. |
| 2010/0185289 A1 | 7/2010 | Kirwan et al. |
| 2010/0185292 A1 | 7/2010 | Hochschuler et al. |
| 2010/0191336 A1 | 7/2010 | Greenhalgh |
| 2010/0204739 A1 | 8/2010 | Bae et al. |
| 2010/0204795 A1 | 8/2010 | Greenhalgh |
| 2010/0204796 A1 | 8/2010 | Bae et al. |
| 2010/0211176 A1 | 8/2010 | Greenhalgh |
| 2010/0211182 A1 | 8/2010 | Zimmermann |
| 2010/0217325 A1 | 8/2010 | Hochschuler et al. |
| 2010/0217393 A1 | 8/2010 | Theofilos |
| 2010/0234956 A1 | 9/2010 | Attia et al. |
| 2010/0241231 A1 | 9/2010 | Marino et al. |
| 2010/0249935 A1 | 9/2010 | Slivka et al. |
| 2010/0249937 A1 | 9/2010 | Blain et al. |
| 2010/0256759 A1 | 10/2010 | Hansell et al. |
| 2010/0256760 A1 | 10/2010 | Hansell |
| 2010/0262240 A1 | 10/2010 | Chavatte et al. |
| 2010/0268231 A1 | 10/2010 | Kuslich et al. |
| 2010/0268338 A1 | 10/2010 | Melkent et al. |
| 2010/0286777 A1 | 11/2010 | Errico et al. |
| 2010/0286781 A1 | 11/2010 | Bullard |
| 2010/0286783 A1 | 11/2010 | Lechmann et al. |
| 2010/0292696 A1 | 11/2010 | Chantelot et al. |
| 2010/0292700 A1 | 11/2010 | Ries |
| 2010/0292737 A1 | 11/2010 | Suh |
| 2010/0298938 A1 | 11/2010 | Humphreys et al. |
| 2010/0305704 A1 | 12/2010 | Messerli et al. |
| 2010/0312345 A1 | 12/2010 | Duffield et al. |
| 2010/0312346 A1 | 12/2010 | Kueenzi et al. |
| 2010/0324607 A1 | 12/2010 | Davis |
| 2010/0331891 A1 | 12/2010 | Culbert et al. |
| 2011/0004308 A1 | 1/2011 | Marino et al. |
| 2011/0004310 A1 | 1/2011 | Michelson |
| 2011/0009908 A1 | 1/2011 | Ferguson |
| 2011/0009966 A1 | 1/2011 | Michelson |
| 2011/0015675 A1 | 1/2011 | Howard et al. |
| 2011/0015745 A1 | 1/2011 | Bucci |
| 2011/0015747 A1 | 1/2011 | McManus et al. |
| 2011/0029082 A1 | 2/2011 | Hall |
| 2011/0029086 A1 | 2/2011 | Glazer et al. |
| 2011/0035011 A1 | 2/2011 | Cain |
| 2011/0054538 A1 | 3/2011 | Zehavi et al. |
| 2011/0071527 A1 | 3/2011 | Nelson et al. |
| 2011/0082550 A1 | 4/2011 | Yeh |
| 2011/0082552 A1 | 4/2011 | Wistrom et al. |
| 2011/0082555 A1 | 4/2011 | Martz et al. |
| 2011/0093074 A1 | 4/2011 | Glerum et al. |
| 2011/0093076 A1 | 4/2011 | Reo et al. |
| 2011/0098531 A1 | 4/2011 | To |
| 2011/0098628 A1 | 4/2011 | Yeung et al. |
| 2011/0098747 A1 | 4/2011 | Donner et al. |
| 2011/0098818 A1 | 4/2011 | Brodke et al. |
| 2011/0106159 A1 | 5/2011 | Nazeck |
| 2011/0118843 A1 | 5/2011 | Mathieu et al. |
| 2011/0130835 A1 | 6/2011 | Ashley et al. |
| 2011/0130838 A1 | 6/2011 | Morgenstern Lopez |
| 2011/0144692 A1 | 6/2011 | Saladin et al. |
| 2011/0144703 A1 | 6/2011 | Krause et al. |
| 2011/0144753 A1 | 6/2011 | Marchek et al. |
| 2011/0153020 A1 | 6/2011 | Abdelgany et al. |
| 2011/0159070 A1 | 6/2011 | Jin et al. |
| 2011/0160866 A1 | 6/2011 | Laurence et al. |
| 2011/0166656 A1 | 7/2011 | Thalgott et al. |
| 2011/0172716 A1 | 7/2011 | Glerum |
| 2011/0172774 A1 | 7/2011 | Varela |
| 2011/0184415 A1 | 7/2011 | Anderson et al. |
| 2011/0190892 A1 | 8/2011 | Kirschman |
| 2011/0202136 A1 | 8/2011 | Brittan et al. |
| 2011/0208311 A1 | 8/2011 | Janowski |
| 2011/0213421 A1 | 9/2011 | Binder et al. |
| 2011/0230970 A1 | 9/2011 | Lynn et al. |
| 2011/0230971 A1 | 9/2011 | Donner et al. |
| 2011/0238072 A1 | 9/2011 | Tyndall |
| 2011/0251689 A1 | 10/2011 | Seifert et al. |
| 2011/0270261 A1 | 11/2011 | Mast et al. |
| 2011/0270401 A1 | 11/2011 | McKay |
| 2011/0276142 A1 | 11/2011 | Niemiec et al. |
| 2011/0282453 A1 | 11/2011 | Greenhalgh et al. |
| 2011/0295371 A1 | 12/2011 | Moskowitz et al. |
| 2011/0301711 A1 | 12/2011 | Palmatier et al. |
| 2011/0301712 A1 | 12/2011 | Palmatier et al. |
| 2011/0301713 A1 | 12/2011 | Theofilos |
| 2011/0307010 A1 | 12/2011 | Pradhan |
| 2011/0313465 A1 | 12/2011 | Warren et al. |
| 2011/0319896 A1 | 12/2011 | Papenfuss et al. |
| 2011/0319898 A1 | 12/2011 | O'Neil et al. |
| 2011/0319998 A1 | 12/2011 | O'Neil et al. |
| 2011/0320000 A1 | 12/2011 | O'Neil |
| 2012/0004726 A1 | 1/2012 | Greenhalgh et al. |
| 2012/0004732 A1 | 1/2012 | Goel et al. |
| 2012/0022654 A1 | 1/2012 | Farris et al. |
| 2012/0023994 A1 | 2/2012 | Powell |
| 2012/0029636 A1 | 2/2012 | Ragab et al. |
| 2012/0041559 A1 | 2/2012 | Melkent et al. |
| 2012/0059474 A1 | 3/2012 | Weiman |
| 2012/0059475 A1 | 3/2012 | Weiman |
| 2012/0071977 A1 | 3/2012 | Oglaza et al. |
| 2012/0071980 A1 | 3/2012 | Purcell et al. |
| 2012/0078371 A1 | 3/2012 | Gamache et al. |
| 2012/0078372 A1 | 3/2012 | Gamache et al. |
| 2012/0078373 A1 | 3/2012 | Gamache et al. |
| 2012/0083887 A1 | 4/2012 | Purcell et al. |
| 2012/0083889 A1 | 4/2012 | Purcell et al. |
| 2012/0101581 A1 | 4/2012 | Mathieu et al. |
| 2012/0109309 A1 | 5/2012 | Mathieu et al. |
| 2012/0109310 A1 | 5/2012 | Mathieu et al. |
| 2012/0109311 A1 | 5/2012 | Mathieu et al. |
| 2012/0109312 A1 | 5/2012 | Mathieu et al. |
| 2012/0109313 A1 | 5/2012 | Mathieu et al. |
| 2012/0123546 A1 | 5/2012 | Medina |
| 2012/0136443 A1 | 5/2012 | Wenzel |
| 2012/0143336 A1 | 6/2012 | Aflatoon et al. |
| 2012/0150301 A1 | 6/2012 | Gamache et al. |
| 2012/0150303 A1 | 6/2012 | Linares |
| 2012/0150304 A1 | 6/2012 | Glerum et al. |
| 2012/0150305 A1 | 6/2012 | Glerum et al. |
| 2012/0158143 A1 | 6/2012 | Shapiro |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2012/0185049 A1 | 7/2012 | Varela |
| 2012/0191190 A1 | 7/2012 | Trieu |
| 2012/0197299 A1 | 8/2012 | Fabian, Jr. |
| 2012/0197401 A1 | 8/2012 | Duncan et al. |
| 2012/0197403 A1 | 8/2012 | Merves |
| 2012/0197405 A1 | 8/2012 | Cuevas et al. |
| 2012/0203230 A1 | 8/2012 | Adams |
| 2012/0203290 A1 | 8/2012 | Warren et al. |
| 2012/0203347 A1 | 8/2012 | Glerum et al. |
| 2012/0209331 A1 | 8/2012 | Michelson |
| 2012/0215262 A1 | 8/2012 | Culbert et al. |
| 2012/0215316 A1 | 8/2012 | Mohr et al. |
| 2012/0226319 A1 | 9/2012 | Armstrong et al. |
| 2012/0226357 A1 | 9/2012 | Varela |
| 2012/0232552 A1 | 9/2012 | Morgenstern et al. |
| 2012/0232658 A1 | 9/2012 | Morgenstern et al. |
| 2012/0253406 A1 | 10/2012 | Bae et al. |
| 2012/0265309 A1 | 10/2012 | Glerum et al. |
| 2012/0277795 A1 | 11/2012 | Von et al. |
| 2012/0277869 A1 | 11/2012 | Siccardi et al. |
| 2012/0290090 A1 | 11/2012 | Glerum et al. |
| 2012/0290097 A1 | 11/2012 | Cipoletti et al. |
| 2012/0310350 A1 | 12/2012 | Farris et al. |
| 2012/0310352 A1 | 12/2012 | Dimauro et al. |
| 2012/0323327 A1 | 12/2012 | McAfee |
| 2012/0323328 A1 | 12/2012 | Weiman |
| 2012/0330421 A1 | 12/2012 | Weiman |
| 2012/0330422 A1 | 12/2012 | Weiman |
| 2013/0006361 A1 | 1/2013 | Glerum et al. |
| 2013/0023993 A1 | 1/2013 | Weiman |

(56) References Cited

U.S. PATENT DOCUMENTS

| | | |
|---|---|---|
| 2013/0023994 A1 | 1/2013 | Glerum |
| 2013/0030536 A1 | 1/2013 | Rhoda et al. |
| 2013/0030544 A1 | 1/2013 | Studer |
| 2013/0041471 A1 | 2/2013 | Siegal et al. |
| 2013/0060337 A1 | 3/2013 | Petersheim et al. |
| 2013/0073044 A1 | 3/2013 | Gamache |
| 2013/0079883 A1 | 3/2013 | Butler et al. |
| 2013/0085572 A1 | 4/2013 | Glerum et al. |
| 2013/0085574 A1 | 4/2013 | Sledge |
| 2013/0103102 A1 | 4/2013 | Taylor et al. |
| 2013/0110240 A1 | 5/2013 | Hansell et al. |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0144391 A1* | 6/2013 | Siegal ............ A61F 2/442 623/17.16 |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0166027 A1 | 6/2013 | Bellas |
| 2013/0173004 A1 | 7/2013 | Greenhalgh et al. |
| 2013/0190875 A1 | 7/2013 | Shulock et al. |
| 2013/0190876 A1 | 7/2013 | Drochner et al. |
| 2013/0190877 A1 | 7/2013 | Medina |
| 2013/0204371 A1 | 8/2013 | McLuen et al. |
| 2013/0211525 A1 | 8/2013 | McLuen et al. |
| 2013/0211526 A1 | 8/2013 | Alheidt et al. |
| 2013/0218276 A1 | 8/2013 | Fiechter et al. |
| 2013/0238095 A1 | 9/2013 | Pavento et al. |
| 2013/0253585 A1 | 9/2013 | Garcia et al. |
| 2013/0261746 A1 | 10/2013 | Linares et al. |
| 2013/0268080 A1 | 10/2013 | Melkent et al. |
| 2013/0310939 A1 | 11/2013 | Fabian et al. |
| 2013/0325071 A1 | 12/2013 | Niemiec et al. |
| 2013/0325128 A1 | 12/2013 | Perloff et al. |
| 2013/0345813 A1 | 12/2013 | Frank et al. |
| 2014/0018816 A1 | 1/2014 | Fenn et al. |
| 2014/0025169 A1 | 1/2014 | Lechmann et al. |
| 2014/0039622 A1 | 2/2014 | Glerum et al. |
| 2014/0039623 A1 | 2/2014 | Iott et al. |
| 2014/0046333 A1 | 2/2014 | Johnson et al. |
| 2014/0046446 A1 | 2/2014 | Robinson |
| 2014/0058513 A1 | 2/2014 | Gahman et al. |
| 2014/0067069 A1 | 3/2014 | Lopez |
| 2014/0067073 A1 | 3/2014 | Hauck |
| 2014/0086962 A1 | 3/2014 | Jin et al. |
| 2014/0094916 A1 | 4/2014 | Glerum et al. |
| 2014/0100662 A1 | 4/2014 | Patterson |
| 2014/0107786 A1 | 4/2014 | Geisler et al. |
| 2014/0107790 A1 | 4/2014 | Combrowski |
| 2014/0114414 A1 | 4/2014 | Abdou et al. |
| 2014/0114415 A1 | 4/2014 | Tyber |
| 2014/0114423 A1 | 4/2014 | Suedkamp et al. |
| 2014/0128977 A1 | 5/2014 | Glerum et al. |
| 2014/0128980 A1 | 5/2014 | Kirschman |
| 2014/0135930 A1 | 5/2014 | Georges |
| 2014/0135934 A1 | 5/2014 | Hansell et al. |
| 2014/0142705 A1 | 5/2014 | Duffield et al. |
| 2014/0142706 A1 | 5/2014 | Hansell et al. |
| 2014/0156009 A1 | 6/2014 | Armstrong et al. |
| 2014/0163682 A1 | 6/2014 | Lott |
| 2014/0163683 A1 | 6/2014 | Seifert et al. |
| 2014/0172103 A1 | 6/2014 | O'Neil et al. |
| 2014/0172106 A1 | 6/2014 | To et al. |
| 2014/0180421 A1 | 6/2014 | Glerum et al. |
| 2014/0188225 A1 | 7/2014 | Dmuschewsky |
| 2014/0228959 A1 | 8/2014 | Niemiec et al. |
| 2014/0236296 A1 | 8/2014 | Wagner et al. |
| 2014/0243892 A1 | 8/2014 | Choinski |
| 2014/0243981 A1 | 8/2014 | Davenport et al. |
| 2014/0243982 A1 | 8/2014 | Miller |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0257494 A1 | 9/2014 | Thorwarth et al. |
| 2014/0277139 A1 | 9/2014 | Vrionis et al. |
| 2014/0277204 A1 | 9/2014 | Sandhu |
| 2014/0277464 A1 | 9/2014 | Richter et al. |
| 2014/0277474 A1 | 9/2014 | Robinson et al. |
| 2014/0277476 A1 | 9/2014 | McLean et al. |
| 2014/0277481 A1 | 9/2014 | Lee et al. |
| 2014/0303731 A1 | 10/2014 | Glerum |
| 2014/0303732 A1 | 10/2014 | Rhoda et al. |
| 2014/0324171 A1 | 10/2014 | Glerum et al. |
| 2014/0336771 A1 | 11/2014 | Zambiasi et al. |
| 2014/0364917 A1 | 12/2014 | Sandstrom et al. |
| 2015/0012097 A1 | 1/2015 | Ibarra et al. |
| 2015/0012098 A1 | 1/2015 | Eastlack et al. |
| 2015/0045894 A1 | 2/2015 | Hawkins et al. |
| 2015/0066145 A1 | 3/2015 | Rogers et al. |
| 2015/0088256 A1 | 3/2015 | Ballard |
| 2015/0094610 A1 | 4/2015 | Morgenstern et al. |
| 2015/0094812 A1 | 4/2015 | Cain |
| 2015/0094813 A1 | 4/2015 | Lechmann et al. |
| 2015/0100128 A1 | 4/2015 | Glerum et al. |
| 2015/0112396 A1 | 4/2015 | Willert et al. |
| 2015/0112398 A1 | 4/2015 | Morgenstern et al. |
| 2015/0112437 A1 | 4/2015 | Davis et al. |
| 2015/0112438 A1 | 4/2015 | McLean |
| 2015/0157470 A1 | 6/2015 | Voellmicke et al. |
| 2015/0164655 A1 | 6/2015 | Dimauro |
| 2015/0173914 A1 | 6/2015 | Dimauro et al. |
| 2015/0173916 A1 | 6/2015 | Cain |
| 2015/0182347 A1 | 7/2015 | Robinson |
| 2015/0190242 A1 | 7/2015 | Blain et al. |
| 2015/0196401 A1 | 7/2015 | Dimauro et al. |
| 2015/0202052 A1 | 7/2015 | Dimauro |
| 2015/0216671 A1 | 8/2015 | Cain |
| 2015/0216672 A1 | 8/2015 | Cain |
| 2015/0216673 A1 | 8/2015 | Dimauro |
| 2015/0230929 A1* | 8/2015 | Lorio ............ A61F 2/447 623/17.16 |
| 2015/0230932 A1 | 8/2015 | Schaller |
| 2015/0238324 A1 | 8/2015 | Nebosky et al. |
| 2015/0250606 A1 | 9/2015 | McLean |
| 2015/0257892 A1 | 9/2015 | Lechmann et al. |
| 2015/0297356 A1 | 10/2015 | Gamache et al. |
| 2015/0313721 A1 | 11/2015 | Gamache et al. |
| 2015/0320571 A1 | 11/2015 | Lechmann et al. |
| 2015/0374511 A1 | 12/2015 | Pavento et al. |
| 2016/0000577 A1 | 1/2016 | Dimauro |
| 2016/0016309 A1 | 1/2016 | Swift et al. |
| 2016/0022437 A1 | 1/2016 | Kelly et al. |
| 2016/0038301 A1 | 2/2016 | Wickham |
| 2016/0038304 A1 | 2/2016 | Aquino et al. |
| 2016/0045325 A1 | 2/2016 | Bellas et al. |
| 2016/0045333 A1 | 2/2016 | Baynham |
| 2016/0051376 A1 | 2/2016 | Serhan et al. |
| 2016/0058573 A1 | 3/2016 | Dimauro et al. |
| 2016/0067055 A1 | 3/2016 | Hawkins et al. |
| 2016/0074170 A1 | 3/2016 | Rogers et al. |
| 2016/0074175 A1 | 3/2016 | O'Neil |
| 2016/0081814 A1 | 3/2016 | Baynham |
| 2016/0089247 A1 | 3/2016 | Nichols et al. |
| 2016/0100954 A1 | 4/2016 | Rumi et al. |
| 2016/0106551 A1 | 4/2016 | Grimberg et al. |
| 2016/0113776 A1 | 4/2016 | Capote |
| 2016/0120662 A1 | 5/2016 | Schaller |
| 2016/0128843 A1 | 5/2016 | Tsau et al. |
| 2016/0128846 A1 | 5/2016 | Voellmicke |
| 2016/0199195 A1* | 7/2016 | Hauck ............ A61F 2/4455 623/17.16 |
| 2016/0199196 A1 | 7/2016 | Serhan et al. |
| 2016/0213487 A1 | 7/2016 | Wilson et al. |
| 2016/0228258 A1 | 8/2016 | Schaller et al. |
| 2016/0235455 A1 | 8/2016 | Wahl |
| 2016/0242929 A1 | 8/2016 | Voellmicke et al. |
| 2016/0256291 A1 | 9/2016 | Miller |

(56) References Cited

U.S. PATENT DOCUMENTS

| | | | |
|---|---|---|---|
| 2016/0296342 A1 | 10/2016 | Woods |
| 2016/0310296 A1 | 10/2016 | Dimauro et al. |
| 2016/0317313 A1 | 11/2016 | Dimauro |
| 2016/0317317 A1 | 11/2016 | Marchek et al. |
| 2016/0317714 A1 | 11/2016 | Dimauro et al. |
| 2016/0324660 A1 | 11/2016 | Pavento et al. |
| 2016/0324662 A1 | 11/2016 | McDonough et al. |
| 2016/0331541 A1 | 11/2016 | Dimauro et al. |
| 2016/0331546 A1 | 11/2016 | Lechmann et al. |
| 2016/0331548 A1 | 11/2016 | Dimauro et al. |
| 2016/0338854 A1 | 11/2016 | Serhan et al. |
| 2016/0367265 A1 | 12/2016 | Morgenstern Lopez |
| 2016/0367380 A1 | 12/2016 | Dimauro |
| 2016/0374821 A1 | 12/2016 | Dimauro et al. |
| 2017/0000622 A1 | 1/2017 | Thommen et al. |
| 2017/0035578 A1 | 2/2017 | Dimauro et al. |
| 2017/0056179 A1 | 3/2017 | Lorio |
| 2017/0065427 A1 | 3/2017 | Songer |
| 2017/0100177 A1* | 4/2017 | Kim .............. A61B 17/7032 |
| 2017/0100255 A1 | 4/2017 | Hleihil et al. |
| 2017/0100260 A1 | 4/2017 | Duffield et al. |
| 2017/0128226 A1 | 5/2017 | Faulhaber |
| 2017/0290674 A1 | 10/2017 | Olmos et al. |
| 2017/0304068 A1 | 10/2017 | Bellas et al. |
| 2017/0304074 A1 | 10/2017 | Dimauro et al. |
| 2017/0312090 A1 | 11/2017 | Sharabani et al. |
| 2018/0055649 A1 | 3/2018 | Kelly et al. |
| 2018/0078379 A1 | 3/2018 | Serhan et al. |
| 2018/0161171 A1 | 6/2018 | Frasier et al. |
| 2018/0161175 A1 | 6/2018 | Frasier et al. |
| 2019/0083276 A1 | 3/2019 | Dimauro |
| 2019/0105171 A1 | 4/2019 | Rogers et al. |
| 2020/0008950 A1 | 1/2020 | Serhan et al. |
| 2020/0015982 A1 | 1/2020 | O'Neil |
| 2020/0060843 A1 | 2/2020 | Evans et al. |

FOREIGN PATENT DOCUMENTS

| | | |
|---|---|---|
| CN | 1177918 A | 4/1998 |
| CN | 101073513 A | 11/2007 |
| CN | 101087566 A | 12/2007 |
| CN | 201244104 Y | 5/2009 |
| CN | 101631516 A | 1/2010 |
| CN | 101909548 A | 12/2010 |
| CN | 102164552 A | 8/2011 |
| DE | 2804936 A1 | 8/1979 |
| DE | 3023353 A1 | 4/1981 |
| DE | 3245055 A1 | 6/1984 |
| DE | 3911610 A1 | 10/1990 |
| DE | 4012622 C1 | 7/1991 |
| DE | 19543651 A1 | 7/1997 |
| DE | 19710392 C1 | 7/1999 |
| DE | 19832798 C1 | 11/1999 |
| DE | 20101793 U1 | 5/2001 |
| DE | 202006005868 U1 | 6/2006 |
| DE | 202008001079 U1 | 3/2008 |
| EP | 0077159 A1 | 4/1983 |
| EP | 0196409 A1 | 10/1986 |
| EP | 0260044 A1 | 3/1988 |
| EP | 0270704 A1 | 6/1988 |
| EP | 0282161 A1 | 9/1988 |
| EP | 0302719 A1 | 2/1989 |
| EP | 0433717 A1 | 6/1991 |
| EP | 0525352 A1 | 2/1993 |
| EP | 0529275 A2 | 3/1993 |
| EP | 0611557 A2 | 8/1994 |
| EP | 0621020 A1 | 10/1994 |
| EP | 0625336 A2 | 11/1994 |
| EP | 0678489 A1 | 10/1995 |
| EP | 0743045 A2 | 11/1996 |
| EP | 0841491 A1 | 5/1998 |
| EP | 0853929 A2 | 7/1998 |
| EP | 0974319 A2 | 1/2000 |
| EP | 1046376 A1 | 10/2000 |
| EP | 1103236 A2 | 5/2001 |
| EP | 1157676 A1 | 11/2001 |
| EP | 1290985 A2 | 3/2003 |
| EP | 1374784 A1 | 1/2004 |
| EP | 1378205 A1 | 1/2004 |
| EP | 1391189 A1 | 2/2004 |
| EP | 1470803 A1 | 10/2004 |
| EP | 1532949 A1 | 5/2005 |
| EP | 1541096 A1 | 6/2005 |
| EP | 1609444 A1 | 12/2005 |
| EP | 1385449 B1 | 7/2006 |
| EP | 1683490 A2 | 7/2006 |
| EP | 1683593 A2 | 7/2006 |
| EP | 1698305 A1 | 9/2006 |
| EP | 1774926 A2 | 4/2007 |
| EP | 1459711 B1 | 7/2007 |
| EP | 1843723 A1 | 10/2007 |
| EP | 1845874 A1 | 10/2007 |
| EP | 1847240 A1 | 10/2007 |
| EP | 1857064 A1 | 11/2007 |
| EP | 1924227 A2 | 5/2008 |
| EP | 1925272 | 5/2008 |
| EP | 1506753 B1 | 9/2009 |
| EP | 2331023 A2 | 6/2011 |
| EP | 2368529 A1 | 9/2011 |
| EP | 2237748 B1 | 9/2012 |
| EP | 2641571 A1 | 9/2013 |
| EP | 2699065 A1 | 2/2014 |
| EP | 2705809 A1 | 3/2014 |
| EP | 2764851 A1 | 8/2014 |
| FR | 2649311 A1 | 1/1991 |
| FR | 2699065 A1 | 6/1994 |
| FR | 2712486 A1 | 5/1995 |
| FR | 2718635 A1 | 10/1995 |
| FR | 2728778 A1 | 7/1996 |
| FR | 2730159 A1 | 8/1996 |
| FR | 2738142 A1 | 3/1997 |
| FR | 2745709 A1 | 9/1997 |
| FR | 2800601 A1 | 5/2001 |
| FR | 2801189 A1 | 5/2001 |
| FR | 2808182 A1 | 11/2001 |
| FR | 2874814 A1 | 3/2006 |
| FR | 2894130 A1 | 6/2007 |
| FR | 2913331 A1 | 9/2008 |
| GB | 0457673 A | 12/1936 |
| GB | 2157788 A | 10/1985 |
| GB | 2173565 A | 10/1986 |
| GB | 2220729 A | 1/1990 |
| GB | 2457673 A | 8/2009 |
| JP | 06-452439 A | 2/1989 |
| JP | 64-052439 A | 2/1989 |
| JP | 6452439 A | 2/1989 |
| JP | 06-500039 A | 1/1994 |
| JP | 06-292686 A | 10/1994 |
| JP | 06-319742 A | 11/1994 |
| JP | 07-502419 A | 3/1995 |
| JP | 07-184922 A | 7/1995 |
| JP | 10-085232 A | 4/1998 |
| JP | 1085232 A | 4/1998 |
| JP | 11-089854 A | 4/1999 |
| JP | 11-504550 A | 4/1999 |
| JP | 2002-516698 A | 6/2002 |
| JP | 2002-195226 A | 7/2002 |
| JP | 2003-010197 A | 1/2003 |
| JP | 2003-126266 A | 5/2003 |
| JP | 2003-526457 A | 9/2003 |
| JP | 2005-523732 A | 8/2005 |
| JP | 2006-507090 A | 3/2006 |
| JP | 2006-516456 | 7/2006 |
| JP | 2006-524114 A | 10/2006 |
| JP | 2007-054666 A | 3/2007 |
| JP | 2007-516808 | 6/2007 |
| JP | 2008-126085 A | 6/2008 |
| JP | 2011-509766 A | 3/2011 |
| JP | 2011-520580 A | 7/2011 |
| JP | 2012-020153 A | 2/2012 |
| JP | 2012-508044 | 4/2012 |
| JP | 4988203 B2 | 8/2012 |
| JP | 5164571 B2 | 3/2013 |
| WO | 91/09572 A1 | 7/1991 |

(56) References Cited

FOREIGN PATENT DOCUMENTS

| | | |
|---|---|---|
| WO | 93/04634 A1 | 3/1993 |
| WO | 93/04652 A1 | 3/1993 |
| WO | 93/17669 A1 | 9/1993 |
| WO | 94/04100 A1 | 3/1994 |
| WO | 94/23654 A1 | 10/1994 |
| WO | 95/31158 | 11/1995 |
| WO | 96/28100 A1 | 9/1996 |
| WO | 97/00054 A1 | 1/1997 |
| WO | 97/20526 A1 | 6/1997 |
| WO | 97/26847 A1 | 7/1997 |
| WO | 97/37620 A1 | 10/1997 |
| WO | 98/04217 A1 | 2/1998 |
| WO | 98/34552 A1 | 8/1998 |
| WO | 98/34568 A1 | 8/1998 |
| WO | 99/02214 A1 | 1/1999 |
| WO | 99/27864 A2 | 6/1999 |
| WO | 99/38463 A2 | 8/1999 |
| WO | 99/42062 A1 | 8/1999 |
| WO | 99/52473 A1 | 10/1999 |
| WO | 99/52478 A1 | 10/1999 |
| WO | 99/53871 A1 | 10/1999 |
| WO | 99/62417 A1 | 12/1999 |
| WO | 99/63914 A1 | 12/1999 |
| WO | 00/04851 A1 | 2/2000 |
| WO | 00/12033 | 3/2000 |
| WO | 00/13620 A1 | 3/2000 |
| WO | 2000/011355 A1 | 3/2000 |
| WO | 00/67652 | 5/2000 |
| WO | 00/44288 A1 | 8/2000 |
| WO | 00/53127 A1 | 9/2000 |
| WO | 00/67650 A1 | 11/2000 |
| WO | 00/67651 A1 | 11/2000 |
| WO | 00/74605 A1 | 12/2000 |
| WO | 00/76409 A1 | 12/2000 |
| WO | 01/01893 A1 | 1/2001 |
| WO | 01/01894 A1 | 1/2001 |
| WO | 01/01895 A1 | 1/2001 |
| WO | 01/08864 A1 | 2/2001 |
| WO | 01/12054 A2 | 2/2001 |
| WO | 01/15638 A1 | 3/2001 |
| WO | 01/17464 A1 | 3/2001 |
| WO | 01/68004 A2 | 9/2001 |
| WO | 01/80751 A1 | 11/2001 |
| WO | 02/13732 A2 | 2/2002 |
| WO | 02/17824 A2 | 3/2002 |
| WO | 02/17825 A2 | 3/2002 |
| WO | 02/30338 A1 | 4/2002 |
| WO | 02/43601 A2 | 6/2002 |
| WO | 02/43628 A1 | 6/2002 |
| WO | 02/47563 A1 | 6/2002 |
| WO | 02/71921 A2 | 9/2002 |
| WO | 02/76335 A2 | 10/2002 |
| WO | 02/80819 | 10/2002 |
| WO | 02/85250 A2 | 10/2002 |
| WO | 03/02021 A2 | 1/2003 |
| WO | 03/03951 A1 | 1/2003 |
| WO | 03/05937 A1 | 1/2003 |
| WO | 03/05938 A1 | 1/2003 |
| WO | 03/05939 A2 | 1/2003 |
| WO | 03/07854 A1 | 1/2003 |
| WO | 03/20169 A2 | 3/2003 |
| WO | 03/21308 A2 | 3/2003 |
| WO | 03/22165 A1 | 3/2003 |
| WO | 03/28587 A2 | 4/2003 |
| WO | 03/43488 A2 | 5/2003 |
| WO | 03/47473 A2 | 6/2003 |
| WO | 2003/051557 A1 | 6/2003 |
| WO | 03/57055 A1 | 7/2003 |
| WO | 03/57088 A1 | 7/2003 |
| WO | 03/70128 A1 | 8/2003 |
| WO | 03/90650 A1 | 11/2003 |
| WO | 2003/101308 A1 | 12/2003 |
| WO | 2004/008949 A2 | 1/2004 |
| WO | 03/59180 A2 | 3/2004 |
| WO | 2004/034924 A2 | 4/2004 |
| WO | 2004/043278 A1 | 5/2004 |
| WO | 2004/047691 A1 | 6/2004 |
| WO | 2004/062505 A1 | 7/2004 |
| WO | 2004/064603 A2 | 8/2004 |
| WO | 2004/069106 A1 | 8/2004 |
| WO | 2004/073563 A2 | 9/2004 |
| WO | 2004/078220 A2 | 9/2004 |
| WO | 2004/078221 A2 | 9/2004 |
| WO | 2004/079221 A1 | 9/2004 |
| WO | 2004/082526 A2 | 9/2004 |
| WO | 04/93749 A1 | 11/2004 |
| WO | 2004/098420 A2 | 11/2004 |
| WO | 2004/098453 A2 | 11/2004 |
| WO | 2004/108022 A1 | 12/2004 |
| WO | 2005/020861 A1 | 3/2005 |
| WO | 2005/027734 A2 | 3/2005 |
| WO | 2005/032433 A2 | 4/2005 |
| WO | 2005/039455 A1 | 5/2005 |
| WO | 2005/051246 A2 | 6/2005 |
| WO | 2005/069106 A1 | 7/2005 |
| WO | 2005/081877 A2 | 9/2005 |
| WO | 2005/112834 A2 | 12/2005 |
| WO | 2005/112835 A2 | 12/2005 |
| WO | 2006/017507 A2 | 2/2006 |
| WO | 2006/047587 A2 | 5/2006 |
| WO | 2006/047645 A2 | 5/2006 |
| WO | 2006/060420 A1 | 6/2006 |
| WO | 2006/063083 A1 | 6/2006 |
| WO | 2006/065419 A2 | 6/2006 |
| WO | 2006/066228 A2 | 6/2006 |
| WO | 2006/072941 A2 | 7/2006 |
| WO | 2006/081843 A1 | 8/2006 |
| WO | 2006/084057 A1 | 8/2006 |
| WO | 2006/058281 A3 | 10/2006 |
| WO | 2006/108067 A2 | 10/2006 |
| WO | 2006/119088 A2 | 11/2006 |
| WO | 2007/003785 A1 | 1/2007 |
| WO | 2007/009107 A2 | 1/2007 |
| WO | 2007/022194 A2 | 2/2007 |
| WO | 2007/028098 A2 | 3/2007 |
| WO | 2007/048012 A2 | 4/2007 |
| WO | 2007/065993 A2 | 6/2007 |
| WO | 2007/067726 A2 | 6/2007 |
| WO | 2007/070751 A1 | 6/2007 |
| WO | 2007/079021 A2 | 7/2007 |
| WO | 2007/084427 A2 | 7/2007 |
| WO | 2007/098288 A2 | 8/2007 |
| WO | 2007/118856 A1 | 10/2007 |
| WO | 2007/119212 A2 | 10/2007 |
| WO | 2007/124130 A2 | 11/2007 |
| WO | 2007/133410 A2 | 11/2007 |
| WO | 2008/004057 A2 | 1/2008 |
| WO | 2008/044057 A1 | 4/2008 |
| WO | 2008/064842 A2 | 6/2008 |
| WO | 2008/070863 A2 | 6/2008 |
| WO | 2008/103781 A2 | 8/2008 |
| WO | 2008/103832 A2 | 8/2008 |
| WO | 2008/149223 A2 | 12/2008 |
| WO | 2009/025841 A1 | 2/2009 |
| WO | 2009/064644 A1 | 5/2009 |
| WO | 2009/064787 A2 | 5/2009 |
| WO | 2009/079329 A2 | 6/2009 |
| WO | 2009/091775 A2 | 7/2009 |
| WO | 2009/092102 A1 | 7/2009 |
| WO | 2009/124269 A1 | 10/2009 |
| WO | 2009/136009 A1 | 11/2009 |
| WO | 2009/143496 A1 | 11/2009 |
| WO | 2009/147527 A2 | 12/2009 |
| WO | 2009/152919 A1 | 12/2009 |
| WO | 2010/028045 A1 | 3/2010 |
| WO | 2010/033786 A2 | 3/2010 |
| WO | 2010/054208 A1 | 5/2010 |
| WO | 2010/068725 A2 | 6/2010 |
| WO | 2010/088766 A1 | 8/2010 |
| WO | 2010/092893 A1 | 8/2010 |
| WO | 2010/099239 A2 | 9/2010 |
| WO | 2010/121028 A2 | 10/2010 |
| WO | 2010/136170 A1 | 12/2010 |
| WO | 2010/148112 A1 | 12/2010 |

(56) References Cited

FOREIGN PATENT DOCUMENTS

| | | |
|---|---|---|
| WO | 2011/005788 A1 | 1/2011 |
| WO | 2011/008864 A1 | 1/2011 |
| WO | 2011/035126 A1 | 3/2011 |
| WO | 2011/046459 A1 | 4/2011 |
| WO | 2011/046460 A1 | 4/2011 |
| WO | 2011/079910 A2 | 7/2011 |
| WO | 2011/080535 A1 | 7/2011 |
| WO | 2011/119617 A1 | 9/2011 |
| WO | 2011/142761 A1 | 11/2011 |
| WO | 2011/150350 A1 | 12/2011 |
| WO | 2012/009152 A1 | 1/2012 |
| WO | 2012/028182 A1 | 3/2012 |
| WO | 2012/030331 A1 | 3/2012 |
| WO | 2012/047712 | 4/2012 |
| WO | 2012/056119 A1 | 5/2012 |
| WO | 2012/089317 A1 | 7/2012 |
| WO | 2012/122294 A1 | 9/2012 |
| WO | 2012/135764 A1 | 10/2012 |
| WO | 2013/006669 A2 | 1/2013 |
| WO | 2013/018062 A1 | 2/2013 |
| WO | 2013/023096 A1 | 2/2013 |
| WO | 2013/025876 A1 | 2/2013 |
| WO | 2013/043850 A2 | 3/2013 |
| WO | 2013/062903 A1 | 5/2013 |
| WO | 2013/082184 A1 | 6/2013 |
| WO | 2013/096192 A1 | 6/2013 |
| WO | 2013/158294 A1 | 10/2013 |
| WO | 2013/173767 A1 | 11/2013 |
| WO | 2013/184946 A1 | 12/2013 |
| WO | 2013/191979 A1 | 12/2013 |
| WO | 2014/014610 A1 | 1/2014 |
| WO | 2014/018098 A1 | 1/2014 |
| WO | 2014/026007 A1 | 2/2014 |
| WO | 2014/035962 A1 | 3/2014 |
| WO | 2014/088521 A2 | 6/2014 |
| WO | 2014/116891 A1 | 7/2014 |
| WO | 2014/144696 A1 | 9/2014 |
| WO | 2015/048997 A1 | 4/2015 |
| WO | 2016/069796 A1 | 5/2016 |
| WO | 2016/127139 A1 | 8/2016 |

OTHER PUBLICATIONS

Search Report dated Jan. 20, 2012 for EP07855287.
Schmiedberg, "Isolation and characterization of metallic wear debris from a dynamic intervertebral disc prosthesis", J. Biomed. Mater. Res., vol. 28, Issue 11, 1277-1288, Nov. 1994.
Samandouras, "A New Anterior Cervical Instrumentation System Combining an Intradiscal Cage With an Integrated Plate", Spine, vol. 26, No. 10, pp. 1188-1192, 2001, Lippincott Williams and Watkins, Inc.
Polymer Preprints (ACS Division of Polymer Chemistry), vol. 30(1), p. 498, 1989 by Cohn (e.g. PEO/PLA).
Pederson, "Thermal Assembly of a Biomimetic Mineral/Collagen Composite", Biomaterials, 2003, vol. 2, pp. 4881-4890, Elsevier.
Pavlov, "Good Outcome and Restoration of Lordosis After Anterior Lumbar Interbody Fusion With Additional Posterior Fixation", Spine, vol. 29, No. 17, pp. 1893-1900, 2004, Lippincott Williams & Wilkins.
Oxland, "A Comparative Biomechanical Investigation of Anterior Lumbar Interbody Cages: Central and Bilateral Approaches", The Journal of Bone and Joint Surgery, pp. 383-393, vol. 82A, No. 3, Mar. 2000.
Kemnitzer et al., "Degradable Polymers Derived From the Amino Acid L-Tyrozine", The Handbook of Biodegradable Polymers, edited by Domb, et al., Hardwood Academic Press, 1997, pp. 251-272.
Kandziora", Biomechanical Comparison of Cervical Spine Interbody Fusion Cages", Spine, vol. 26, No. 17, pp. 1850-1857, 2001, Lippincott Williams & Wilkins, Inc.
Journal of Biomaterials Research, vol. 22, pp. 993-1009, 1988 by Cohn and Younes.
Humphries, "Anterior Fusion of the Lumbar Spine Using an Internal Fixative Device", Surgical Forum, vol. IX, pp. 770-773, American College of Surgeons, 1959, Chicago Illinois.
Heller in Handbook of Biodegradable Polymers, edited by Domb, et al, Hardwood Academic Press, pp. 99-118 (1997).
Gercek, "Subsidence of Stand-Alone Cervical Cages in Anterior Interbody Fusion: Warning", Eur. Spine Journal, vol. 12, pp. 513-516, 2003, Springer-Verlag.
European Examination Report dated Mar. 19, 2014 for EP07855287.4.
Cain, "New Stand-Alone Anterior Lumbar Inerbody Fusion Device: Biomechanical Comparison with Established Fixation Techniques", Spine, vol. 30, No. 23, pp. 2631-2636, 2005, Lippincott Williams & Wilkins, Inc.
Allcock, "Polyphosphazenes", The Encyclopedia of Polymer Science, vol. 13, pp. 31-41, Wiley Intersciences, John Wiley & Sons, (1988).
Zucherman, "A Multicenter, Prospective, Randomized Trial Evaluating the X STOP Interspinous Process Decompression System for the Treatment of Neurogenic Intermittent Claudication", SPINE, vol. 30, No. 12, pp. 1351-1358, 2005.
Vikram Talwar, "Insertion loads of the X STOP Interspinous Process Distraction System Designed to Treat Neurogenic Intermittent Claudication", EUR SPINE J. (2006) 15: pp. 908-912.
U.S. Appl. No. 14/790,866, filed Jul. 2, 2015, entitled Expandable Implant.
U.S. Appl. No. 14/685,402, filed Apr. 13, 2015, entitled Expandable Intervertebral Implant.
U.S. Appl. No. 14/685,358, filed Apr. 13, 2015, entitled Expandable Intervertebral Implant.
U.S. Appl. No. 14/640,220, filed Mar. 6, 2015, entitled Expandable Intervertebral Implant.
U.S. Appl. No. 13/673,061, filed Nov. 6, 2012, entitled Interbody Device With Opening to Allow Packing Graft and Other Biologies.
U.S. Appl. No. 60/942,998, Method and Apparatus for Spinal Stabilization, filed Jun. 8, 2007.
U.S. Appl. No. 61/675,975, Expandable Implant, filed Jul. 26, 2012.
U.S. Appl. No. 60/397,588, Method and apparatus for spinal fixation, filed Jul. 19, 2002.
U.S. Appl. No. 60/794,171, Method and apparatus for spinal fixation, filed Apr. 21, 2006.
U.S. Appl. No. 60/424,055, Method and apparatus for spinal fixation, filed Nov. 5, 2002.
Talwar "Insertion loads of the X STOP interspinous process distraction system designed to treat neurogenic intermittent claudication", Eur Spine J. (2006) 15: pp. 908-912.
Spine Solutions Brochure—Prodisc 2001, 16 pages.
Siddiqui, "The Positional Magnetic Resonance Imaging Changes in the Lumbar Spine Following Insertion of a Novel Interspinous Process Distraction Device", Spine, vol. 30, No. 23, pp. 2677-2682, 2005.
Shin, "Posterior Lumbar Interbody Fusion via a Unilateral Approach", Yonsei Medical Journal, 2006, pp. 319-325, vol. 47(3).
ProMap TM EMG Navigation Probe. Technical Brochure Spineology Inc, Dated May 2009.
Polikeit, "The Importance of the Endplate for Interbody Cages in the Lumbar Spine", Eur. Spine J., 2003, pp. 556-561, vol. 12.
Niosi, "Biomechanical Characterization of the three-dimentional kinematic behavior of the dynesys dynamic stabilization system: an in vitro study", Eur Spine J. (2006), 15: pp. 913-922.
Morgenstern, "Transforaminal Endoscopic Stenosis Surgery—A Comparative Study of Laser and Reamed Foraminoplasty", in European Musculoskeletal Review, Issue 1, 2009.
Medco Forum, "Percutaneous Lumbar Fixation via PERPOS System From Interventional Spine", Oct. 2007, vol. 14, No. 49.
Medco Forum, "Percutaneous Lumbar Fixation Via PERPOS PLS System Interventional Spine", Sep. 2008, vol. 15, No. 37.
Mahar et al., "Biomechanical Comparison of Novel Percutaneous Transfacet Device and a Traditional Posterior System for Single Level Fusion", Journal of Spinal Disorders & Techniques, Dec. 2006, vol. 19, No. 8, pp. 591-594.
Link SB Charite Brochure—Intervertebral Prosthesis 1988, 29 pages.

(56) References Cited

OTHER PUBLICATIONS

Krbec, "Replacement of the Vertebral Body with an Expansion Implant (Synex)", Acta Chir Orthop Traumatol Cech, 2002, pp. 158-162, vol. 69(3).
King., "Internal Fixation for Lumbosacral Fusion", The Journal of Bone and Joint Surgery, J. Bone Joint Surg. Am., 1948; 30: 560-578.
Kambin et al., "Percutaneous Lateral Discectomy of the Lumbar Spine: A Preliminary Report", Clin. Orthop,: 1983, 174: 127-132.
Iprenburg et al., "Transforaminal Endocopic Surgery in Lumbar Disc Herniation in an Economic crises—The Tessys Method", US Musculoskeletal, 2008, pp. 47-49.
Hunt, "Expandable Cage Placement Via a Posterolateral Approach in Lumbar Spine Reconstructions", Journal of Neurosurgery: Spine, Sep. 2006, pp. 271-274, vol. 5.
https://emea.depuysynthes.com/hcp/hip/products/qs/porocoat-porous-coating-emea, Porocoat (Registered) Porous Coating, Depuy Synthes, webpage, accessed Jul. 5, 2016.
Gray's Anatomy, Crown Publishers, Inc., 1977, pp. 33-54.
Gore, "Technique of Cervical Interbody Fusion", Clinical Orthopaedics and Related Research, Sep. 1984, pp. 191-195, No. 188.
Fuchs, "The use of an interspinous implant in conjuction with a graded facetectomy procedure", Spine vol. 30, No. 11, pp. 1266-1272, 2005.
Folman, Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).
Chin, "Early Results of the Triage Medical Percutaneous Transfacet Pedicular BONE-LOK Compression Device for Lumbar Fusion", Accessed online Jul. 10, 2017, 10 pages.
Chiang, "Biomechanical Comparison of Instrumented Posterior Lumbar Interbody Fusion with One or Two Cages by Finite Element Analysis", Spine, Sep. 2006, pp. E682-E689, vol. 31(19), Lippincott Williams & Wilkins, Inc.
Brooks et al., "Efficacy of Supplemental Posterior Transfacet Pedicle Device Fixation in the Setting of One- or Two-Level Anterior Lumbar Interbody Fusion", Retrieved Jun. 19, 2017, 6 pages.
Brochure for PERPOS PLS System Surgical Technique by Interventional Spine, 2008, 8 pages.
Alfen et al., "Developments in the area of Endoscopic Spine Surgery", European Musculoskeletal Review 2006, pp. 23-24, ThessysTM, Transforaminal Endoscopic Spine Systems, joi max Medical Solutions.
Hoogland et al., "Total Lumar Intervertebral Disc Replacement: Testing a New Articulating Space in Human Cadaver Spines-24 1", Annual ORS, Dallas, TX, Feb. 21-23, 1978, 8 pages.
Bruder et al., Identification and characterization of a cell surface differentiation antigen on human osteoprogenitor cells. 42nd Annual Meeting of the Orthopaedic Research Society. p. 574, Feb. 19-22, 1996, Atlanta, Georgia.
Bruder et al., Monoclonal antibodies reactive with human osteogenic cell surface antigens. Bone. Sep. 1997;21 (3):225-235.
Burkoth et al., A review of photocrosslinked polyanhydrides: in situ forming degradable networks. Biomaterials. Dec. 2000; 21 (23): 2395-2404.
Cambridge Scientific News, FDA Approves Cambridge Scientific, Inc.'s Orthopedic WISORB (TM) Malleolar Screw [online], Jul. 30, 2002 [retrieved on Oct. 14, 2003]. Retrieved from the Internet <URL: http://www.cambridgescientificinc.com>.
Carrino, John A., Roxanne Chan and Alexander R. Vaccaro, "Vertebral Augmentation: Vertebroplasty and Kyphoplasty", Seminars in Roentgenology, vol. 39, No. 1 Jan. 2004: pp. 68-84.
Cheng, B.C., Ph.D., Biomechanical pullout strength and histology of Plasmapore Registered XP coated implants: Ovine multi time point survival study. Aesculap Implant Systems, LLC, 2013, 12 pages.
Edeland, H.G., "Some Additional Suggestions for an Intervertebral Disc Prosthesis", J of Bio Medical Engr., vol. 7(1) pp. 57-62, Jan. 1985.
European Search Report EP03253921 dated Nov. 13, 2003, 4 pages.

Flemming et al., Monoclonal anitbody against adult marrow-derived mesenchymal stem cells recognizes developing vasculature in embryonic human skin. Developmental Dynamics. 1998;212:119-132.
Ha et al. (Topographical characterization and microstructural interface analysis of vacuum-plasma-sprayed titanium and hydroxyapatite coatings on carbon fiber-reinforced poly(etheretherketone), Journal of Materials Science: Materials in Science 9 (1997), pp. 891-896.
Haas, Norbert P., New Products from AO Development [online], May 2002 [retrieved on Oct. 14, 2003]. Retrieved from the Internet <URL: http://www.ao.asif.ch/development/pdf_tk_news_02.pdf>.
Hao et al., Investigation of nanocomposites based on semi-interpenetrating network of [L-poly (epsilon-caprolactone)]/[net-poly (epsilon-caprolactone)] and hydroxyapatite nanocrystals. Biomaterials. Apr. 2003;24(9): 1531-9.
Harsha et al., Tribo performance of polyaryletherketone composites, Polymer Testing (21) (2002) pp. 697-709.
Haynesworth et al., Cell surface antigens on human marrow-derived mesenchymal cells are detected by monoclonal antibodies. Bone. 1992;13(1):69-80.
Hitchon et al., Comparison of the biomechanics of hydroxyapatite and polymethylmethacrylate vertebroplasty in a cadaveric spinal compression fracture model. J Neurosurg. Oct. 2001;95(2 Suppl):215-20.
Joshi, Ajeya P., M.D. and Paul A. Glazer, M.D., "Vertebroplasty: Current Concepts and Outlook for the Future", 2003, (5 pages), From: http://www.orthojournalhms.org/html/pdfs/manuscript-15.pdf.
Kandziora, Frank, et al., "Biomechanical Analysis of Biodegradable Interbody Fusion Cages Augmented with Poly (propylene Glycol-co-Fumaric Acid)," SPINE, 27(15): 1644-1651 (2002).
Kotsias, A., Clinical trial of titanium-coated PEEL cages anterior cervical discectomy and fusion. [Klinishe Untersuching zum Einsatz von titanbeschichteten Polyetheretherketon—Implantaten bei der cervikalen interkorporalen fusion]. Doctoral thesis. Department of Medicine, Charite, University of Medicine Berlin, 2014, 73 pages. (German language document/Engl. summary).
Kroschwitz et al., eds., Hydrogels. Concise Encyclopedia of Polymer Science and Engineering. Wiley and Sons, pp. 458-459, 1990.
Lendlein et al., AB-polymer networks based on oligo(epsilon-caprolactone) segments showing shape-memory properties. Proc Natl Acad Sci USA. Jan. 30, 2001;98(3):842-7. Epub Jan. 23, 2001.
Malberg. M.I., MD; Pimenta, L., MD; Millan, M.M., MD, 9th International Meeting on Advanced Spine Techniques, May 23-25, 2002, Montreux, Switzerland. Paper #54, Paper #60, and E-Poster #54, 5 pages.
McAfee et al., Minimally invasive anterior retroperitoneal approach to the lumbar spine: Emphasis on the lateral BAK. SPINE. 1998;23(13):1476-84.
Mendez et al., Self-curing acrylic formulations containing PMMA/PCL composites: properties and antibiotic release behavior. J Biomed Mater Res. Jul. 2002;61 (1 ):66-74.
Nguyen et al., Poly(Aryl-Ether-Ether-Ketone) and its Advanced Composites: A Review, Polymer Composites, Apr. 1987, vol. 8, No. 2, pp. 57-73.
OSTEOSET Registered DBM Pellets (Important Medical Information) [online], Nov. 2002 [retrieved on Oct. 14, 2003]. Retrieved from the Internet <URL: http://www.wmt.com/Literature>.
Regan et al., Endoscopic thoracic fusion cage. Atlas of Endoscopic Spine Surgery. Quality Medical Publishing, Inc. 1995;350-354.
Slivka et al., In vitro compression testing of fiber-reinforced, bioabsorbable, porous implants. Synthetic Bioabsorbable Polymers for Implants. STP1396, pp. 124-135, ATSM International, Jul. 2000.
Sonic Accelerated Fracture Healing System/Exogen 3000. Premarket Approval. U.S. Food & Drug Administration. Date believed to be May 10, 2000. Retrieved Jul. 23, 2012 from <http://www.accessdata.fda.gov/scripts/cdrh/cfdocs/cfPMA/pma.cfm?id=14736#>. 4 pages, 2012.
Stewart et al., Co-expression of the stro-1 anitgen and alkaline phosphatase in cultures of human bone and marrow cells. ASBMR 18th Annual Meeting. Bath Institute for Rheumatic Diseases, Bath, Avon, UK. Abstract No. P208, p. S142, 1996.

(56) References Cited

OTHER PUBLICATIONS

Timmer et al., In vitro degradation of polymeric networks of poly(propylene fumarate) and the crosslinking macromer poly(propylene fumarate)-diacrylate. Biomaterials. Feb. 2003;24(4 ):571-7.
United States Disctrict Court, Central District of California, Case No. 1 :10-CV-00849-LPS, Nuvasive, Inc., vs., Globus Medical, Inc., Videotaped Deposition of: Luiz Pimenta, M.D., May 9, 2012, 20 pages.
Walsh et al., Preparation of porous composite implant materials by in situ polymerization of porous apatite containing epsilon-caprolactone or methyl methacrylate. Biomaterials. Jun. 2001;22( 11):1205-12.
Zimmer.com, Longer BAK/L Sterile Interbody Fusion Devices. Date believed to be 1997. Product Data Sheet.Zimmer. Retrieved Jul. 23, 2012 from <http:/ catalog.zimmer.com/contenUzpc/products/ 600/600/620/S20/S045. html>, 2 pages.
International Patent Application No. PCT/US2013/029014, International Search Report dated Jul. 1, 2013, 2 pages.

\* cited by examiner

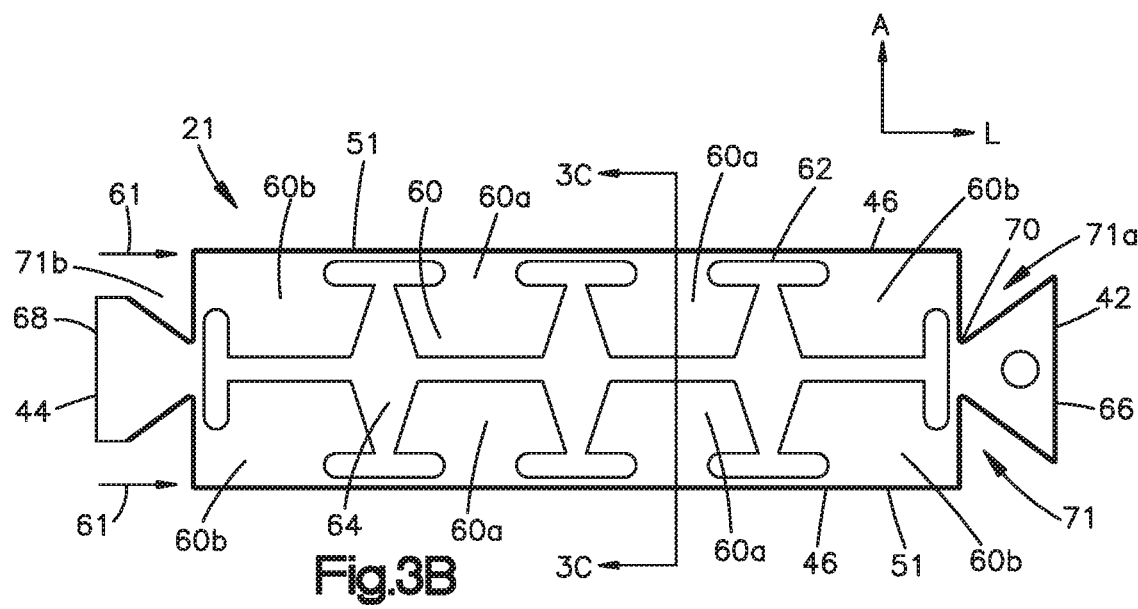
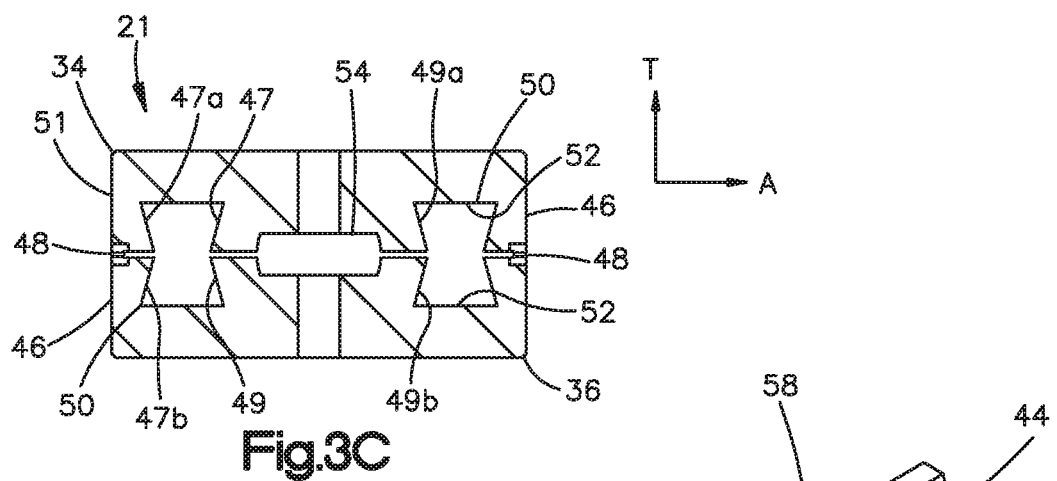
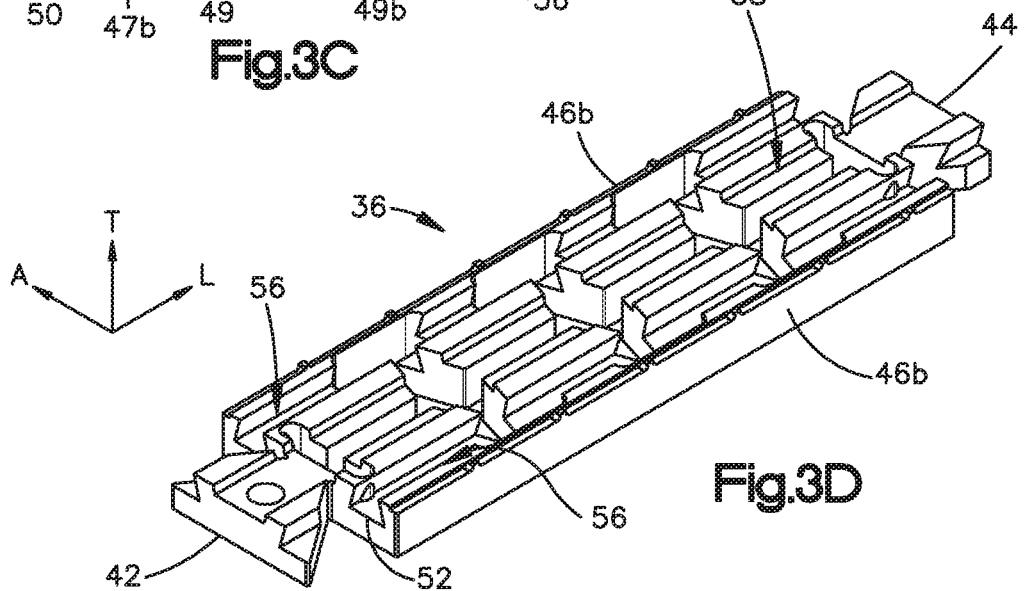

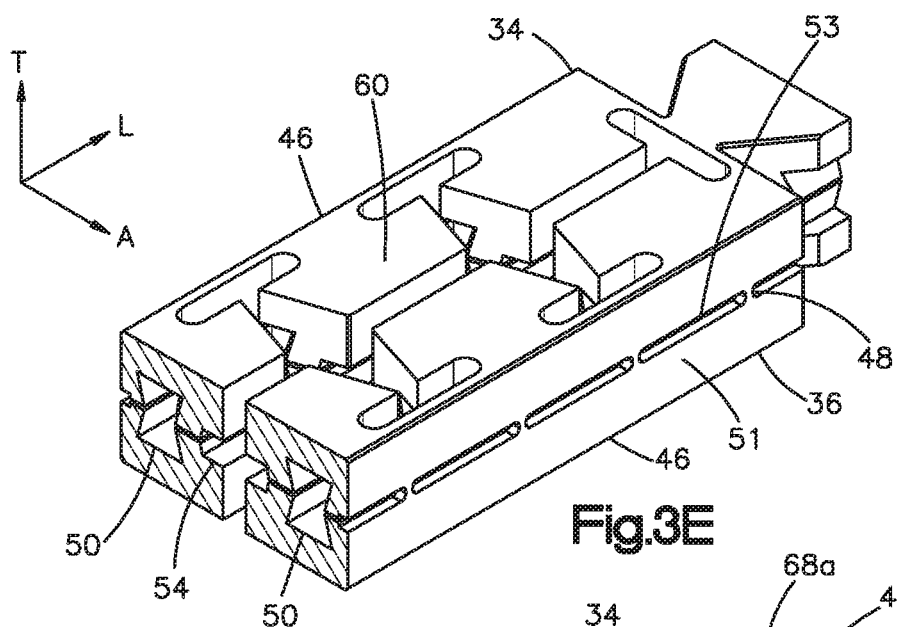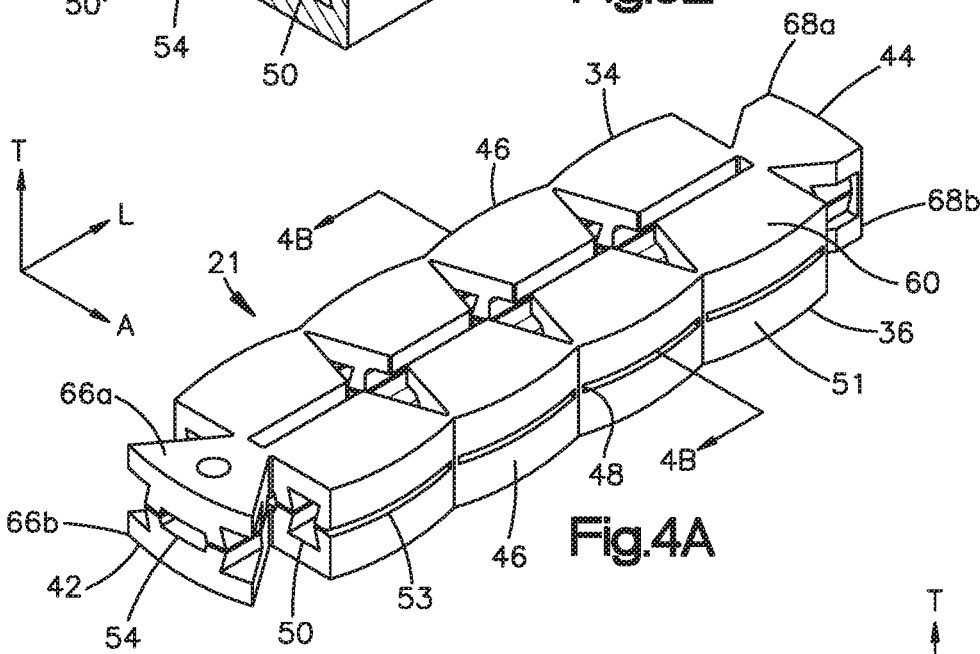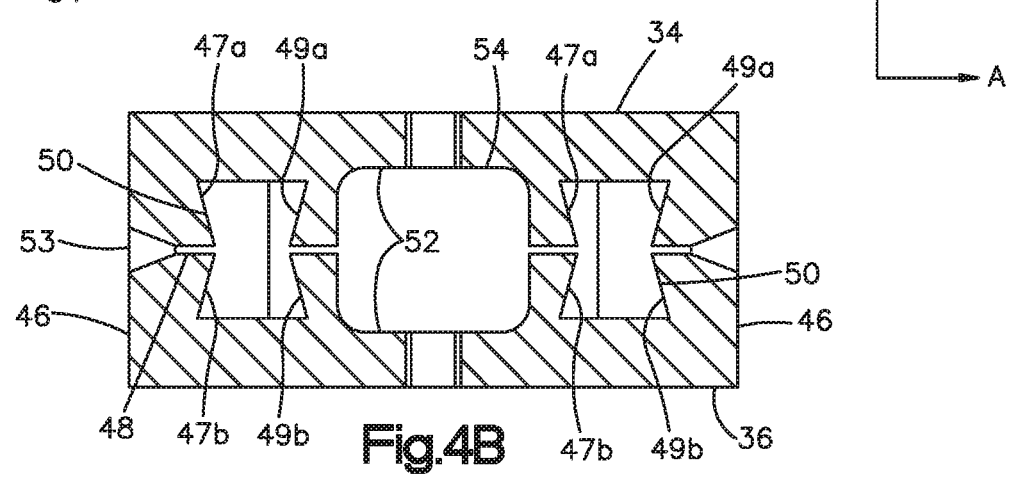

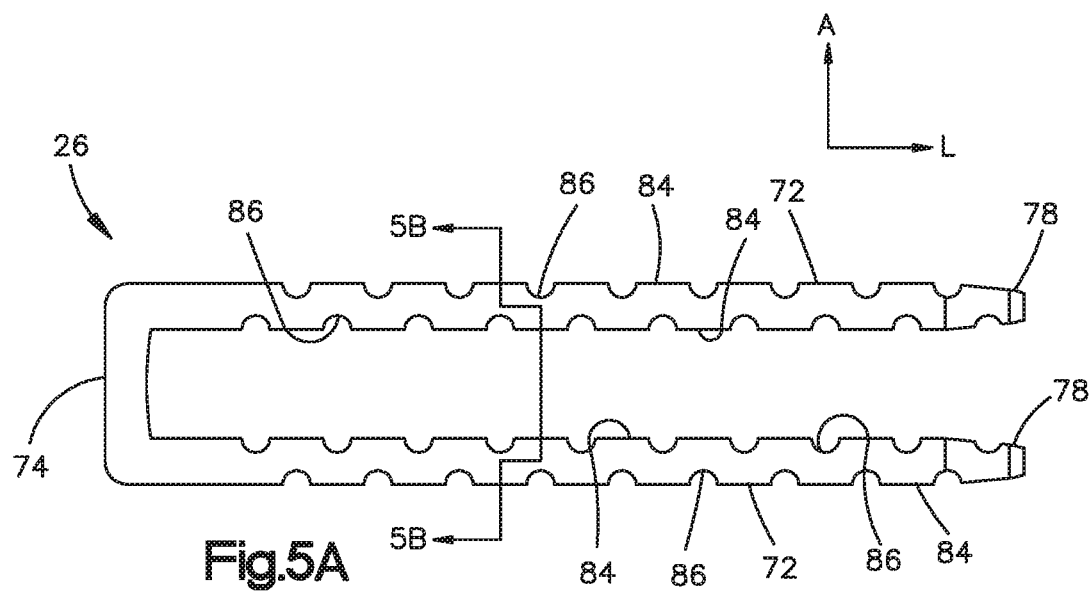
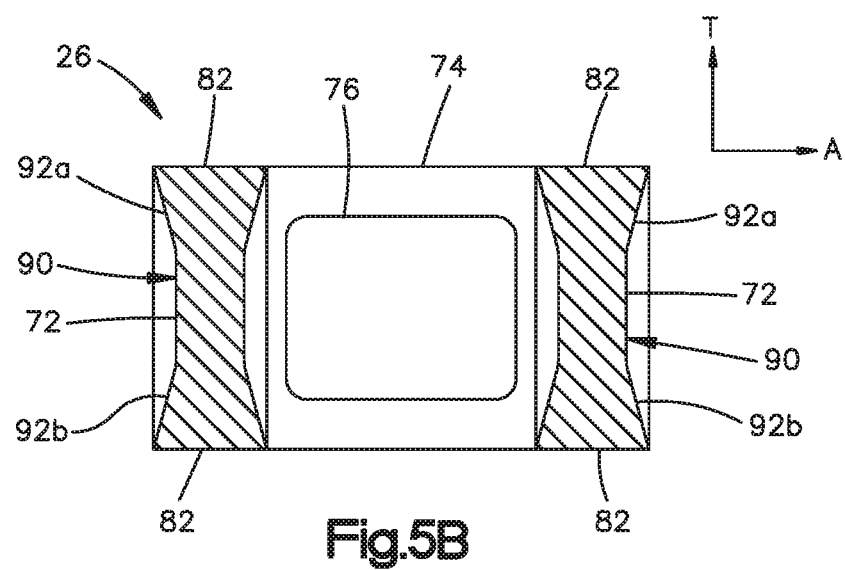

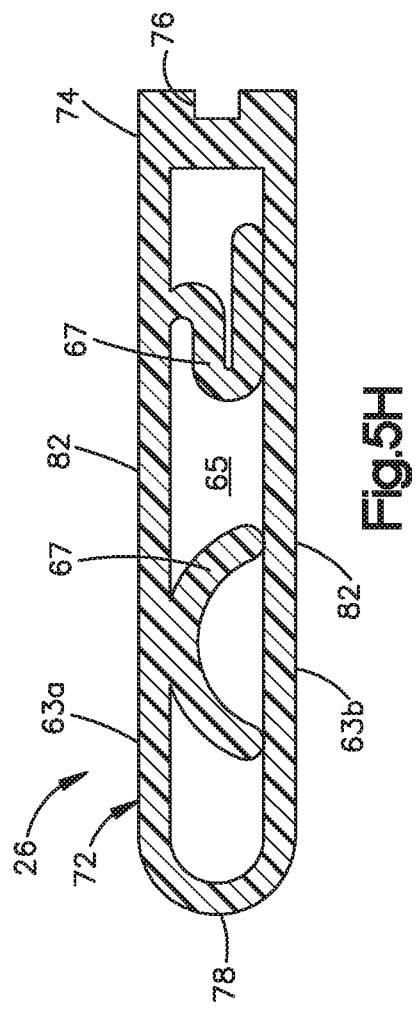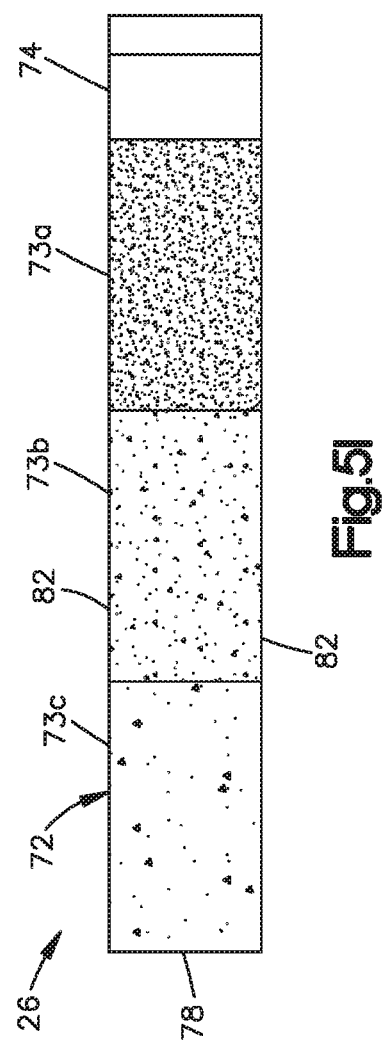

EXPANDABLE INTERVERTEBRAL FUSION CAGE

BACKGROUND

The human spine is comprised of a series of vertebral bodies separated by intervertebral discs. The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus within its cushioning qualities. These nucleus pulposus cells may also secrete small amounts of cytokines such as interleukin-1.beta. and TNF-.alpha. as well as matrix metalloproteinases ("MMPs"). These cytokines and MMPs help regulate the metabolism of the nucleus pulposus cells.

In some instances of degenerative disc disease (DDD), gradual degeneration of the intervertebral disc is caused by mechanical instabilities in other portions of the spine. In these instances, increased loads and pressures on the nucleus pulposus cause the cells within the disc (or invading macrophages) to emit larger than normal amounts of the above-mentioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of proinflammatory cytokines and/or MMPs that may cause nerve irritation and pain.

As DDD progresses, toxic levels of the cytokines and MMPs present in the nucleus pulposus begin to degrade the extracellular matrix. In particular, the MMPs (as mediated by the cytokines) begin cleaving the water-retaining portions of the proteoglycans, thereby reducing their water-retaining capabilities. This degradation leads to a less flexible nucleus pulposus, and so changes the loading pattern within the disc, thereby possibly causing delamination of the annulus fibrosis. These changes cause more mechanical instability, thereby causing the cells to emit even more cytokines, typically thereby upregulating MMPs. As this destructive cascade continues and DDD further progresses, the disc begins to bulge ("a herniated disc"), and then ultimately ruptures, causing the nucleus pulposus to contact the spinal cord and produce pain.

One proposed method of managing these problems is to remove the problematic disc and replace it with a porous device that restores disc height and allows for bone growth therethrough for the fusion of the adjacent vertebrae. These devices are commonly called "fusion devices".

One proposed method of managing these problems is to remove the problematic disc and replace it with a device that restores disc height and allows for bone growth between the adjacent vertebrae. These devices are commonly called fusion devices, or "interbody fusion devices". Current spinal fusion procedures include transforaminal lumbar interbody fusion (TLIF), posterior lumbar interbody fusion (PLIF), extraforaminal lumbar interbody fusion (ELIF), and extreme lateral interbody fusion (XLIF) procedures. However, implants having textured, toothed upper and lower vertebral engagement teeth can suffer from mechanical interference between the teeth and the bony endplates during implantation. On the other hand, while implants having smooth upper and lower vertebral engagement surfaces are easier to insert into the intervertebral space, such implants can suffer from undesirable migration in the disc space after implantation.

SUMMARY

In accordance with one aspect of the present disclosure, an intervertebral fusion cage can include a cage body that defines a leading end with respect to a direction of insertion into an intervertebral space, and a trailing end opposite the leading end along a longitudinal direction. The cage body can also define an upper vertebral contacting surface and a lower vertebral contacting surface spaced from the upper vertebral contacting surface along a transverse direction that is substantially perpendicular with respect to the longitudinal direction. The cage body can further include first and second side walls that extend between the leading end and the trailing end, the first and second side walls opposite each other along a lateral direction that is substantially perpendicular to each of the longitudinal direction and the transverse direction. The lower and upper vertebral contacting surfaces can be movable away from each other along the transverse direction so as to expand the intervertebral fusion cage from a first transverse position to an expanded transverse position. Further, at least respective portions of the first and second side walls can be movable away from each other different distances so as to expand the intervertebral fusion cage from a first lateral position to an expanded lateral position. In the expanded lateral position, the first and second side walls can be spaced from each other along the lateral direction a first distance at a first location spaced from both the trailing end and a midline between the leading end and the trailing end with respect to the longitudinal direction, and the first and second side walls can be spaced from each other along the lateral direction a second distance at a second location between the first location and the leading end, the second location is different than the first location. The second distance can be greater than the first distance.

BRIEF DESCRIPTION OF THE DRAWINGS

FIG. 3B is a top plan view of the fusion cage illustrated in FIG. 3A;

FIG. 3C is a sectional end elevation view of the fusion cage illustrated in FIG. 3B, taken along line 3C-3C;

FIG. 3D is a perspective view of body of the fusion cage illustrated in FIG. 3A;

FIG. 3E is a sectional perspective view of the fusion cage illustrated in FIG. 3A;

FIG. 4A is a perspective view of a fusion cage similar to the fusion cage illustrated in FIG. 3A, but shown constructed in accordance with an alternative embodiment;

FIG. 4B is a sectional end elevation view of the fusion cage illustrated in FIG. 4A;

FIG. 5A is a to plan view of a core in a first position configured for insertion into the fusion cage so as to expand the cage from the unexpanded transverse position illustrated in FIG. 1A to the expanded transverse position illustrated in FIG. 1B;

FIG. 5B is a sectional end elevation view of the core illustrated in FIG. 5A, taken along line 5B-5B;

FIG. 5H is a sectional side view of the core illustrated in FIG. 5A taken through one of the arms, but shown including spring members in accordance with one embodiment;

FIG. 5I is a side elevation view of the core illustrated in FIG. 5A, but shown having arms that include zones having different levels of stiffness in accordance with an alternative embodiment;

DETAILED DESCRIPTION OF THE INVENTION

Figure 1A:
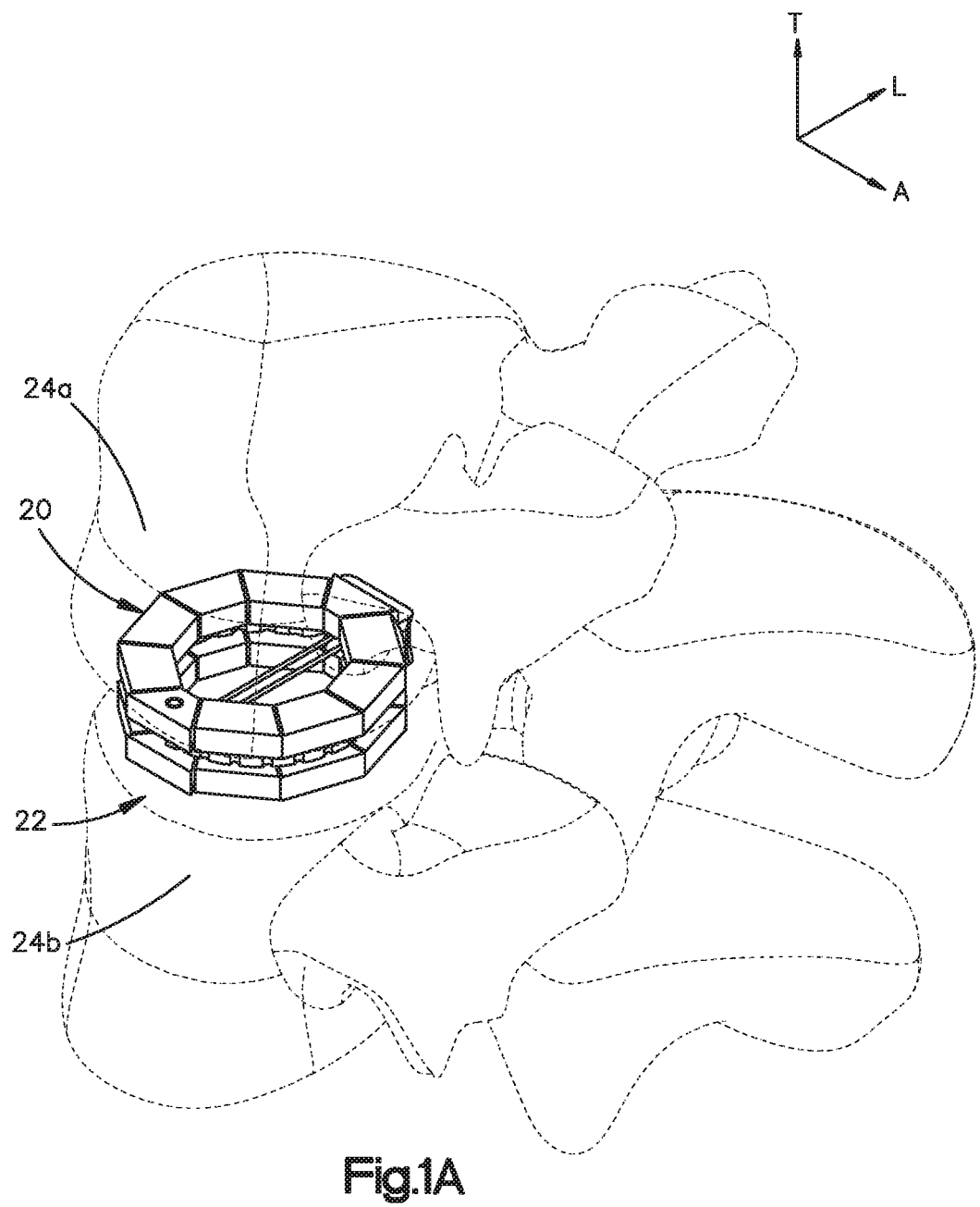
FIG. 1A is a perspective view of an expandable intervertebral fusion cage shown implanted in an intervertebral disc space in an expanded lateral position and an expanded transverse position.

Referring to FIG. 1A, an expandable intervertebral fusion cage 20 is shown installed into an intervertebral disc space 22 defined by a superior vertebra 24a and an adjacent, or neighboring, inferior vertebrae 24b. The expandable intervertebral fusion cage 20 can be configured to fuse with the vertebrae 24a and 24b. The vertebrae 24a and 24b can be anatomically adjacent vertebrae. Alternatively, the vertebrae 24a and 24b can be disposed adjacent each other following a corpectomy or hemicorpectomy. The vertebrae 24a and 24b can be lumbar vertebrae that define an anterior side AS, an opposing posterior side PS. The vertebrae 24a and 24b further define opposing lateral sides LS that are disposed on opposing sides of a central medial axis M-M that extends along a mediolateral direction. The vertebrae 24a and 24b are illustrated as being spaced along a caudocranial axis C-C. The expandable intervertebral fusion cage 20 has a length generally along a longitudinal direction L, a lateral direction A, and a transverse direction T.

Various structure is therefore described as oriented horizontally along a longitudinal direction "L" and lateral direction "A", and vertically along a transverse direction "T". The housing is elongate in the longitudinal direction L. Unless otherwise specified herein, the terms "lateral," "longitudinal," and "transverse" are used to describe the orthogonal directional components of various components. The directional terms "inboard" and "inner," "outboard" and "outer," and derivatives thereof are used herein with respect to a given apparatus to refer to directions along the directional component toward and away from the geometric center of the apparatus.

It should be appreciated that while the longitudinal and lateral directions are illustrated as oriented along a horizontal plane, and that the transverse direction is illustrated as oriented along a vertical plane, the planes that encompass the various directions may differ during use. Accordingly, the directional terms "vertical" and "horizontal" are used to describe the expandable intervertebral fusion cage 20 and its components as illustrated merely for the purposes of clarity and illustration.

The expandable intervertebral fusion cage 20 is configured to be inserted into the intervertebral disc space 22 along a TLIF approach. Accordingly, when the fusion cage 20 is implanted in the disc space 22, the longitudinal direction L can be oriented oblique with respect to the anterior-posterior direction, and oblique with respect to the medial-lateral direction an amount greater than with respect to the anterior-posterior direction. The transverse direction T can be oriented substantially in the caudocranial direction. It should be appreciated, however, that the fusion cage 20 can be inserted into the disc space 22 along any suitable direction as desired. Thus, the directions defined above by the expandable intervertebral implant 20, when implanted in the disc space 22, can alternatively be oriented at any desirable angle between 0° and 180° with respect to the various anatomical directions. For instance, the longitudinal and lateral directions of the implant could be oriented at any desirable angle between 0° and 180° with respect to the medial-lateral and anterior-posterior directions. As will become appreciated from the description below, the expandable intervertebral implant 20 can be inserted into the disc space 22 in an anterior direction, a posterior direction, or any alternative direction between 0° and 180° with respect to the anterior and posterior sides.

Figure 1B:
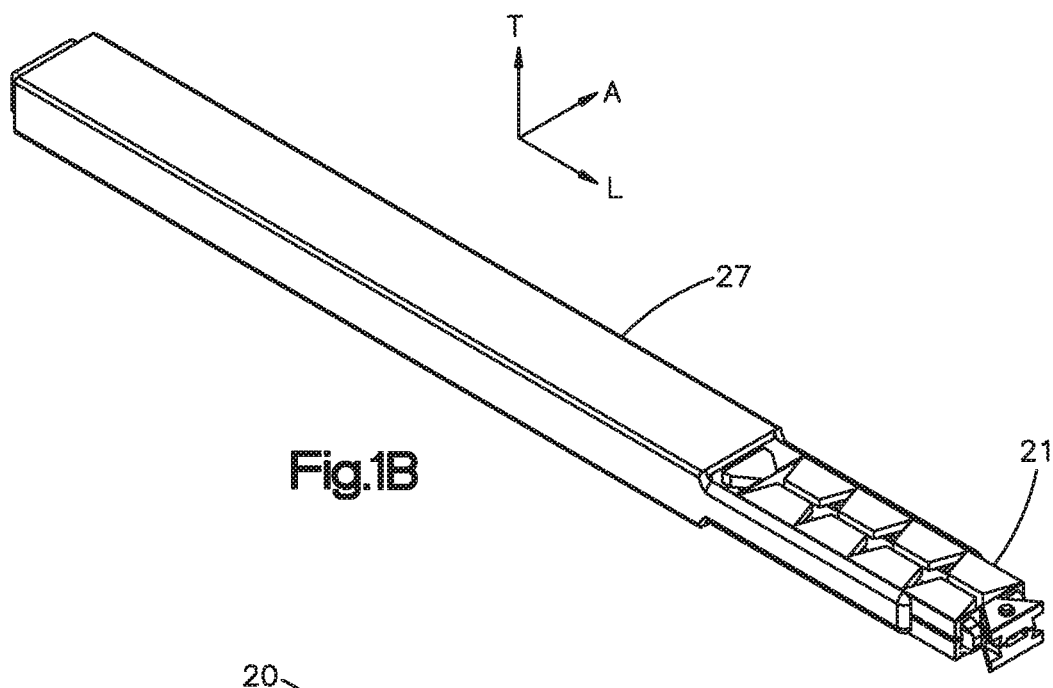
FIG. 1B is a perspective view of an intervertebral implant system showing an expandable intervertebral fusion cage of FIG. 1A in an initial position whereby the fusion cage is in an unexpanded lateral position and an unexpanded transverse position.
Figure 1C:
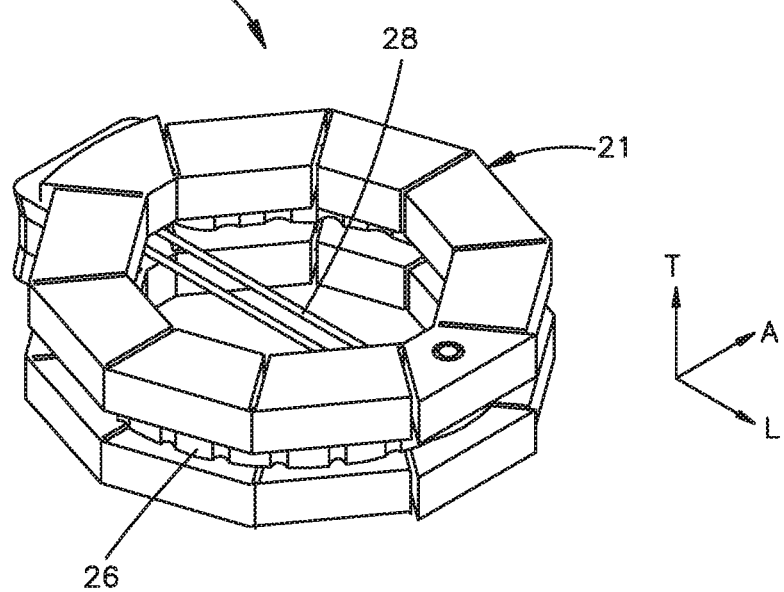
FIG. 1C is a perspective view of the intervertebral fusion cage illustrated in FIG. 1A, shown in the expanded lateral position and the expanded transverse position.

Referring also to FIGS. 1A-1C, the expandable intervertebral fusion cage 20 can be expandable both the lateral direction A from a first lateral position shown in FIG. 1B to an expanded lateral position shown in FIG. 1C. In the first lateral position, the fusion cage 20 defines a first width along the lateral direction A. In the expanded lateral position, the fusion cage 20 defines an expanded width along the lateral direction A that is greater than the first maximum width. In one example, the first lateral position can be an unexpanded lateral position, whereby the fusion cage 20 is unable to be actuated so as to collapse to a width less than the first width.

Further, the expandable fusion cage 20 is expandable along the transverse direction T from a first transverse position shown in FIG. 1B to an expanded transverse position shown in FIG. 1C. In the first transverse position, the fusion cage 20 defines a first height along the transverse direction T. In the expanded transverse position, the fusion cage 20 defines an expanded height along the transverse direction T that is greater than the first height. In one example, the first transverse position can be an unexpanded transverse position, whereby the fusion cage 20 is unable to be actuated so as to collapse to a height less than the first height.

As will become appreciated from the description below, the fusion cage 20 is expandable along the lateral direction A independent of expansion along the transverse direction T. Thus, the fusion cage 20 is configured to be expanded along the lateral direction A without being expanded or contracted along the lateral direction T. A. Otherwise stated, expansion of the fusion cage 20 in the lateral direction A does not cause the fusion cage 20 to expand or contract along the transverse direction T. Similarly, the fusion cage 20 is expandable along the transverse direction T independent of expansion along the lateral direction A. Thus, the fusion cage 20 is configured to be expanded along the transverse direction T without being expanded or contracted along the lateral direction A. Otherwise stated, expansion of the fusion cage 20 in the transverse direction T does not cause the fusion cage 20 to expand or contract along the lateral direction A.

Figure 10A:
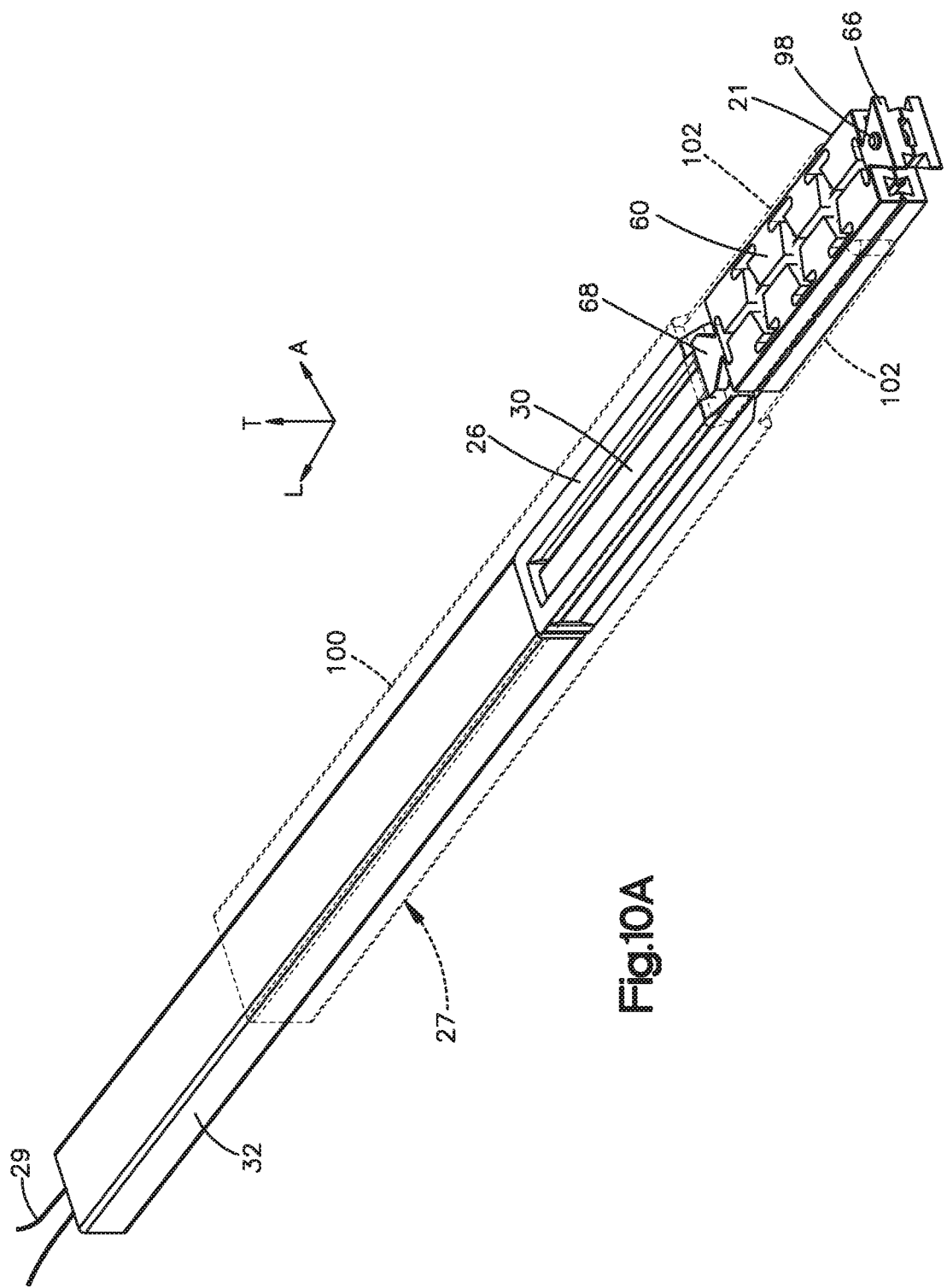
FIG. 10A is a perspective view of the intervertebral implant system illustrated in FIG. 2, showing the retainer as transparent for the purposes of illustration.
Figure 10B:
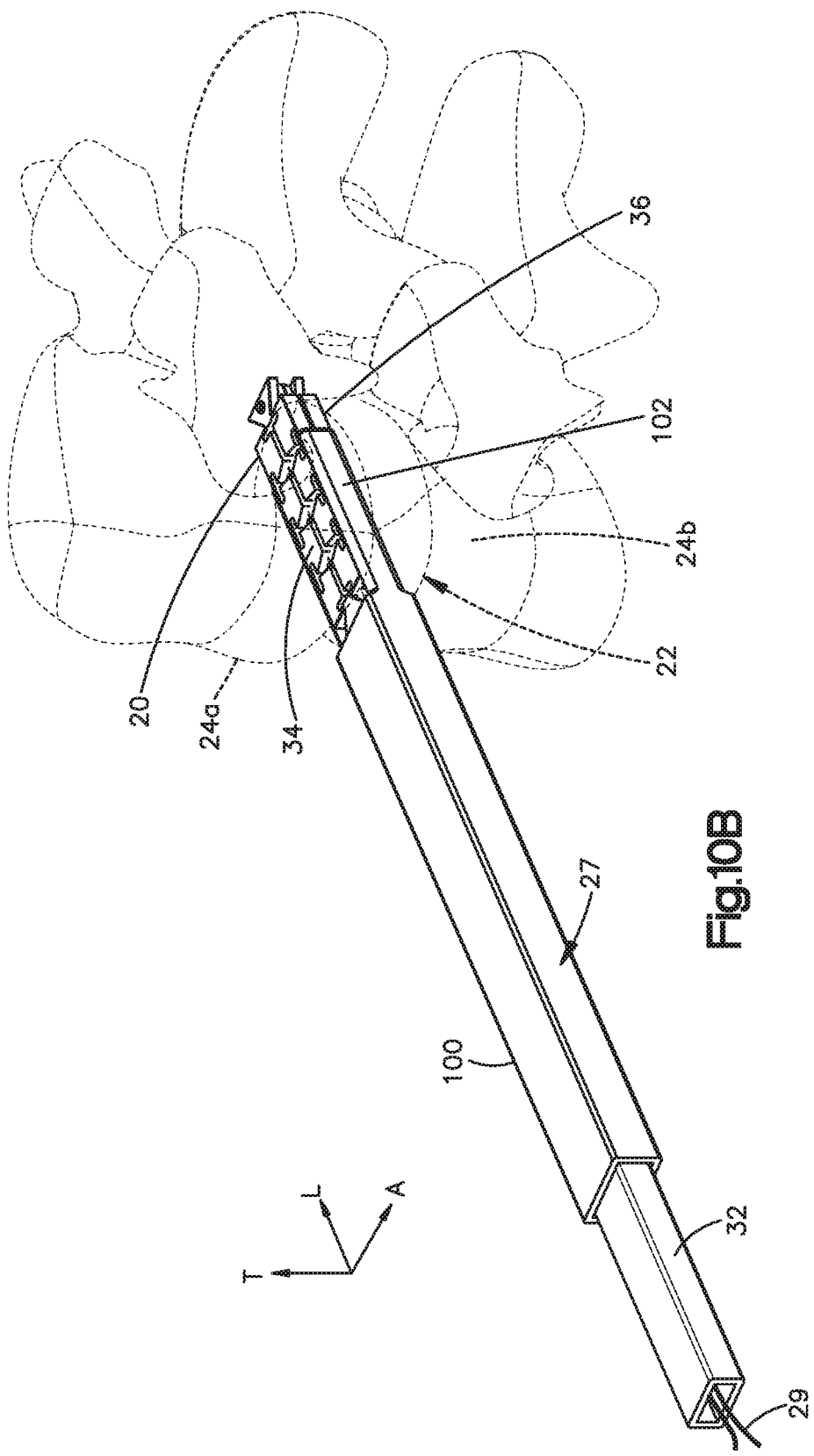
FIG. 10B is a perspective view of the intervertebral implant system illustrated in FIG. 10A, showing the fusion cage inserted into an intervertebral disc space while the fusion cage is in the unexpanded lateral position and the unexpanded transverse direction.

During use, the fusion cage 20 can be inserted into the intervertebral disc space 22 in the unexpanded lateral position and in the unexpanded transverse position as shown in FIG. 1B (see also FIG. 10B). The fusion cage 20 can then be expanded independently in each of the lateral direction A and the transverse direction T. Thus, the fusion cage can be easy to insert into the disc space, and subsequently expanded to a desired footprint along a plane that includes the lateral direction A and the longitudinal direction L, and a desired height.

Figure 2:
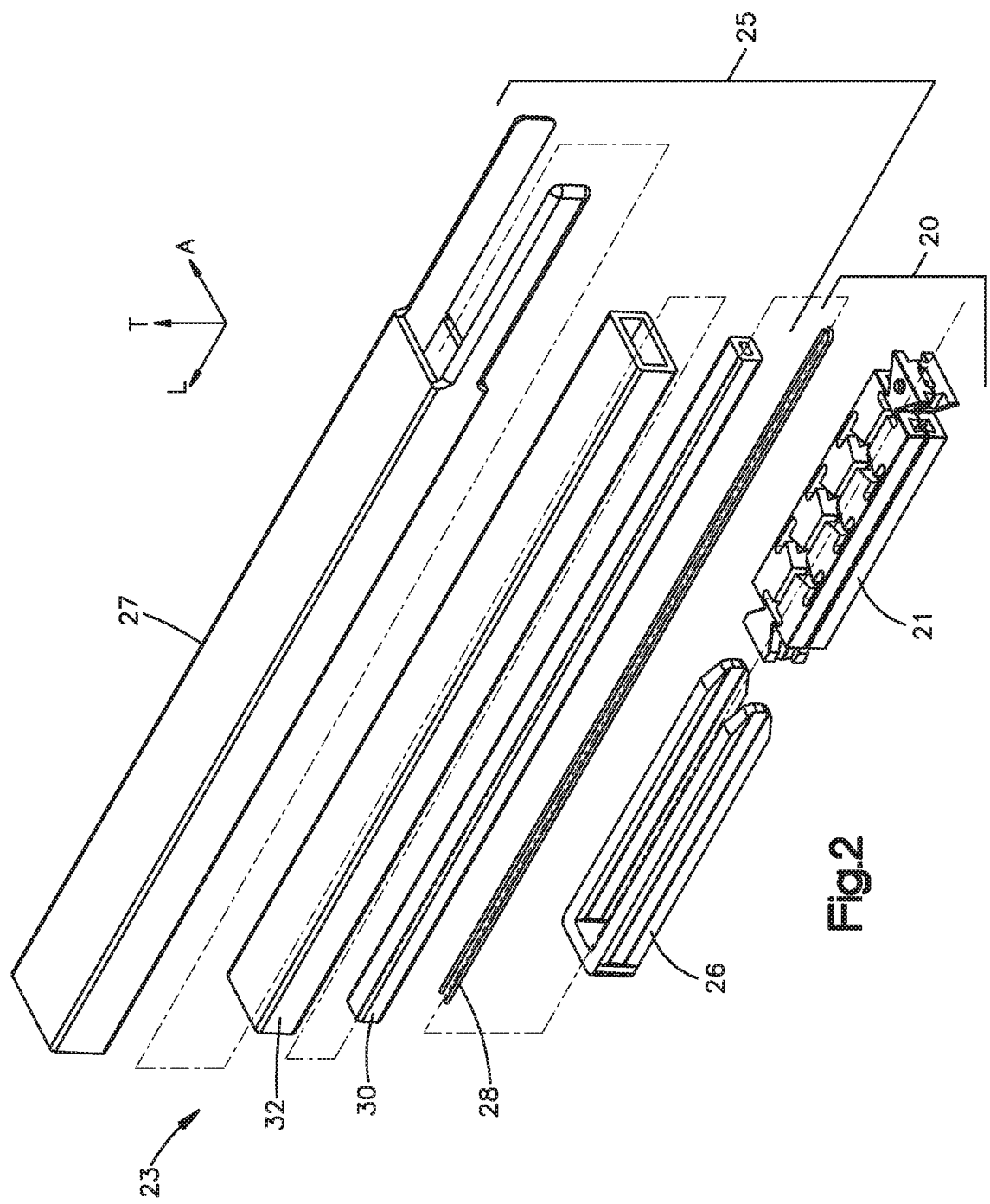
FIG. 2 is an exploded perspective view of the intervertebral implant system illustrated in FIG. 1A, including the intervertebral fusion cage, a handle, a core, a retainer, and an actuation member.
Figure 3A:
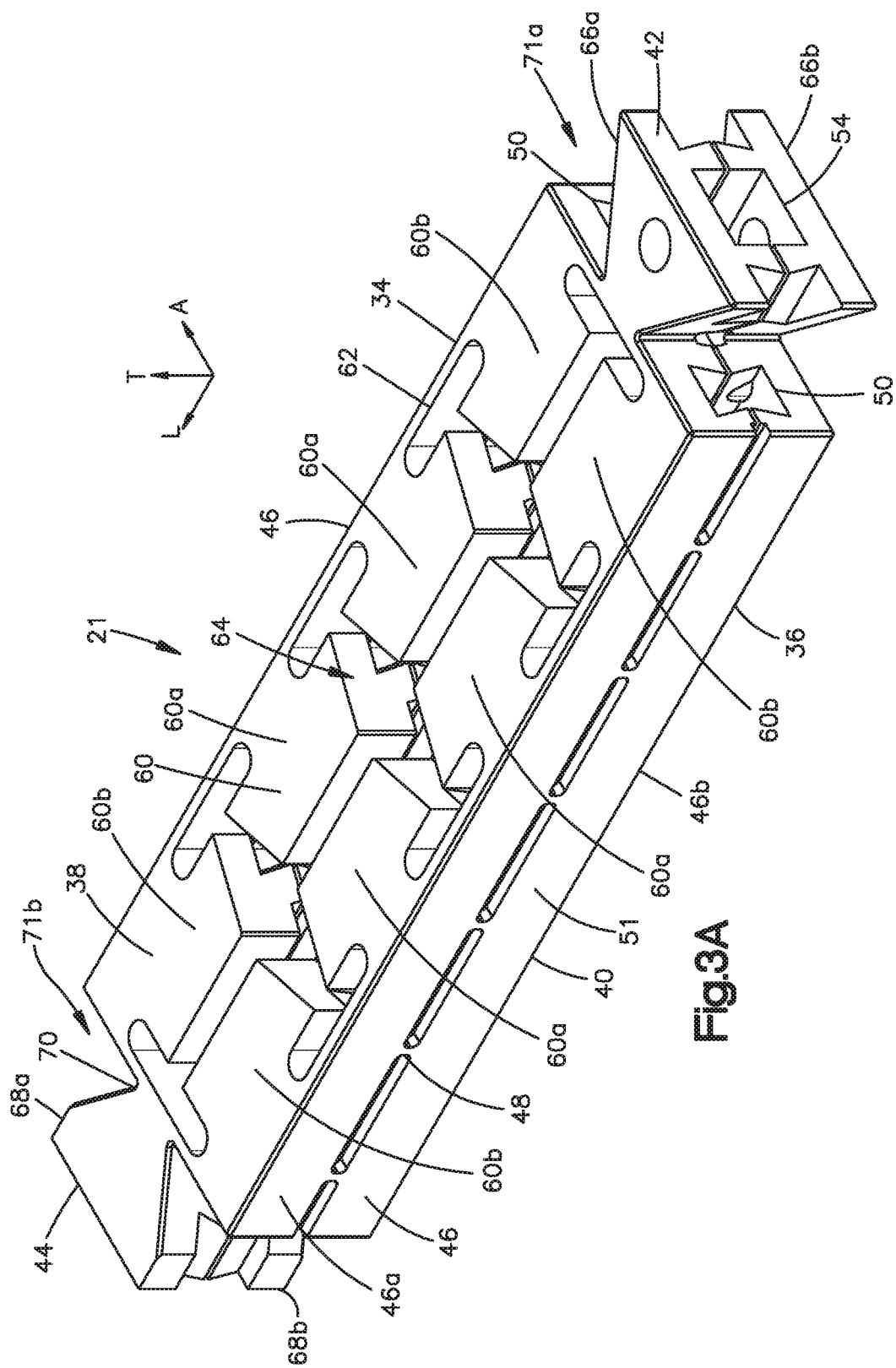
FIG. 3A is a perspective view of the fusion cage shown in the unexpanded lateral position and the unexpanded transverse position.

Referring now to FIG. 2, an intervertebral implant system 23 includes an intervertebral implant such as the intervertebral fusion cage 20, and an instrumentation assembly 25. The instrumentation assembly 25 can be configured to support the fusion cage 20 as the fusion cage 20 is inserted into the disc space 22. The instrumentation assembly 25 can also be configured to iterate the fusion cage 20 from the first lateral position to the expanded lateral position. The instrumentation assembly 25 can further be configured to iterate the fusion cage 20 from the first transverse position to the expanded transverse position.

For instance, the instrumentation assembly 25 can include a retainer 27 that is configured to be placed adjacent opposed outer surfaces of the fusion cage 20 as the fusion cage 20 is implanted into the disc space 22. The retainer 27 is configured to prevent the fusion cage 20 from expanding to the expanded lateral position while permitting the fusion cage 20 to expand to the expanded transverse position. The instrumentation assembly 25 can further include a core 26 that is configured to be inserted into the fusion cage so as to expand the cage from the unexpanded transverse position to the expanded transverse position. In this regard, the core 26 can also be referred to as a transverse expansion member. The instrumentation assembly 25 can further include an actuation member 28 that is configured to apply a force to the fusion cage 20 that causes the fusion cage 20 to expand from the unexpanded lateral position to the expanded lateral position. In this regard, the actuation member 28 can also be referred to as a lateral expansion member. The instrumentation assembly 25 can further include a handle 30 that is configured to be inserted into the fusion cage 20 when the fusion cage is in the unexpanded lateral position and the unexpanded transverse position. The handle 30 can be configured to receive and guide the actuation member 28. The instrumentation assembly 25 can further include a pusher member 32 that is configured to push the core 26 into the fusion cage 20 so as to expand the cage 20 to the expanded transverse position. The pusher member 32 can further provide a counter force to the cage 20 that offsets a force applied to the cage 20 by the actuation member 28 when the cage 20 is expanded to the expanded lateral position. In this regard, the pusher member 32 can be referred to as a brace member that braces the cage 20 as the actuation member expands the cage to the expanded lateral position.

It should be appreciated that the instrumentation assembly 25 can alternatively include a pusher member that is configured to push the core 26 into the fusion cage 20 so as to expand the cage 20 to the expanded transverse position, and a separate brace member that is configured to brace the cage 20 as the actuation member expands the cage to the expanded lateral position.

Referring now also to FIGS. 3A-3E, the expandable intervertebral fusion cage 20 includes a cage body 21 that includes a first or upper vertebral engagement body 34 and a second or lower vertebral engagement body 36. The upper vertebral engagement body 34 and the lower vertebral engagement body 36 are spaced from each other along the transverse direction T. The upper and lower vertebral engagement bodies 34 and 36 are configured to engage the superior and inferior vertebral bodies 24a and 24b, respectively. For instance, the upper and lower vertebral engagement bodies 34 and 36 are configured to contact the superior and inferior vertebral bodies 24a and 24b, respectively. In particular, the upper vertebral engagement body 34 defines an upper vertebral engagement surface 38 that is configured to contact the superior vertebral body 24*a*. Similarly, the lower vertebral engagement body 36 defines a lower vertebral engagement surface 40 that is configured to contact the inferior vertebral body 24*b*. In this regard, the upper and lower vertebral engagement surfaces 38 and 40 can be referred to as vertebral contacting surfaces. Similarly, the upper and lower vertebral engagement bodies 34 and 36 can be referred to as vertebral contacting bodies.

The upper and lower vertebral engagement surfaces 38 and 40 can be smooth so as to reduce potential causes of friction during insertion of the fusion cage 20 into the disc space 22. Alternatively, each of the upper and lower surfaces 38 and 40 can comprise features to promote and secure initial fixation to the vertebral bodies 24*a* and 24*b* and bony ingrowth including, but not limited to, spikes, keels, teeth, projections (such as dovetails), and recesses (such as grooves), thereby allowing the cage 20 to resist migration in the intervertebral space 22.

As described above, the fusion cage 20 can be vertically expandable along the transverse direction T from the first transverse position that defines the first height to the expanded transverse position that defines the expanded height. The first height can be defined from a first location on the upper vertebral engagement surface 38 to a second location on the lower vertebral engagement surface 40 along the transverse direction T. The second height can also be defined from the first location on the upper vertebral engagement surface 38 to the second location on the lower vertebral engagement surface 40 along the transverse direction T. Thus, the first height and the expanded height can be measured from the same respective locations of the upper vertebral engagement surface 38 and the lower vertebral engagement surface 40.

The cage body 21 further defines a leading end 42 and a trailing end 44 that are opposite each other along the longitudinal direction L. The leading end 42 is spaced from the trailing end 44 in a forward direction or insertion direction that defines the direction of insertion of the fusion cage 20 into the disc space 22. Thus, the insertion direction can be oriented along the longitudinal direction L. The terms "front," "forward" and derivatives thereof as used herein can refer to the forward direction unless otherwise indicated. Similarly, the trailing end 44 is spaced from the leading end 42 in a rearward direction that is opposite the forward direction. The terms "rear," "rearward" and derivatives thereof as used herein can refer to the rearward direction unless otherwise indicated. The cage body 21 further includes first and second side walls 46 that extend between the leading end 42 and the trailing end 44. The first and second side walls 46 are opposite each other along the lateral direction A. The first and second side walls 46, the leading end 42, and the trailing end 44 can all be monolithic with each other when the cage 20 is in the first transverse position.

The first and second side walls 46 can each extend from the leading end 42 to the trailing end 44. In one example, the upper vertebral engagement body 34 can define a first or upper portion 46*a* of each of the side walls 46, and a second or lower portion 46*b* of each of the side walls 46. The upper portions 46*a* can be aligned with the lower portions 46*b* of each of the respective side walls 46 along the transverse direction T. When the intervertebral fusion cage 20 is in the first lateral position, the first and second side walls 46 can be oriented substantially parallel to each other. In particular, the first and second side walls 46 can be longer along the longitudinal direction L than they are wide along the lateral direction A and thick along the transverse direction T.

With continuing reference to FIGS. 3A-3E, the cage body 21 can further include at least one rib 48 that joins the upper vertebral engagement body 34 to the lower vertebral engagement body 36 when the cage 20 is in the first transverse position. For instance, the at least one rib 48 can extend from the upper vertebral engagement body 34 to the lower vertebral engagement body 36 when the cage 20 is in the first transverse position. The cage body 21 can define respective gaps 53 that extend through the side walls 46 along the lateral direction between adjacent ones of the ribs 48. The ribs 48 can extend along a length from the upper vertebral engagement body 34 to the lower vertebral engagement body 36. The length can be less than the difference between the 1) the difference between the second height and the first height, and 2) a distance along which the upper vertebral engagement body 34 and the lower vertebral engagement body 36 are spaced from each other along the transverse direction T when the cage 20 is in the first transverse direction T. The at least one rib 48 can further be frangible, and configured to rupture as the cage 20 expands to the expanded transverse direction. Thus, the at least one rib 48 is configured to not join the upper vertebral engagement body 34 to the lower vertebral engagement body 36 when the cage 20 is in the expanded transverse position.

Alternatively, the at least one rib 48 can be flexible, and configured to stretch as the cage 20 expands to the expanded transverse position. Thus, the at least one rib 48 can be configured to join the upper vertebral engagement body 34 to the lower vertebral engagement body 36 when the cage 20 is in the expanded transverse position.

Alternatively still, the length of the at least one rib 48 can be at least equal to or greater than the difference between the 1) the difference between the second height and the first height, and 2) a distance along which the upper vertebral engagement body 34 and the lower vertebral engagement body 36 are spaced from each other along the transverse direction T when the cage 20 is in the first transverse direction T. As a result, the at least one rib 48 can also join the upper vertebral engagement body 34 to the lower vertebral engagement body 36 when the cage 20 is in the expanded transverse position In one example, each of the side walls 46 can include at least one rib 48 that joins the respective upper portion 46*a* to the respective lower portion 46*b*. For instance, the at least one rib 48 can be configured as a plurality of ribs 48. The ribs 48 of each of the side walls 46 can be spaced from each other along the longitudinal direction L. The side walls 46 can include any number of ribs 48 as desired, depending on the desired force that the ribs 48 can cumulatively absorb prior to rupturing.

With continuing reference to FIGS. 3A-3E, the cage 20 can include at least one core-receiving channel 50 that extends at least into the cage body 21. The at least one core channel is configured to receive the core 26 (see FIG. 2) when the core 26 is inserted into the cage body 21. The at least one core-receiving channel 50 can be open at the rear end of the cage body 21. The core-receiving channel 50 can extend in the forward direction from the rear end of the cage body 21 toward the front end of the cage body 21. In one example, the at least one core-receiving channel 50 can extend entirely through the cage body 21 from the rear end to the front end. Each of the upper vertebral engagement body 34 and the lower vertebral engagement body 36 can define respective inner surfaces 52 that face each other along the transverse direction T. For instance, the inner surfaces 52 can be opposite the respective upper and lower vertebral engagement surfaces 38 and 40. The inner surfaces 52 can be defined by the links 60. The inner surfaces 52 can define respective recesses 56 that cooperate with each other so as to define the at least one core-receiving channel 50. The recesses 56 of each at least one channel 50 can be aligned with each other along the transverse direction T.

As will be appreciated from the description below, the distance between the inner surfaces 52 in the respective channels 50 along the transverse direction can be less than the height of the core 26 along the transverse direction T. The core-receiving channels 50 can extend at least into or through the respective side walls 46. For instance, the core-receiving channels 50 can be defined entirely by the upper portions 46a and the lower portions 46b of the side walls 46. Thus, the recesses 56 can extend into the inner surfaces 52 of the upper portion 46a and the lower portion 46b of each of the side walls 46.

In one example, the at least one core-receiving channel 50 can include a pair of core-receiving channels 50 that are spaced from each other along the lateral direction A. In particular, the cage body 21 can define a midplane that extends centrally from the leading end 42 to the trailing end 44 along the longitudinal direction L. The midplane can be defined by the longitudinal direction L and the transverse direction T, and can be equidistantly spaced from each of the side walls 46. The midplane can be disposed between the core-receiving channels 50. In particular, the core-receiving channels 50 can be equidistantly spaced from the midplane. Further, the core-receiving channels 50 can be substantially identical or identical with each other. Further, the core-receiving channels 50 can be oriented substantially parallel to each other. In one example, the core-receiving channels 50 can be elongate along the longitudinal direction L.

As illustrated in FIG. 3C, each of the side walls 46 can define at least one cage interlocking member that at least partially defines the respective channel 50. For instance, the upper vertebral engagement body 34 can include upper cage interlocking members 47a that at least partially define the respective recess 56, and thus partially define the corresponding channels 50. The upper cage interlocking members 47a can be opposite each other along the lateral direction A. Similarly, the lower vertebral engagement body 36 can include lower cage interlocking members 47b that at least partially define the respective recess 56, and thus partially define the corresponding channels 50. The lower cage interlocking members 47b can be opposite each other along the lateral direction A. As will be appreciated from the description below, the cage interlocking members are configured to engage complementary core interlocking member of the core 26 (see FIG. 2) so as to couple the upper and lower vertebral engagement bodies 34 and 36 to the core 26 with respect to movement away from each other along the transverse direction T. Thus, the core 26 can couple to each of the upper and lower vertebral engagement bodies 34 and 36 so as to prevent the upper and lower vertebral engagement bodies 34 and 36 from separating away from each other when the cage 20 is in the expanded transverse position.

In one example, the recesses 56, and thus the channels 50, can be defined by opposed upper internal side surfaces 49a and opposed lower internal side surfaces 49b of the upper and lower vertebral engagement bodies 34 and 36, respectively. In particular, the opposed upper internal side surfaces 49a of each of the channels 50 can be defined by the upper portions 46a of the respective side walls 46. The opposed lower internal side surfaces 49b of each of the channels 50 can be defined by the lower portions 46b of the respective side walls 46. It should be appreciated that the links 60 can define the side surfaces 49a and 49b.

The upper side surfaces 49a can taper laterally inwardly toward the midplane of the cage body 21 as they extend toward the lower vertebral engagement body 36, and in particular toward the lower portion 46b of the side wall 46. Similarly, the lower side surfaces 49b can taper laterally inwardly toward the midplane of the cage body 21 as they extend toward the upper vertebral engagement body 34, and in particular toward the lower portion 46a of the side wall 46. The upper side surfaces 49a can define the upper cage interlocking members 47a, and the lower side surfaces 49b can define the upper cage interlocking members 47b.

In particular, when the core 26 is inserted into the cage body 21, at least a portion of the upper side surfaces 49a can be aligned with, and interfere with, respective ones of the core interlocking members along the transverse direction T so as to prevent the upper vertebral engagement body 34 from being removed from the core 26 along the transverse direction T. Further, the upper side surfaces 49a can abut respective ones of the core interlocking members so as to prevent the upper vertebral engagement body 34 from moving away from the lower vertebral engagement body 36 along the transverse direction T. Similarly, when the core 26 is inserted into the cage body 21, at least a portion of the lower side surfaces 49b can be aligned with, and interfere with, respective ones of the core interlocking members along the transverse direction T so as to prevent the lower vertebral engagement body 36 from being removed from the core 26 along the transverse direction T. Further, the lower side surfaces 49b can abut respective ones of the core interlocking members so as to prevent the lower vertebral engagement body 36 from moving away from the upper vertebral engagement body 34 along the transverse direction T. Thus, it can be said that the core 26 is configured to couple the upper vertebral engagement body 34 to the lower vertebral engagement body 36 when the cage 20 is in the expanded transverse position.

Referring again to FIGS. 3A-3E, the cage 20 can further include at least one handle-receiving channel 54 that extends at least into the cage body 21. The at least one handle-receiving channel 54 is configured to receive the handle 30 so as to couple the cage 20 to the handle 30 when the handle 30 is inserted into the handle-receiving channel 54. The handle-receiving channel 54 can be sized such that the handle 30 is loosely received therein. Alternatively, the handle-receiving channel 54 can be sized such that the handle 30 is press-fit therein. The at least one handle receiving channel 54 can be aligned with the midplane of the cage body 21.

The at least one handle-receiving channel 54 can be open at the rear end of the cage body 21. The handle-receiving channel 54 can extend in the forward direction from the rear end of the cage body 21 toward the front end of the cage body 21. In one example, the handle-receiving channel 54 can extend through the front end of the cage body 21 as desired. Alternatively, the handle-receiving channel 54 can terminate at a location between the front end of the cage body 21 and the rear end of the cage body 21. In particular, the at least one handle-receiving channel 54 can extend through the trailing end 44 of the cage body 21. The at least one handle-receiving channel 54 can extend from the trailing end 44 at least toward the leading end 42 along the transverse direction T. In one example, the handle-receiving channel 54 can extend through the leading end 42 of the cage body 21 as desired. Alternatively, the handle-receiving channel 54 can terminate at a location between the leading end 42 and the trailing end 44 of the cage body 21. In one example, the inner surfaces 52 of the upper vertebral engagement body 34 and the lower vertebral engagement body 36 can define respective recesses 58 that cooperate with each other so as to define the at least one core-receiving channel 50. While FIG. 3D illustrates the inner surface 52 of lower vertebral engagement body 36, it is appreciated that the upper vertebral engagement body 34 can be substantially identical or identical to the lower vertebral engagement body 36. Thus, structure described herein and illustrated in FIG. 3D with respect to the lower vertebral engagement body 36 can apply with equal effect to the upper vertebral engagement body 34.

With continuing reference to FIGS. 3A-3E, the side walls 46 can include respective pluralities of interconnected links 60. In particular, the links 60 of each of the side walls 46 can be interconnected to each other along the longitudinal direction L when the cage 20 is in the first lateral position. For instance, each of the upper portions 46a of the side walls 46 can include a respective plurality of interconnected links 60. Further, each of the lower portions 46b of the side walls 46 can include a respective plurality of interconnected links 60. Adjacent ones of the interconnected links 60 can be pivotally coupled to each other to allow for the side walls 46 to move away from each other as the cage 20 moves from the first lateral position to the expanded lateral position. In particular, the links 60 are configured to pivot relative to each other so as to allow the side walls 46 to move away from each other along the lateral direction A.

In particular, the side walls 46 can include joints 62 that pivotally attach adjacent ones of the links 60 to each other. The joints 62 can define hinges. In particular, the joints 62 can be monolithic with the links 60, and thus can define living hinges. Thus, the links 60 can all be monolithic with each other. Alternatively, the joints 62 can be defined by separate structures that are discretely attached to one or both of the adjacent links 60 that are joined by the joints 62 so as to allow the adjacent links 60 to pivot relative to each other. The links 60 can be grouped into respective arrays 61 of links 60 that are connected to each other substantially along the longitudinal direction L when the cage 20 is in the first position. In particular, each of the arrays 61 can be defined by respective different ones of the upper and lower portions 46a and 46b of the first and second side walls 46. The links 60 can extend from the joints 62 toward the midplane of the cage body 21.

Each of the links 60 can be wedge shaped along a plane that is defined by the lateral direction A and the longitudinal direction L. In particular, the links 60 can be inwardly tapered along the plane as they extend from the respective joints 62 toward the midplane. Further, the links 60 of each side wall 46 can be inwardly tapered along the plane as they extend from the respective joints 62 toward the opposed side wall 46. Thus, each array 61 of links 60 can define respective gaps 64 disposed between adjacent ones of the links 60 along the longitudinal direction L. The gaps 64 can taper outwardly along the plane as they extend toward the midplane. Further, the gaps 64 of each side wall 46 can be outwardly tapered along the plane as they extend from the toward the opposed side wall 46. Thus, the gaps 64 of each side wall 46 are open in a direction toward the opposed side wall 46, and closed in a direction away from the opposed side wall 46.

Each array 61 of links 60 can include at least one intermediate link 60a and first and second longitudinally outermost links 60b. For instance, each array 61 of links 60 can include a plurality of intermediate links 60a, including at least a pair of intermediate links 60a. The intermediate links 60a of each array 61 can be substantially identical to each other in size and shape. Further, the intermediate links 60a of each of the side walls 46 can be substantially identical to each other, though they can be oriented opposite each other. Moreover, the intermediate links 60a of the first side wall 46 can be substantially mirror images of the intermediate links 60a of the second side wall 46 with respect to the midplane. Additionally, the intermediate links 60a of the upper portions 46a can be substantially aligned with each other along the lateral direction A, and the intermediate links 60a of the lower portions 46b can be substantially aligned with each other along the lateral direction A. Each of the intermediate links 60a can be symmetrical about a respective intermediate link midplane that bisects the link 60a and is defined by the transverse direction T and the lateral direction A.

Likewise, the outermost links 60b of each of the arrays 61 can be substantially mirror images of each other with respect to a plane that includes the lateral direction A and the transverse direction T. Further, the outermost links 60 of the upper portions 46a can be substantially identical with the outermost links 60 of the lower portion 46a of the same side wall 46 that are in alignment along the transverse direction. Moreover, the outermost links 60b of the first side wall 46 can be substantially mirror images of the aligned outermost links 60b of the second side wall 46 with respect to the midplane said alignment being along the lateral direction A. Additionally, the outermost links 60b of the upper portions 46a of each side wall 46 can be substantially identical with aligned outermost links 60 of the lower portions 46a of the respective side wall 46, said alignment being along the transverse direction T.

The gaps 64 defined by adjacent ones of the links 60 of each array can be substantially identical to each other in size and shape when the cage 20 is in the first lateral position. Further, the gaps 64 of the upper portion 46a of each of the side walls 46 can be substantially identical to align ones of the gaps 64 of the respective lower portion 46b, the alignment being along the transverse direction T. Additionally, the gaps 64 of each of the side walls 46 can be substantially mirror images of aligned ones of the gaps 64 of the opposed side wall 46, the alignment being along the lateral direction A.

The substantially identical links 60 described above can be substantially identical with each other when the cage 20 is in the first lateral position, between the first position and the expanded lateral position, and the expanded lateral position. The links 60 that define substantially mirror images of each other can define substantially mirror images of each other when the cage 20 is in the first lateral position, between the first position and the expanded lateral position, and the expanded lateral position. Likewise, the substantially identical gaps 64 described above can be substantially identical with each other when the cage 20 is in the first lateral position, between the first position and the expanded lateral position, and the expanded lateral position. The gaps 64 that define substantially mirror images of each other can define substantially mirror images of each other when the cage 20 is in the first lateral position, between the first position and the expanded lateral position, and the expanded lateral position.

The cage body 21 can further include at least one leading link 66 and at least one trailing link 68. The at least one leading link 66 can define the leading end of the fusion cage 20. Similarly, the at least one trailing link 68 can define the trailing end of the fusion cage 20. In one example, the cage body 21 can include an upper leading link 66a and a lower leading link 66b. Similarly, the cage body 21 can include an upper trailing link 68a and a lower trailing link 68b. For instance, the upper vertebral engagement body 34 can include the upper leading link 66a and the upper trailing link 68a. The lower vertebral engagement body 36 can include the lower leading link 66b and the lower trailing link 68b.

The leading links 66a and 66b and the trailing links 68a and 68b can be substantially identical to each other. The leading links 66a and 66b and the trailing links 68a and 68b can be oriented such that the leading links 66a and 66b are mirror images of the respective trailing links 68a and 68b. Each of the links 66 and 68 can each be wedge-shaped. For instance, each of the leading links 66 can taper inwardly along a plane as they extend toward the trailing end, the plane being defined by the lateral direction A and the longitudinal direction L Each of the trailing links 68 can taper inwardly along a plane as they extend toward the leading end, the plane being defined by the lateral direction A and the longitudinal direction L Further, each of the links 66 and 68 can be symmetrical about a respective link midplane that bisects the respective links 66 and 68 and is defined by the transverse direction T and the longitudinal direction L.

The cage body 21 can include joints 70 that pivotally attach each of the links 66 and 68 to respective ones of the outermost links 60b. For instance, each of the links 66 and 68 can be attached to a respective one of the outermost links of each of the side walls 46. The joints 70 can define hinges. In particular, the joints 70 can be monolithic with the outermost links 60b and the links 66 and 68, and thus can define living hinges. Thus, the links 60, 66, and 68 can all be monolithic with each other. Alternatively, the joints 70 can be defined by separate structures that are discretely attached to one or both of the respective one of the links 66 and 68 and the respective one of the outermost links 60b. The cage body 21 can define outermost gaps 71 that are defined between each of the links 66 and 68 and the respective adjacent outermost links 60b to which the links 66 and 68 are pivotally attached. For instance, the outermost links 60b of the first side wall 46 define respective first outermost gaps 71a with respect to the leading end links 66 and the trailing end links 68, respectively, and the outermost links 60b of the second side wall 46 define respective second outermost gaps 71b with respect to the leading end links 66 and the trailing end links 68. The first outermost gaps 71a and the second outermost gaps 71b can be substantially identical to each other in size and shape.

The links 66 and 68 can extend outward from the respective joints 70. Thus, the leading end links 66 can extend from the respective joints 70 along a direction away from the trailing end of the cage body 21. Similarly, the trailing end links 68 can extend from the respective joints 70 along a direction away from the leading end of the cage body 21. The links 66 and 68 can be aligned with the central midplane of the cage body 21.

It should be appreciated that while the cage body 21 has been described as one example, the cage body 21 can alternatively be constructed in accordance with any suitable embodiment as desired. For instance, the links 60 of each of each of the side walls 46 can be oriented so as to extend from the respective joints 62 in a direction away from the opposed side wall 46. Further, while the side walls 46 can define respective outer surfaces 51 that are substantially planar when the cage body 21 is in the first lateral position, the outer surfaces 51 of the side walls 46 can be configured having any suitable shape as desired. In this regard, it should be appreciated that each of the outer surfaces 51 can be define by an aggregation of respective outer surfaces of each of the links 60.

For instance, referring to FIGS. 4A-4B, the outer surfaces 51 of the side walls 46 can be scalloped. In particular, the outer surfaces of each of the respective links 60 can be curved. In one example, outer surfaces of each of the respective links 60 can be convex. The convex outer surfaces can be arc-shaped along a plane that is defined by the longitudinal direction L and the lateral direction A. Alternatively, the outer surfaces of the links 60 can be concave alone the plane. Further, as illustrated in FIGS. 4A-4B and as described above, each of the side walls 46 can include a plurality of ribs 38 that join the upper portion 46a to the respective lower portion 46b. The ribs 48 can be defined at respective intersection of adjacent links 60. The ribs 48 of each of the side walls 46 can be substantially identical to each other as illustrated in FIGS. 3A-3E and 4A-4B.

Figure 10C:
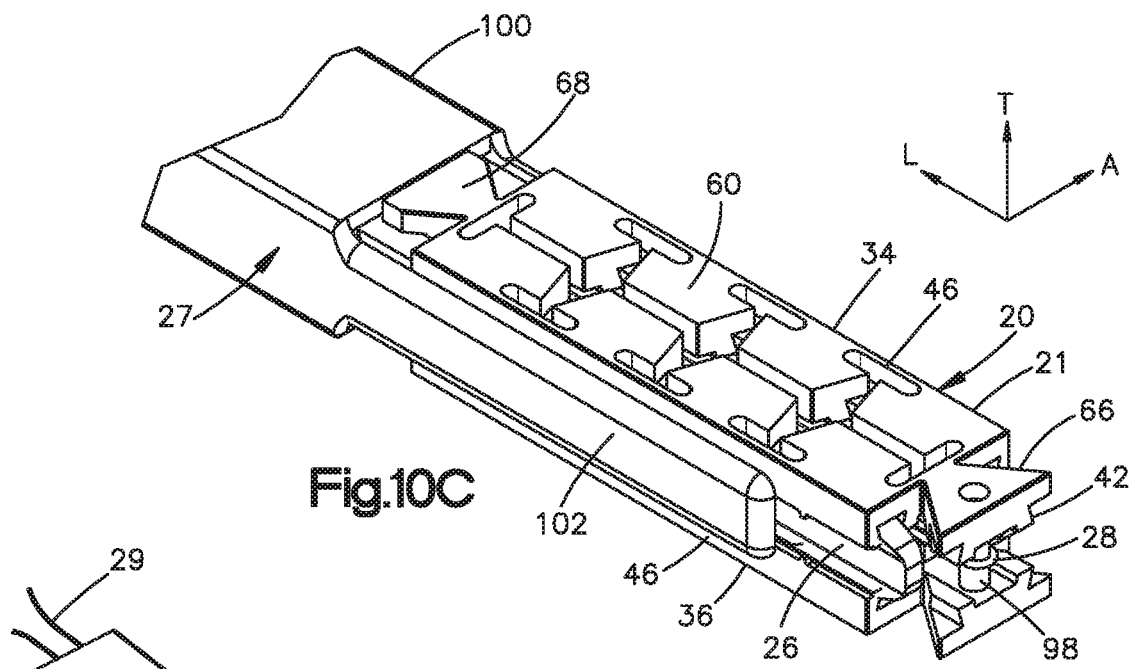
FIG. 10C is a perspective view of the intervertebral implant system illustrated in FIG. 10A, showing the core inserted into the fusion cage, thereby expanding the fusion cage to the expanded transverse position.
Figure 10D:
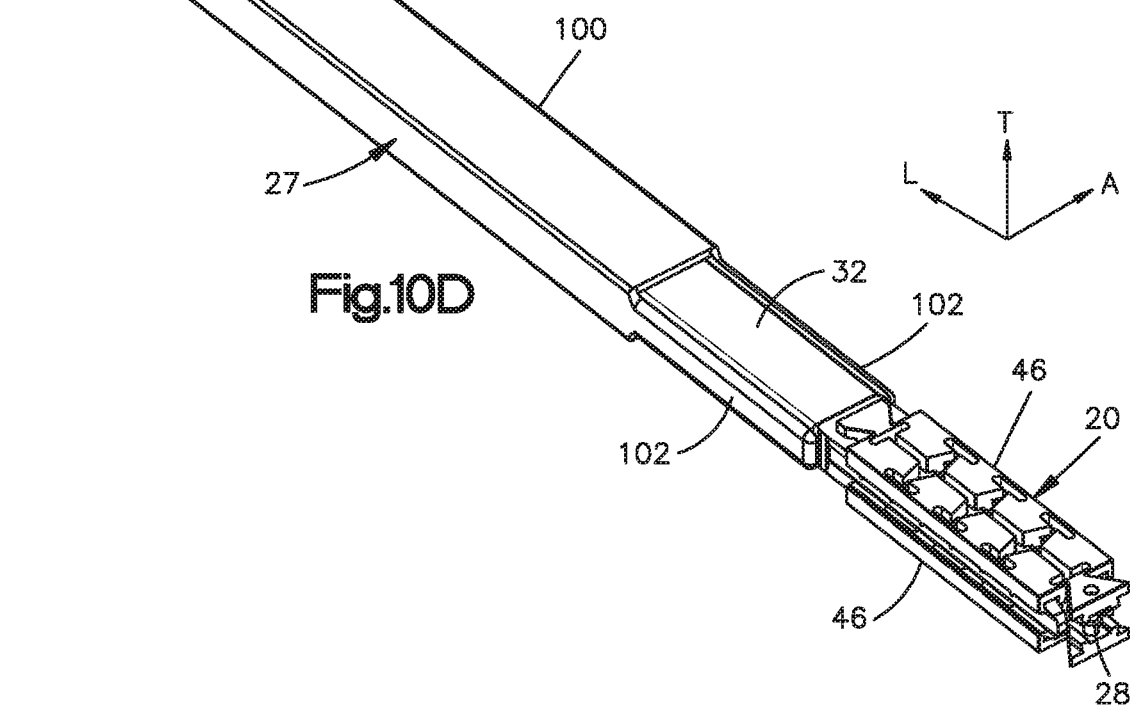
FIG. 10D is a perspective view of the intervertebral implant system illustrated in FIG. 10C, showing the retainer removed and the pusher member disposed against the fusion cage.

As will be appreciated from the description below, the cage 20 is responsive to a compressive force that causes the fusion cage 20 to expand from the first lateral position to the expanded lateral position. For instance, the compressive force can be applied to the leading and trailing ends of the cage body 21. In one example, the compressive force can be applied to the leading and trailing ends of the cage body 21. For instance, the compressive force can be applied to one or both of the leading end links 66 and to one or both of the trailing end links 68. The compressive force causes the side walls 46 to move away from each other. As shown at FIGS. 1C and 10G, as the side walls 46 move away from each other, the joints 62 and 70 allow for the angular articulation of the links 60 relative to both each other and the leading and trailing links 66 and 68, respectively. As the cage 20 expands along the lateral direction A to the expanded lateral position, the gaps 64 between adjacent ones of the links 60 of the side walls 46 (which can be referred to as intermediate gaps) decrease in size. Similarly, as the cage 20 expands along the lateral direction A to the expanded lateral position, the outermost gaps 71 decrease in size. In particular the interconnected adjacent ones of the links 60, 66, and 68 can abut each other when the cage 20 is in the expanded lateral position. Alternatively, the interconnected adjacent ones of the links 60, 66, and 68 can remain spaced from each other and can be oriented substantially parallel to each other when the cage 20 is in the expanded lateral position.

Figure 4C:
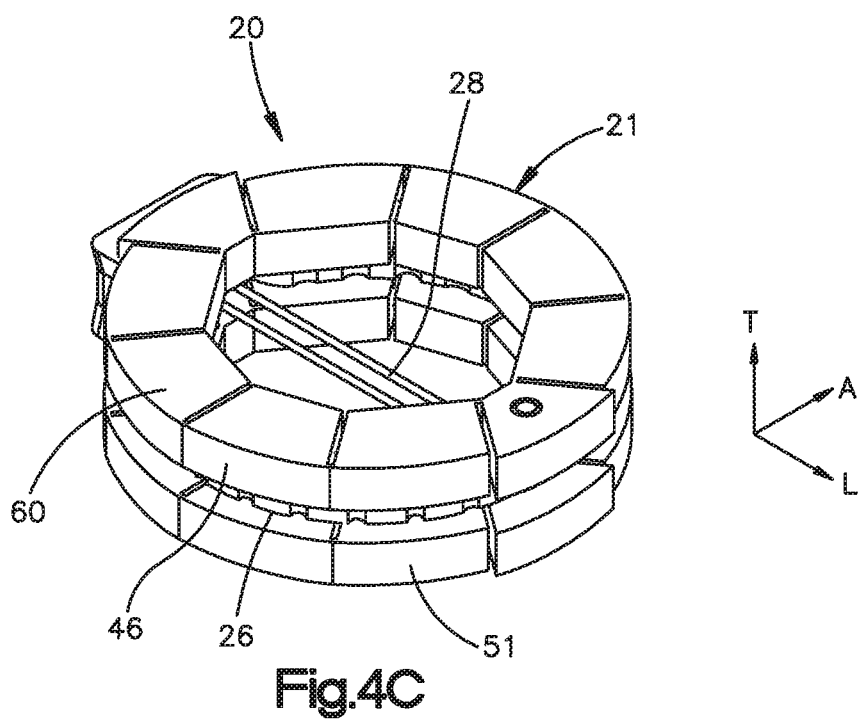
FIG. 4C is a perspective view of the fusion cage illustrated in FIG. 4A, shown in the expanded lateral position and the expanded transverse position.

As illustrated in FIG. 4C, when the cage 20, and thus the cage body 21, is in the expanded lateral position, the outer surfaces of the links 60 can, in combination, define a circular outer surface 51 of each of the side walls. For instance, the outer surfaces of at least a plurality of the links 60 up to all of the links 60 can be defined by respective radii that extend from a common center.

Referring now to FIGS. 5A-5D, the core 26 is configured to be inserted into the cage body 21 between the upper vertebral engagement body 34 and the lower vertebral engagement body 36. Because the core 26 can remain disposed in the fusion cage 20 after completion of the surgical procedure, the core 26 can be considered to be part of the fusion cage 20. The core 26 has a height along the transverse direction T that is sufficient such that insertion of the core 26 between the upper vertebral engagement body 34 and the lower vertebral engagement body 36 causes the intervertebral fusion cage 20 to expand along the transverse direction T to the expanded transverse position. In one example, the cage body 21 is inserted into the disc space 22, and the core 26 is then inserted into the cage body 21 so as to expand the cage body 21 along the transverse direction T.

The core 26 can include at least one core arm 72 that is configured to be inserted into the respective at least one core-receiving channel 50 so as to cause the cage body 21 to expand along the transverse direction T from the first transverse position to the expanded transverse position. The at least one core arm 72 can have a height along the transverse direction T that is greater than the height of the core-receiving channel 50 when the cage 20 is in the first transverse position. Accordingly, insertion of the at least one core arm 72 in the core-receiving channel 50 causes the cage body 21 to expand from the first transverse position to the expanded transverse position. The at least one core arm 72 can include a pair of core arms 72 that are spaced from each other along the lateral direction. The core 26 can further include a bridge 74 that extends between, and is coupled to, each of the core arms 72. The bridge 74 and the core arms 72 can be monolithic with each other, or separate from each other and attached to each other as desired. The core 26 can define a through hole 76 that extends through the bridge 74 along the longitudinal direction L and is sized to receive the handle 30 (FIG. 2) as described in more detail below. The through hole 76 can be equidistantly spaced from the arms 72. The bridge 74 can have a height greater than the height of the handle-receiving channel 54 when the core 26 is inserted into the cage body 21. Accordingly, the bridge 74 can contact the leading end of the cage body 21 when the core 26 is fully inserted into the cage body 21. The through hole 76 of the bridge 74 can be aligned with the handle-receiving channel 54 along the longitudinal direction L.

The arms 72 can each have a tapered leading end 78 with respect to insertion into the cage body 21. The tapered leading ends 78 can taper outwardly along the transverse T direction as they extend in the rearward direction; that is, in a direction toward the bridge 74. The tapered leading ends 78 can define upper and lower bearing surfaces 80 that ride along the respective inner surfaces 52 of the channels 50 as the arms 72 are inserted into the channels 50. The tapered bearing surfaces 80 can push the upper and lower vertebral engagement bodies 34 and 36 away from each other along the transverse direction T during insertion of the arms 72 into the channels 50. The bearing surfaces 80 can define a variable taper along their respective lengths. Alternatively, the bearing surfaces 80 can define a substantially constant taper along their respective lengths. Between the bridge 74 and the tapered leading ends 78, the opposed transverse outer surfaces 82 of the arms 72 can be substantially flat. In particular, the opposed transverse surfaces 82 can lie substantially in a plane defined by the longitudinal direction L and the lateral direction A. Thus, once the tapered leading ends 78 have caused the cage body 21 to expand to the expanded transverse position, contact between the transverse outer surfaces 82 and the inner surfaces 52 of the channels 50 maintains the cage body in the expanded transverse position.

The upper outer surfaces 82 of the arms 72 can be coplanar with each other. Similarly, the lower outer surfaces 82 of the arms 72 can be coplanar with each other. The upper and lower engagement bodies 34 and 36 of the cage body 21 (see FIG. 3A) can rest on the opposed outer surfaces 82. Thus, when the opposed outer surfaces 82 lie substantially in respective planes defined by the longitudinal direction L and the lateral direction A, the upper and lower engagement bodies 34 and 36 can likewise lie in respective plans defined by the longitudinal direction L and the lateral direction A.

The arms 72 can extend along respective ones of the core-receiving channels 50 when the cage 20 is in the first lateral position. Thus, the arms 72 can be oriented substantially parallel to each other. For instance, the arms 72 can be elongate substantially along the longitudinal direction L when disposed in the channels 50. Thus, when the cage body 21 is in the first lateral position, the core is in a respective first lateral position whereby the arms 72 are aligned with the first and second side walls 46, respectively, of the cage body 21 along the transverse direction T.

Figure 6:
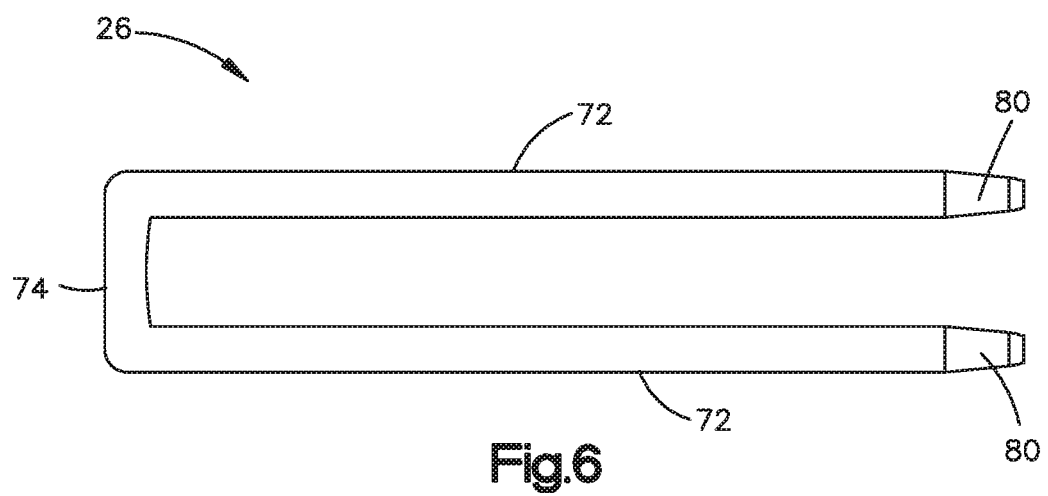
FIG. 6 is a top plan view of a core similar to FIG. 5A, but constructed in accordance with an alternative embodiment.

The arms 72 can be flexible with respect to bending along a plane that is defined by the lateral direction A and the longitudinal direction L. For instance, in one embodiment shown in FIGS. 5A and 5C, the arms 72 can define laterally opposed side surfaces 84 that extend between the opposed transverse outer surfaces 82. The side surfaces 84 of each of the arms 72 can define scallops 86 that are spaced from each other along the longitudinal direction L. As the cage body 21 moves from the first lateral position to the expanded lateral position, the side surfaces 49 urge the core 26 to likewise expand from a respective first lateral position to a respective expanded lateral position. In one example, the scallops 86 can define hinges that are configured to pivot and flex as the arms 72 move from the first lateral position to the expanded lateral position. The arms 72 remain in the channels 50 when the cage body 21 is in the expanded lateral position. Thus, the arms 72 can remain aligned with the side walls 46, respectively, when the cage body 21 is in the expanded lateral position. Alternatively, as illustrated at FIG. 6, the arms 72 can be devoid of scallops, but can be made of a suitably flexible material so as to allow the arms 72 to flex as they move from the first lateral position to the expanded lateral position. Thus, the side surfaces 84 can be substantially smooth as they extend in a plane defined by the longitudinal direction L and the lateral direction A.

As described above, when the core arms 72 are inserted into the respective core-receiving channels 50 can cause the at least one rib 48 of the cage body 21 (FIG. 3A) to rupture. As a result, the ruptured ribs 48 no longer attach the upper vertebral engagement body 34 to the lower vertebral engagement body 36. Accordingly, the core 26 is configured to couple to each of the upper vertebral engagement body 34 and the lower vertebral engagement body 36 with respect to separation of the upper and lower vertebral engagement bodies 34 and 36 away from each other along the transverse direction T.

Figure 10E:
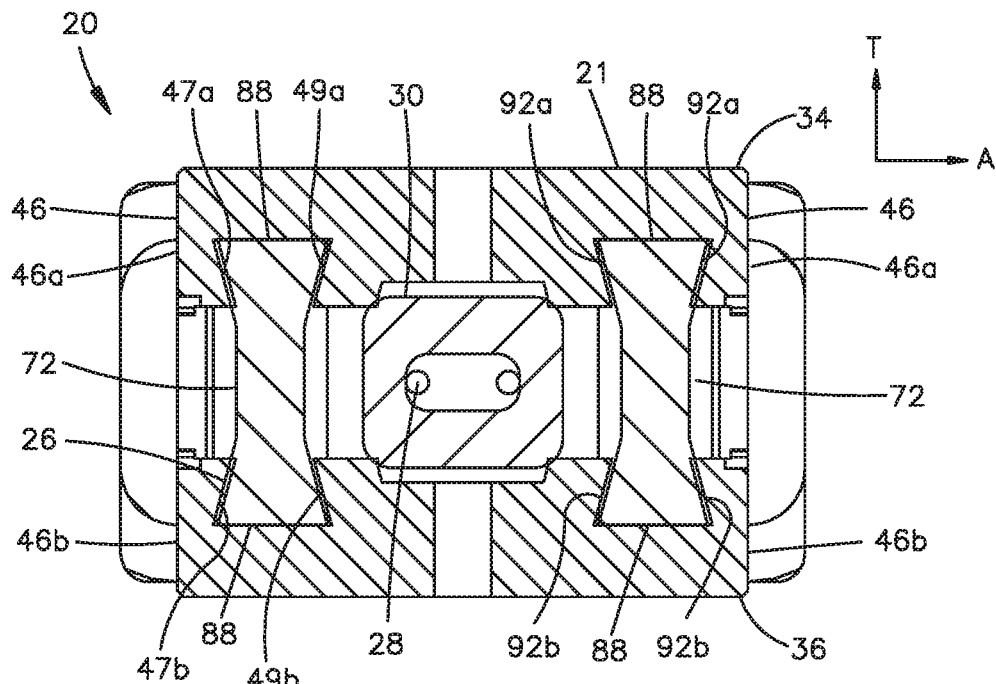
FIG. 10E is a perspective view of the intervertebral implant system illustrated in FIG. 10D, taken along line 10E-10E.

In particular, referring now to FIGS. 5B and 10E, the cage body 21 can further be configured to engage with the core 26 when the core 26 is inserted into the core channels 50 (see FIG. 4B) so as to limit expansion of the cage body 21 along the transverse direction when the core is inserted into the cage body 21. For instance, each of the arms 72 can define at least one core interlocking member 88 that is configured to engage the respective at least one cage interlocking member 47 of the cage body 21 so as to couple the core 26 to each of the upper vertebral engaging body 34 and the lower vertebral engaging body 36. For instance, each of the side surfaces 84 can define a concavity 90 as they extend along the transverse direction T. The concavity 90 can define an upper end 92a and a lower end 92b. The upper end 92a and the lower end 92b can be configured as projections that project outward along the lateral direction A to a position such that they are aligned with at least a portion of the upper side surfaces 49a and lower side surfaces 49b, respectively. Thus, the upper ends 92a and the lower ends 92b of each of the side surfaces of the arms 72 can define interlocking members that interlock with complementary interlocking members of the cage body 21 so as to couple the core 26 to each of the upper vertebral engagement body 34 and the lower vertebral engagement body 36.

In particular, when the arms 72 are inserted into the channels 50, the upper side surfaces 49a and the lower side surfaces 49b can be nested between the respective upper and lower ends 92a and 92b of the arms 72. Accordingly, abutment between the upper side surfaces 49a of the upper vertebral engagement body 34 and the upper ends 92a of the arms 72 prevents the upper vertebral engagement body 34 from moving away from the lower vertebral engagement body 36 along the transverse direction. Similarly, abutment between the lower side surfaces 49b of the lower vertebral engagement body 36 and the lower ends 92b of the arms 72 prevents the lower vertebral engagement body 36 from moving away from the upper vertebral engagement body 34 along the transverse direction. Thus, the upper and lower ends 92a and 92b of the arms 72 and the upper and lower side surfaces 49a and 49b of the upper and lower vertebral engagement bodies 34 and 36 define respective interlocking members that engage each other to prevent separation of the upper and lower vertebral engagement bodies 34 and 36. It should, however, be appreciated that the upper and vertebral engagement bodies 34 and 36 and the core 26 can define any alternatively designed interlocking members as desired suitable to couple the upper vertebral engagement body 34 to the lower vertebral engagement body 36 with respect to movement away from each other along the transverse direction T.

Figure 5C:
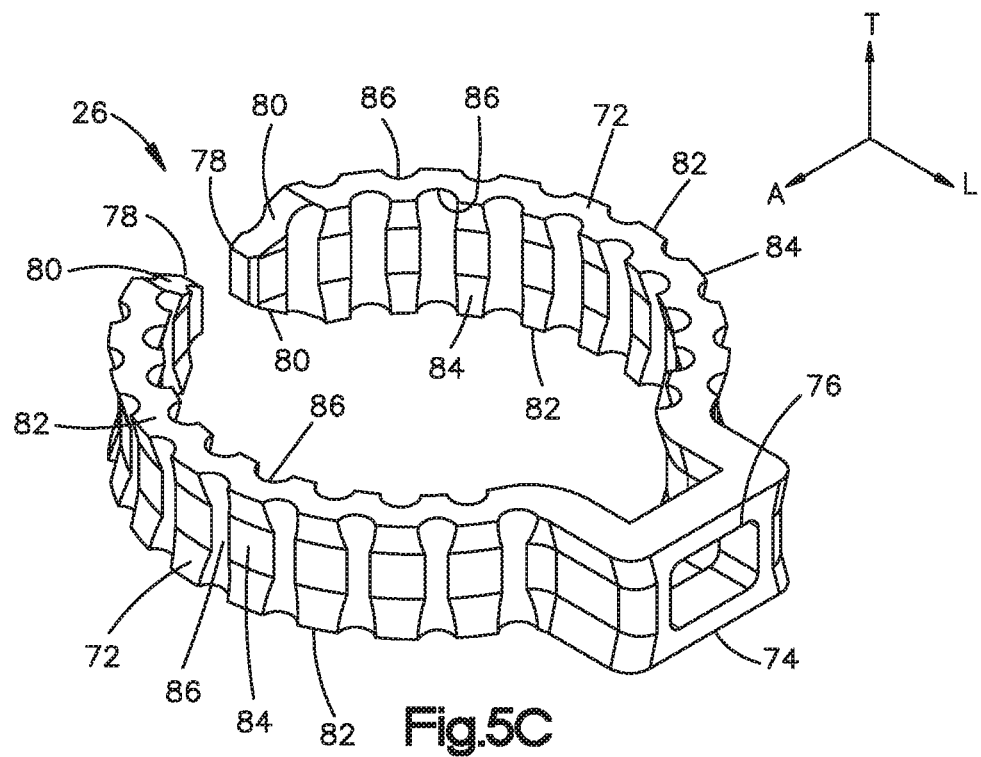
FIG. 5C is a perspective view of the core illustrated in FIG. 5A, but shown in a laterally expanded position.
Figure 5D:
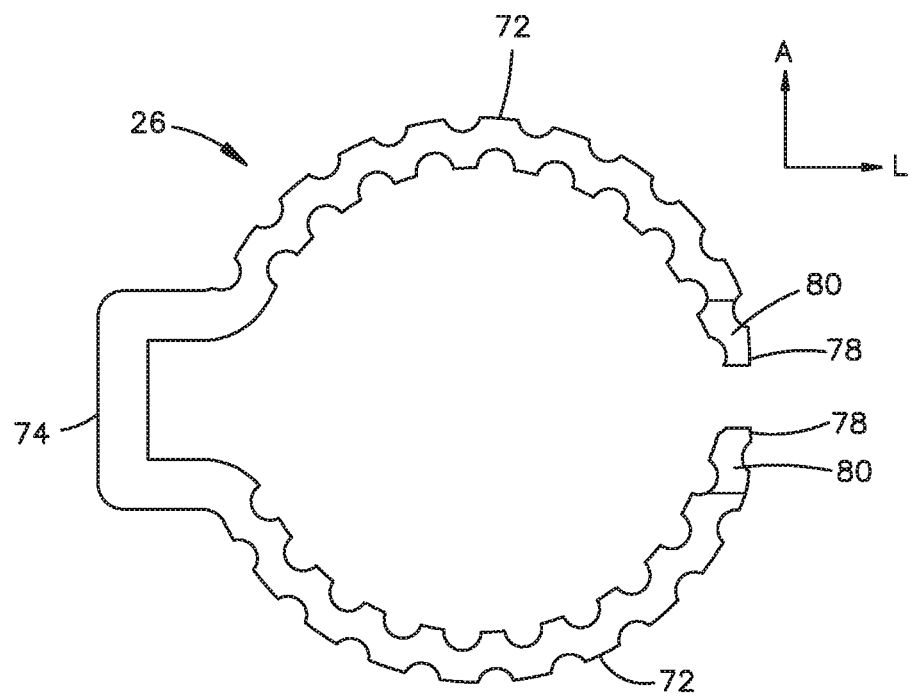
FIG. 5D is a top plan view of the core illustrated in FIG. 5C shown in the expanded lateral position.
Figure 5E:
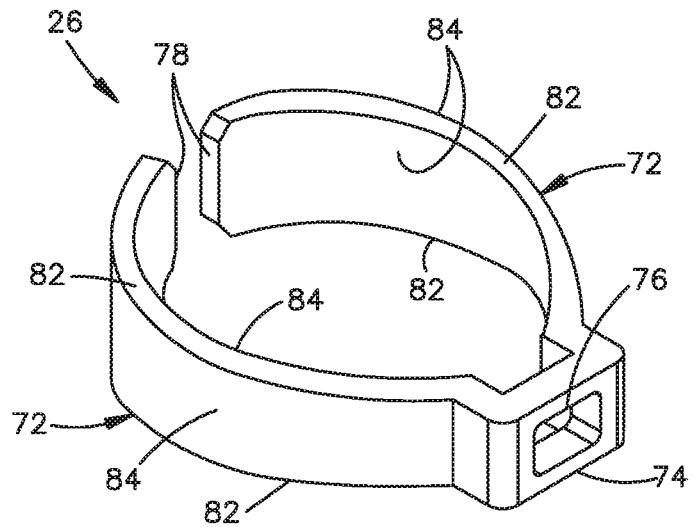
FIG. 5E is a perspective view of the core illustrated in FIG. 5A, but shown having a lordotic profile in accordance with an alternative embodiment.

Referring now to FIG. 5E, the core 26 can be tapered along the longitudinal direction L when the core 26 is in the expanded lateral position. In particular, the opposed transverse outer surfaces 82 of one or both of the arms 72 can be tapered along the length of the respective arm 72. In one example, the opposed outer surfaces 82 that are opposite each other along the transverse direction T can converge toward each other along the transverse direction T as they extend along the length of the respective arm 72. For instance, the opposed outer surfaces 82 that are opposite each other along the transverse direction T can converge toward each other along the transverse direction T as they extend in a direction opposite the insertion direction of the cage 20 into the intervertebral space. Thus, the opposed outer surfaces 82 that are opposite each other along the transverse direction T can converge toward each other along the transverse direction T as they extend along the length of the arm 72 away from the leading end 78. For instance, opposed outer surfaces 82 that are opposite each other along the transverse direction T can converge toward each other along the transverse direction T as they extend from the leading end 78 to the bridge 74. The taper can have a constant slope or a variable slope. The upper outer surfaces 82 can be coplanar with each other when the core 26 is in the expanded lateral position. Similarly, the lower outer surfaces 82 can be coplanar with each other when the core 26 is in the expanded lateral position.

As described above, the upper and lower engagement bodies 34 and 36 of the cage body 21 (see FIG. 3A) can rest on the opposed outer surfaces 82. Accordingly, when the transverse outer surfaces 82 are tapered, the upper and lower engagement bodies 34 that rest on the opposed outer surfaces 82 can likewise be tapered. Thus, the upper and lower engagement bodies 34 and 36 can converge toward each other along the transverse direction T as they extend in a direction opposite the insertion direction into the intervertebral disc space. It should thus be appreciated that the upper and lower engagement bodies 34 and 36 can define a lordotic profile when the cage 20 is inserted in an anterior approach into the intervertebral disc space.

Figure 5F:
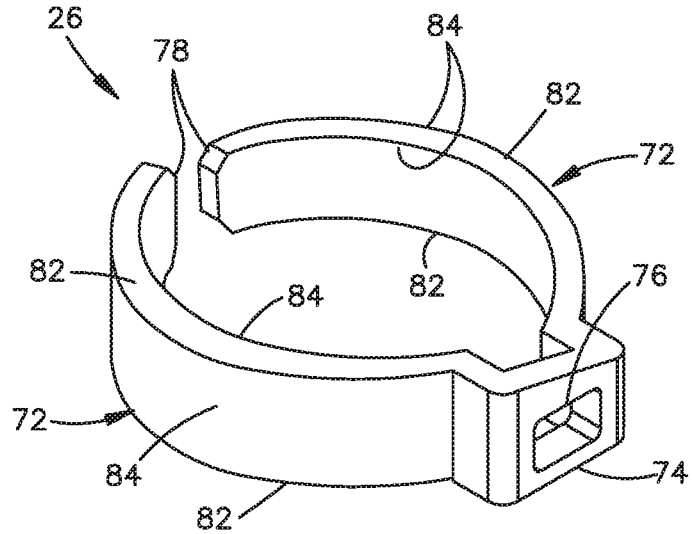
FIG. 5F is a perspective view of the core illustrated in FIG. 5A, but shown having a lordotic profile in accordance with an alternative embodiment.

Alternatively, referring to FIG. 5F, the core 26 can be tapered along the lateral direction. Thus, the upper and lower engagement bodies 34 and 36 of the cage body 21 can define a lordotic profile when the cage 20 is inserted in along a lateral approach into the intervertebral disc space. Thus, the core 26 can be tapered along the lateral direction A. In one example, each of the arms 72 can be tapered along the lateral direction A when the core 26 is in the expanded lateral position. For instance, the outer surfaces 82 of the arms 72 can be sloped in the same direction. The upper outer surfaces 82 can be coplanar with each other. Similarly, the lower outer surfaces 2 can be coplanar with each other. When the core 26 is inserted into the cage body, the upper and lower engagement bodies 34 and 36 can rest against the outer surfaces 82 of the core 26. Thus, when the core 26 is expanded to the expanded lateral position, the upper and lower engagement bodies 34 and 36 can be tapered toward each other along the transverse direction T as they extend along the lateral direction A. Thus, the cage 20 can be inserted into the intervertebral space in a lateral approach and can define a lordotic profile.

Figure 5G:
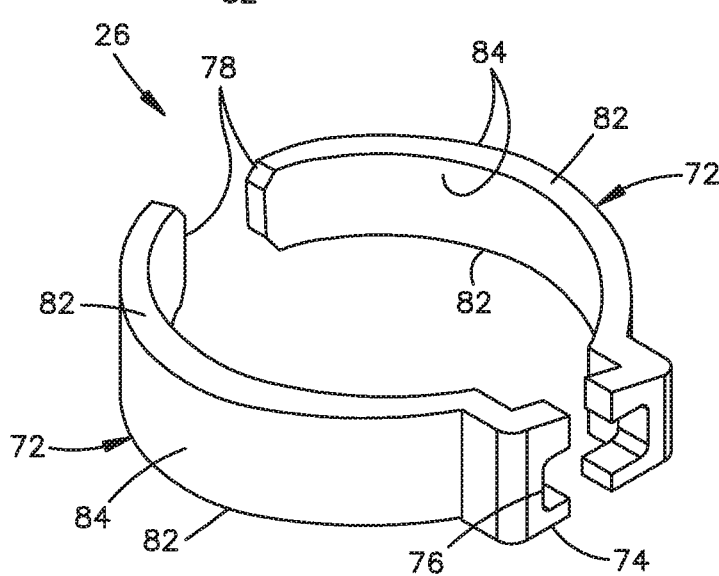
FIG. 5G is a perspective view of the core illustrated in FIG. 5A, but shown including first and second core segments in accordance with an alternative embodiment.

Referring to FIG. 5G, the core 26 can be tapered along the lateral direction A in accordance with an alternative embodiment. In particular, the arms 72 can define a taper along the lateral direction A when the cage 26 is in the expanded lateral position. However, while the arms 72 are joined to each other at the bridge 74 as illustrated in FIG. 5F, the arms 72 can be separate from each other in FIG. 5F.

As described above, the upper and lower engagement bodies 34 and 36 of the cage body 21 (see FIG. 3A) can rest on the opposed outer surfaces 82. Thus, when the arms 72 are rigid, the upper and lower engagement bodies 34 and 36 are rigidly supported by the arms 72. Accordingly, the rigid arms 72 prevent the upper and lower engagement bodies 34 and 36 from moving toward each other along the transverse direction T in response to anatomical compressive loading. Alternatively, referring now to FIGS. 5H-5I, at least a portion of one or both of the arms 72 can be compressible along the transverse direction T. Thus, anatomical compressive loading applied to the upper and lower engagement bodies 34 and 36 can cause the upper and lower engagement bodies 34 and 36 to compress toward each other as the arms 72 compress. Thus, the cage 20 can be a dynamic cage whose upper and lower vertebral engagement bodies 34 and 36 can move relative to each other in response to anatomical loading.

In one example, as illustrated in FIG. 5H, one or both of the arms 72 can include an upper wall 63a and a lower wall 63b that define a hollow interior space 65. The upper wall 63a can define the upper outer surface 82, and the lower wall 63b can define the lower outer surface 82. One or both of the arms 72 can each further include at least one spring member 67 that extends from one of the upper and lower walls 63s and 63b toward the other of the upper and lower walls 63a and 63b in the interior space 65. The at least one spring member 67 is configured to bear against the other of the upper and lower walls 63a and 63b, and has a corresponding spring force. The upper and lower walls 63a and 63b can be resilient. Thus, the at least one spring member 67 can bear against the other of the upper and lower walls 63a and 63b when a compressive force is applied to the upper and lower walls 63a and 63b. Accordingly, during use, when an anatomical compressive load is applied to the upper and lower vertebral engagement bodies 34 and 36, the upper and lower vertebral engagement bodies 34 and 36 urge the upper and lower walls to compress toward each other against the spring force of the at least one spring member 67. Each of the arms 72 can include more than one spring member having different spring constants to provide different levels of mobility along the respective lengths of the arms 72.

In another example, as illustrated in FIG. 5I, one or both of the arms 72 can include a plurality of zones having different levels of stiffness. For instance, one or both of the arms 72 can have at least first and second zones 73a and 73b of different elasticity along its respective length. The first zone 73a can be spaced from the second zone 73b along a direction opposite the direction of insertion into the intervertebral space. That is, the first zone 73a can be disposed between the bridge 73 and the second zone 73b. The first zone 73a can be stiffer than the second zone 73b. For instance, the first zone 73a can be made from a stiffer material than the second zones 73b. In another example, one or both of the arms 72 can include a third zone 73c having a stiffness that is less than the second zone 73b. The second zone 73b can be disposed between the first zone 73a and the third zone 73c along the length of the respective arm 72. Accordingly, during operation, when anatomical loads are applied to the upper and lower vertebral engagement bodies 34 and 36, those portions of the upper and lower vertebral engagement bodies 34 and 36 that are aligned with the third zone 73c along the transverse direction T can compress toward each other greater than those portions of the upper and lower vertebral engagement bodies 34 and 36 that are aligned with the second zone 73b along the transverse direction T. Similarly, those portions of the upper and lower vertebral engagement bodies 34 and 36 that are aligned with the second zone 73b along the transverse direction T can compress toward each other greater than those portions of the upper and lower vertebral engagement bodies 34 and 36 that are aligned with the first zone 73a along the transverse direction T.

Figure 7A:
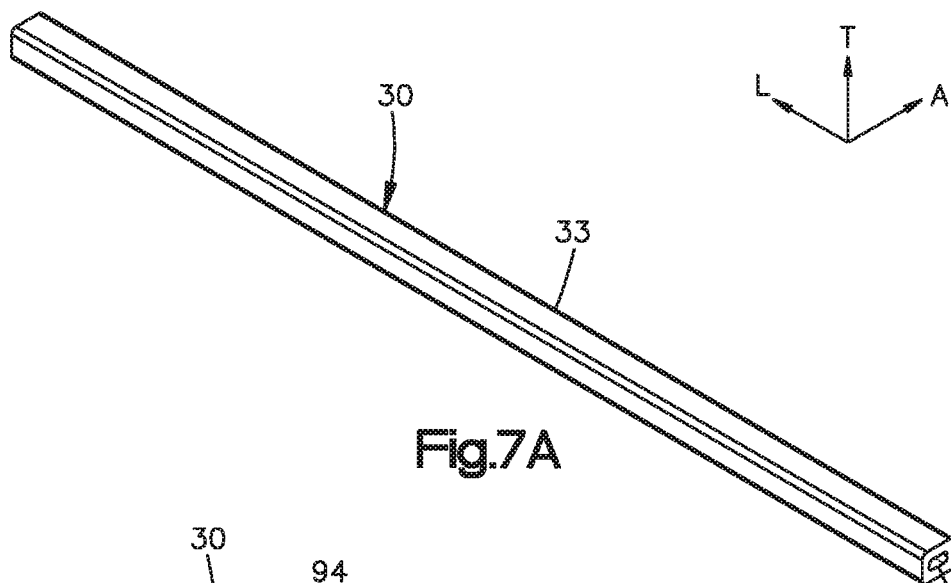
FIG. 7A is a perspective view of a handle configured to be inserted into the fusion cage when the fusion cage is in the initial position.
Figure 7B:
FIG. 7B is an end elevation view of the handle illustrated in FIG. 7A.

Referring now to FIGS. 7A-7B, and as described above with reference to FIG. 2, the instrumentation assembly 25 can further include the handle 30 that is configured to be inserted into the fusion cage 20 when the fusion cage is in the unexpanded lateral position and the unexpanded transverse position. The handle 30 can include a tube 33 that is elongate along the longitudinal direction T. The tube 33 can be sized to extend through the through hole through hole 76 of the core 26. The tube 33 can be further sized to extend in the handle-receiving channel 54 of the cage body 21. In one example, the tube 33 can be received in the channel 54 when the cage 20 is in the first lateral position and when the cage 20 is in the first transverse position. Additionally, the channel 54 can be sized such that the tube 33 remains received in the channel 54 when the cage 20 has been expanded to the expanded transverse position (see FIG. 10E). Thus, interference between the tube 33 and the surfaces of the cage body 21 that define the channel 54 prevent movement of the tube 33 out of the channel 54 in both the lateral direction A and the transverse direction T. It should be appreciated that when the tube 33 is disposed in the channel 54, the tube 33 can bear against the inner surfaces 52 of each of the upper and lower vertebral engagement bodies 34 and 36, and thus can resist tilting of the upper and lower vertebral engagement bodies 34 and 36 relative to each other.

Figure 7C:
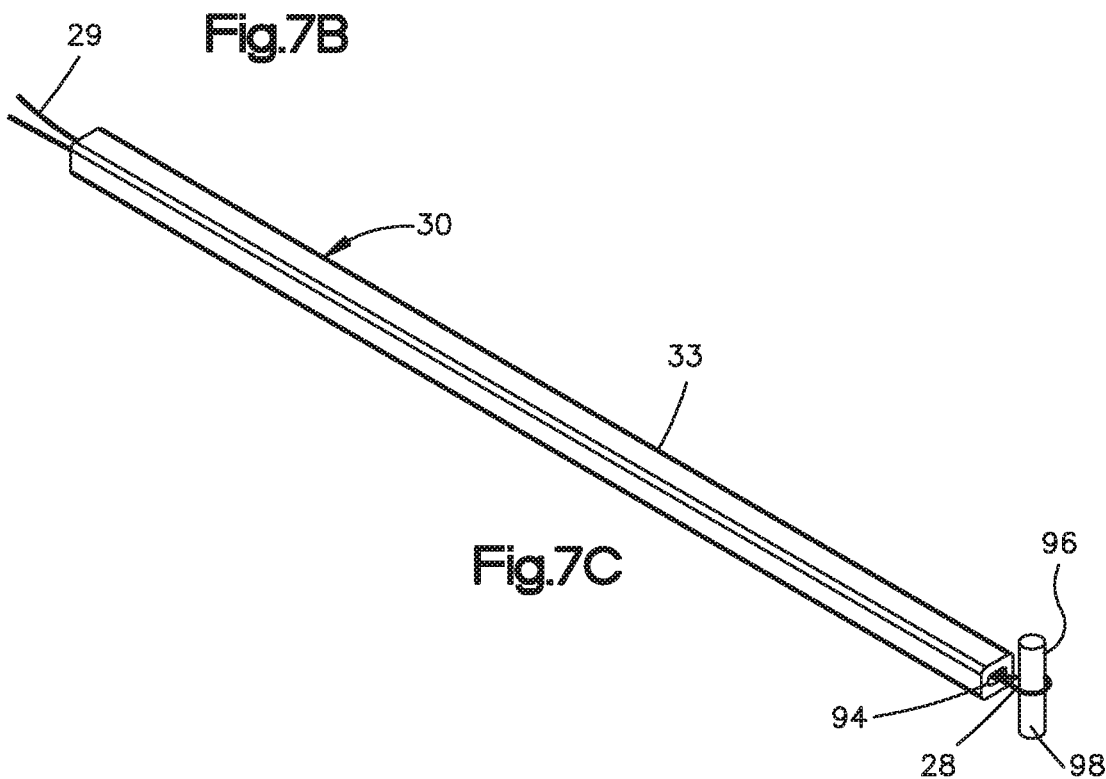
FIG. 7C is a perspective view of the actuation member disposed in the handle illustrated in FIG. 7A and coupled to an attachment post of the fusion cage.

Referring now to FIG. 7C, the handle 30 can further define a through hole 94 that extends through the tube 33 along the longitudinal direction L. The through hole 94 can be sized to receive the actuation member 28. In particular, the actuation member 28 is configured to attach to a complementary actuation structure 96 of the cage body 21. The actuation member 28 is configured to apply an actuation force to the actuation structure 96 that causes the cage body 21, and thus the core 26, to move from the first lateral position to the expanded lateral position. In one example, the actuation force can be a compressive force applied to one of the leading and trailing ends of the cage body 21 toward the other one of the leading and trailing ends of the cage body 21. The actuation structure 96 can be attached to the leading end of the cage body 21. Thus, the actuation member 28 can apply the actuation force to the actuation structure 96 in a direction toward the trailing end of the cage body 21. The actuation member 28 can be configured as a thread, wire, cable, or other suitable flexible elongated member.

In one example, the actuation structure 96 can be a post 98 that is coupled to each of the leading upper and lower links 66a and 66b of the cage body 21. The post 98 can be coupled to each of the leading upper and lower links 66a and 66b when the cage body 21 is in the first transverse position. Further, the post 98 can be coupled to each of the leading upper and lower links 66a and 66b of the cage body 21 when the cage body 21 is in the expanded transverse position. For instance, the post 98 can be fixed to one of the upper and lower links 66a and 66b, and can extend into or through a bore that extends through the other of the upper and lower links 66a and 66b along the transverse direction T. Thus, the post 98 is slidably received in the other of the upper and lower links 66a and 66b along the transverse direction T. Accordingly, when the cage body 21 is in the expanded transverse position, the post 98 can remain in the bore of the other of the upper and lower links 66a and 66b.

The actuation member 28 can be a flexible member that can be looped around the post 98. For instance, the actuation member 28 can be a string, a wire, or any flexible member suitable to be looped around the post 98. The actuation member 28 can extend into the rear end of the through hole 94 of the tube 33, out the front end of the through hole 94, can loop around the post 98, and can extend again out the rear end of the through hole 94. Thus, the actuation member can extend from the post 98 and into the through hole 94. The actuation member 28 defines first and second free ends 29 that can be gripped and pulled rearward so as to apply the actuation force to the leading end of the cage body. In particular, the actuation force can be applied to the post 98 from the actuation member 28, which causes the post to urge the leading end links 66a and 66b in the rearward direction toward the trailing end of the cage body 21. The free ends 29 of the actuation member 28 can extend out the rear end of the tube 33. In this regard, the tube 33 can be referred to as both a handle tube and a guide tube that guides the actuation member 28 to the post 98. The tube 33 prevents the actuation member 28 from being brought into contact with other movable components of the cage 20, such as the core and the cage body 21. The actuation member can be configured as a string that can be made out of fiber or plastic, a wire that can be made out of metal, or any suitable metallic or nonmetallic member. It should be appreciated that numerous alternative embodiments of actuation members 28 and actuation structures 96 are envisioned, and the actuation member 28 and actuation structure 96 are not to be limited to the structures described herein, unless otherwise indicated.

Figure 8A:
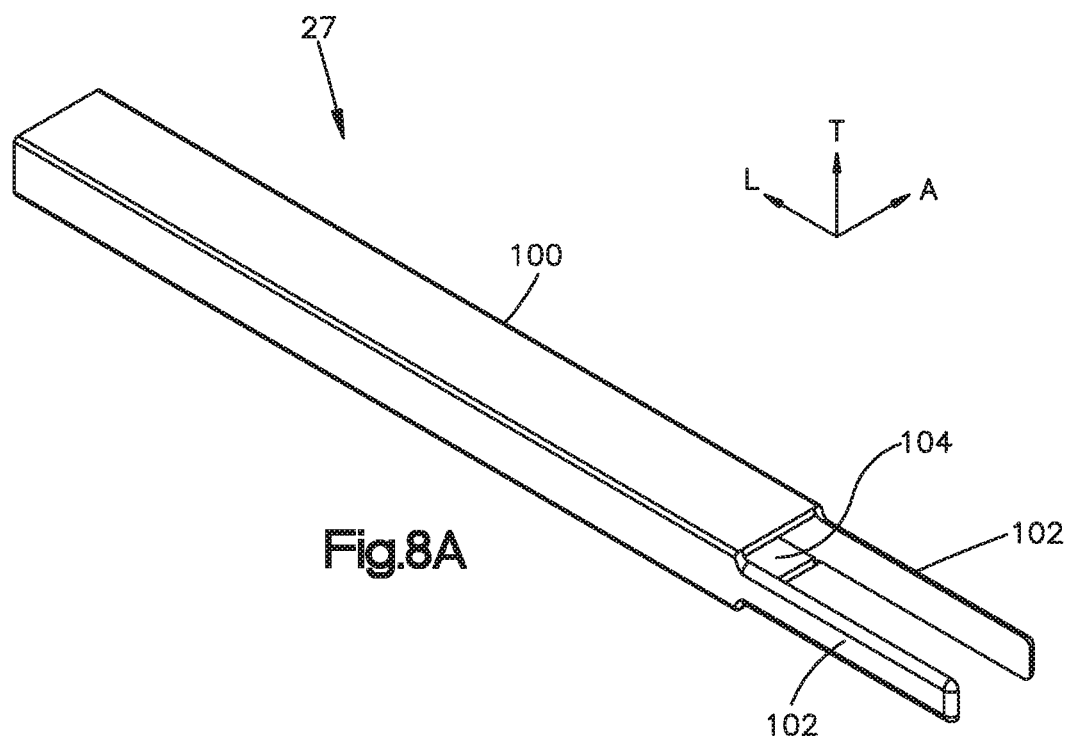
FIG. 8A is a perspective view of a retainer that is configured to engage opposed outer surfaces of the fusion cage.
Figure 8B:
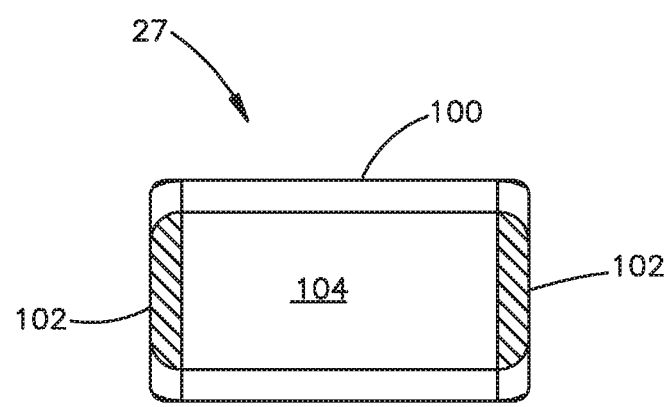
FIG. 8B is an end elevation view of the retainer illustrated in FIG. 8A.

Referring now to FIGS. 8A-8B, and as described above with reference to FIG. 2, the instrumentation assembly 25 can further include the retainer 27. The retainer 27 is configured to engage the cage body 21 so as to prevent the cage body 21 from expanding along the lateral direction from the first lateral position to the expanded lateral position. The retainer 27 can include a retainer housing 100 and a pair of retainer arms 102 that extend out from the retainer housing 100. The retainer arms 102 can extend from the retainer housing 100 along the longitudinal direction. The retainer arms 102 can be configured to engage respective ones of the first and second side walls 46 so as to prevent the side walls 46 from moving away from each other along the lateral direction. In particular, the retainer arms 102 can be spaced from each other along the lateral direction A a sufficient distance such that the retainer arms 102 abut the outer surfaces of the side walls 46. The retainer arms 102 can be resilient and flexible, and can deflect away from each other when they extend along the side walls 46, such that the retainer arms 102 apply a compressive force along the lateral direction to the side walls 46. Alternatively, the retainer arms 102 can be substantially rigid. During operation, the retainer arms provide an interference with the side walls 46 that prevent the side walls from moving away from each other.

The retainer 27 can define a through hole 104 that extends through the retainer housing 100 along the longitudinal direction. The through hole 104 can extend out the front end of the retainer housing 100 at a location between the retainer arms 102 with respect to the lateral direction, and can further extend out the rear end of the retainer housing 100. The through hole 104 can be sized to receive the handle 30, the pusher member 32, and the core 26 (see FIG. 2).

Figure 9A:
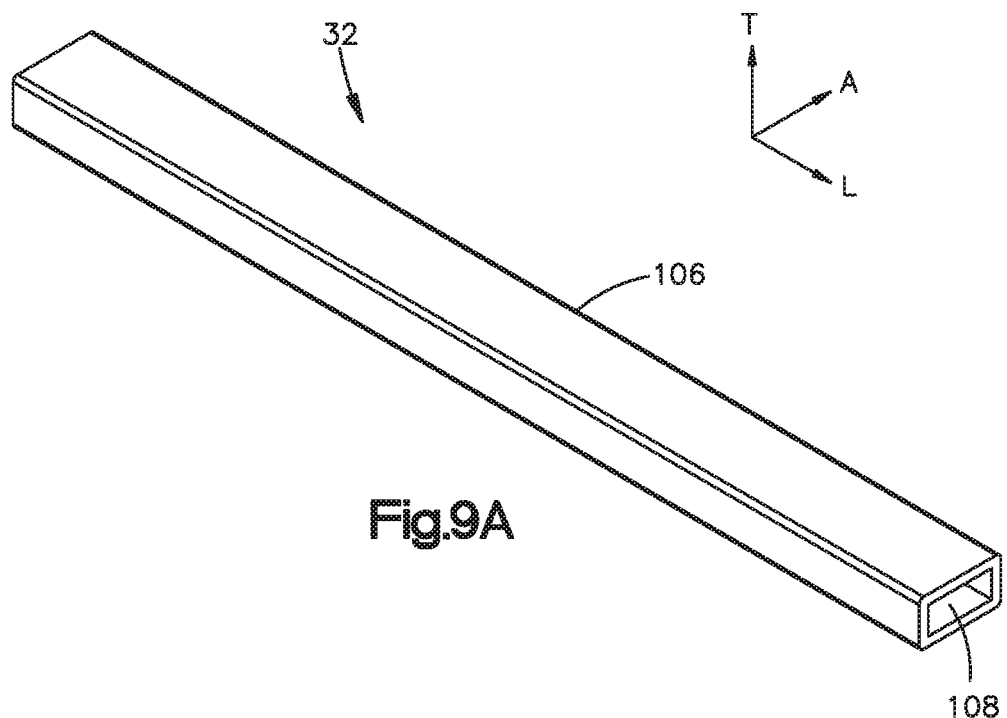
FIG. 9A is a perspective view of a pusher member that is configured to pusher member against the fusion cage as the fusion cage expands from the unexpanded lateral position to the expanded lateral position.
Figure 9B:
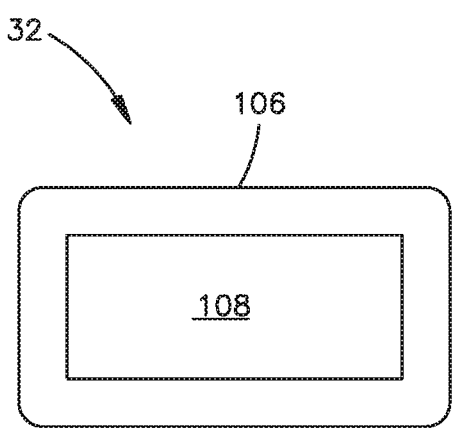
FIG. 9B is an end elevation view of the pusher member illustrated in FIG. 9A.

Referring now to FIGS. 9A-9B, and as described above with reference to FIG. 2, the instrumentation assembly 25 can further include the pusher member 32. The pusher member 32 includes a pusher body 106. The pusher body 106 can be elongate along the longitudinal direction L, and can be sized to be received in the through hole 104 of the retainer 27 (FIGS. 8A-8B). The pusher member 32 can define a through hole 108 that extends through the pusher body 106 along the longitudinal direction L. The through hole 108 can be sized to receive the handle 30. Thus, the handle 30 can extend from the through hole 108 of the pusher body 106 into the cage body 21. The through hole 108 can be smaller than the core 26 in cross section in a plane defined by the lateral direction A and the transverse direction T. The through hole 108 can thus also be smaller than trailing end of the cage body 21 in cross section in a plane defined by the lateral direction A and the transverse direction T.

Accordingly, during operation, the front end of the pusher body 106 can abut the core 26 and apply a force to the core in the forward direction that urges the core 26 into the cage body 21 in the manner described above. Further, the front end of the pusher body 106 can abut the trailing end of the cage body 21 so as to brace the cage body 21 as the actuation member applies the actuation force to the leading end of the cage body 21. Thus, when the trailing end of the cage body 21 is braced, the actuation force causes compression between the leading ends and the trailing end that causes the cage 20 to move from the first lateral position to the expanded lateral position. In this regard, the pusher member 32 can be referred to as a brace member. While the pusher member is a single member that is configured to push the core 26 into the cage body 21, and also brace the cage body 21, it should be appreciated that the instrumentation assembly 25 can alternatively include a dedicated pusher member that is configured to push the core 26 into the cage body 21, and a separate dedicated brace member that is configured to brace the trailing end as the actuation force is applied to the leading end.

Operation of the intervertebral implant system 23 will now be described with reference to FIGS. 10A-10G. It should be appreciated that the description of operation with respect to FIGS. 10A-10G equally applies to the operation of the intervertebral implant system 23 alternatively including the cage body 21 shown and described above with respect to FIGS. 4A-4C unless otherwise indicated. As illustrated in FIG. 10A, the retainer 27 can be inserter over the pusher member 32 such that the pusher member 32 extends through the through hole 104 of the retainer 27. The retainer arms 102 can extend forward with respect to the pusher member 32 along the longitudinal direction L. The handle 30 can extend through the through hole 108 of the pusher member 32 and into the cage body 21. Thus, the cage body 21 is secured to the instrumentation assembly 25, and a user can grip the instrumentation assembly 25 so as to move the cage body 21 to a desired location. For instance, the user can grip one or both of the pusher member 32 and the retainer 27. Alternatively or additionally, the handle 30 can extend rearwardly out of the through hole 108 of the pusher member 32, and the handle 30 can be gripped by the user. The actuation member 28 can extend through the through hole 94 of the handle 30 and around the actuation post 98 as described above with reference to FIG. 7C. The core 26 can be at least partially disposed in the through hole 104 of the retainer. The front end of the pusher member 32 can be disposed rearward of the core 26.

Referring now to FIG. 10B, the fusion cage 20 can be implanted into the intervertebral disc space 22. In one example, the fusion cage 20 can be inserted in a TLIF approach to the disc space 22. It should be appreciated, of course, that the fusion cage 20 can alternatively be inserted into the disc space 22 along any suitable alternative approach as desired. The retainer 27 can be translated in the forward or insertion direction relative to the cage body 21 to an engaged position whereby the retainer arms 102 are aligned with the sides 46 of the cage body 21 along the lateral direction A. Interference between the sides 46 and the retainer arms 102 can prevent or minimize expansion of the cage body 21 along the lateral direction from the first lateral position toward the expanded lateral position. It may be desirable to move the retainer 27 to the engaged position before the fusion cage 20 is inserted into the disc space 22. It should be appreciated, however, that the retainer 27 can alternatively be moved to the engaged position after the fusion cage 20 has been inserted into the disc space 22.

Next, referring to FIG. 10C, the fusion cage 20 can then be moved from the first transverse position to the expanded transverse position. In particular, the pusher member 32 can be translated forward in the through hole 104 of the retainer 27. As the pusher member 32 translates forward, the front end of the pusher member abuts the core 26 and pushes the core 26 in the forward direction. The free ends of the actuation member 28 can be gripped to prevent movement of the cage body 21 in the forward direction due to frictional forces between the core 26 and the cage body 21 as the core 26 is inserted into the core 26. However, engagement between the side walls 46 and the retainer arms 102 prevent the side walls 46 from moving away from each other along the lateral direction A. The retainer arms 102 can remain engaged with the side walls 46 after the cage body 21 has expanded to the expanded transverse position. As described above, as the core 26 is pushed into the cage body 21, the core 26 pushes the upper and lower vertebral engagement bodies 34 and 36 away from each other to the expanded transverse position. In some examples, the ribs 48 can rupture as the cage body 21 expands to the expanded transverse position.

Next, as illustrated in FIG. 10D, the retainer 27 can be retracted rearward away from the cage 20 until the retainer 27 is in a disengaged position whereby retainer arms 102 are free from engagement with the side walls 46. Thus, the retainer arms 102 no longer prevent the cage 20 from expanding from the first lateral position to the expanded lateral position. For instance, when the retainer 27 is in the disengaged position, the retainer arms 102 can be in a position such that no portion of the retainer arms 102 is aligned with the side walls 46 along the lateral direction A. As illustrated in FIG. 10E, when the core 26 is disposed in the cage body 21, the core 26 can be coupled to each of the upper and lower intervertebral engagement bodies 34 and 36 to prevent further separation of the upper and lower intervertebral engagement bodies 34.

Figure 10F:
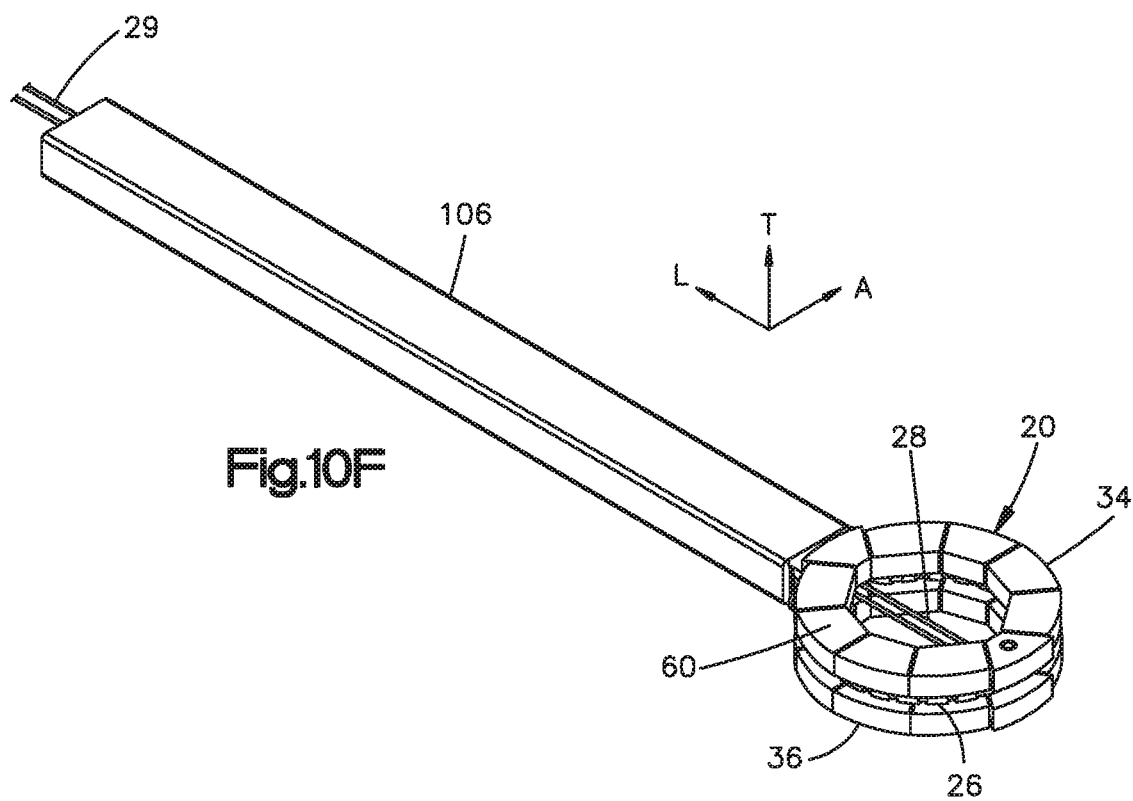
FIG. 10F is a perspective view of the intervertebral implant system illustrated in FIG. 10C, showing the fusion cage laterally expanded to the expanded lateral position.
Figure 10G:
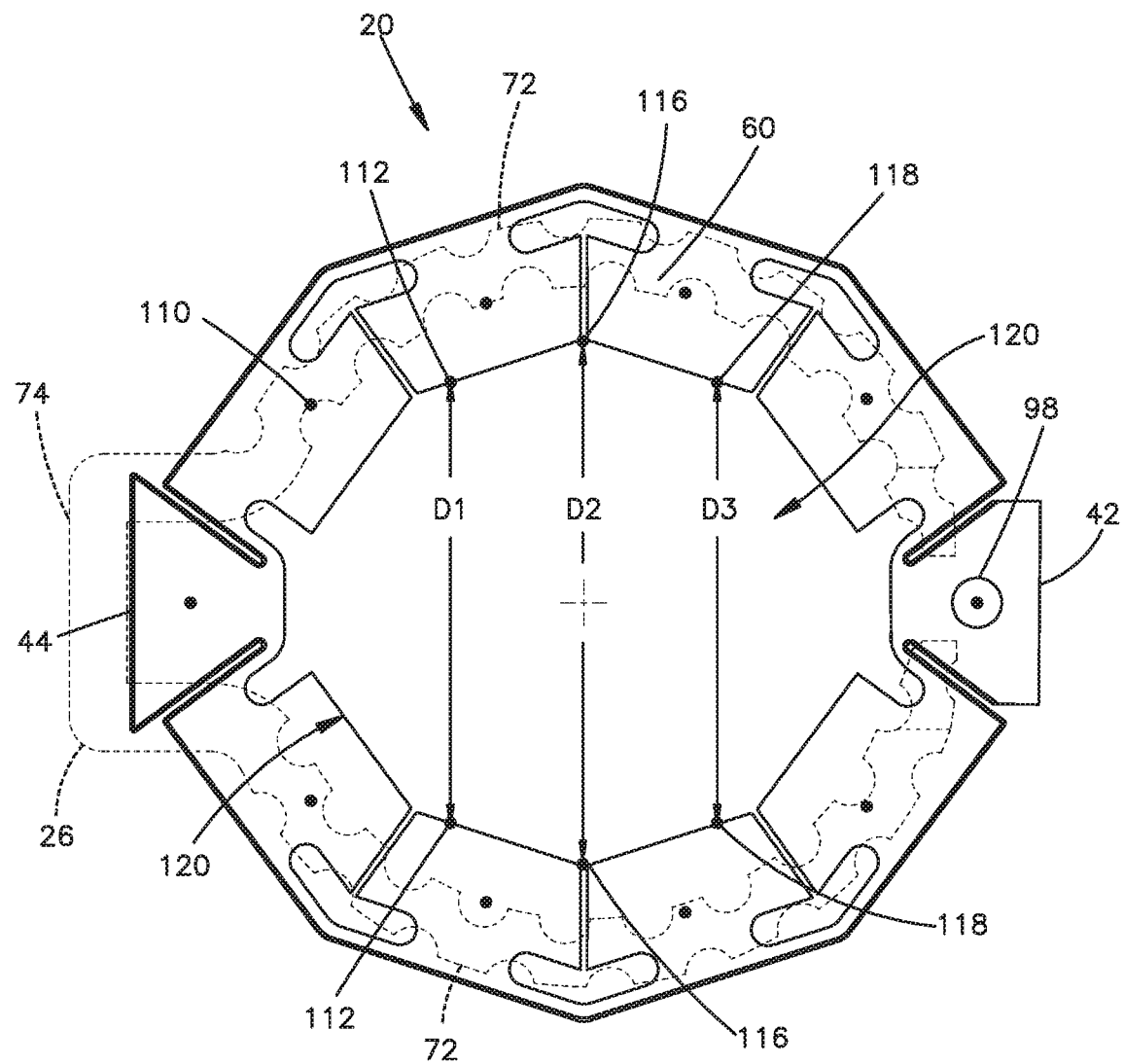
FIG. 10G is a top plan view of the intervertebral fusion cage illustrated in FIG. 10E.

Finally, referring to FIGS. 10F-10G, the fusion cage 20 can be expanded from the first lateral position to the expanded lateral position. In particular, the front end of the pusher member 32 can be placed in abutment with the trailing end of the fusion cage 20. The trailing end of the fusion cage 20 can be defined by the bridge 74 of the core 26 (see FIGS. 5A-5D) or can be defined by the upper and lower trailing links 68a and 68b. Thus, the front end of the pusher member 32 can brace the cage body 21 with respect to movement of the cage body 21 in the rearward direction. Thus, the pusher member 32 can prevent movement of the cage body 21 in the rearward direction. With the pusher member 32 braced against the cage body 21, the actuation member 28 can be gripped and pulled in the rearward direction, thereby applying the actuation force to the cage body 21. In particular, the free ends of the actuation member 28 can be pulled in the rearward direction, which applies a rearward force to the leading end of the cage body 21. For instance, as descried above, the actuation member 28 can apply the rearward actuation force to the post 98, which thus applies the actuation force to the leading end of the cage body. Because the pusher member 32 is braced against the cage body 21, the actuation force results in the application of a compression force to the leading and trailing ends of the cage body 21.

Once the fusion cage 20 has been moved to the expanded lateral position, the free ends of the actuation member 28 can be tied together at a location adjacent and rearward of the trailing end of the cage body 21 to secure the cage body 21 in the expanded lateral position. Thus, because the actuation member 28 can remain engaged with the cage body after completion of the surgical procedure, the actuation member 28 can be considered to be part of the fusion cage 20. Alternatively, the cage body 21 can include mechanical locking members that engage the first and second side walls 46 in the expanded lateral position, thereby preventing the cage body 21 from moving in a direction toward the first lateral position. Thus, the actuation member 28 can be removed from the fusion cage 20 after the mechanical locking members have engaged each other. Alternatively or additionally, frictional forces between the vertebral bodies and the cage 20, and in particular the upper and lower vertebral engagement bodies 34 and 36, can prevent the cage body 21 from moving in a direction toward the first lateral position. The frictional forces can be increased by providing one or more of spikes, teeth, ridges, grooves, textures or coatings such as a TI sprayed coating to the upper and lower vertebral engagement bodies 34 and 36.

The cage body 21 is thus responsive to the actuation force to move from the first lateral position to the expanded lateral position. Once the cage body 21 has been expanded to the expanded lateral position, the handle 30 can be removed from the cage body 21. In one example, at least respective portions of the first and second side walls 46 can be movable away from each other different distances so as to expand the intervertebral fusion cage 20 from the first lateral position to the expanded lateral position. Further, at least respective portions of the first and second side walls 46 can be movable away from each other different rates so as to expand the intervertebral fusion cage 20 from the first lateral position to the expanded lateral position. In particular, the cage body 21 can define a substantially circular shape in a plane defined by the lateral direction and the longitudinal direction L when the cage body 21 is in the expanded lateral position. Thus, geometric centerlines 110 that extend centrally through each of the respective links 60, 66, and 68 along the transverse direction T can lie substantially on a circular path. Thus, the cage body 21 can define a circle or can approximate a circle (depending on whether the outer side surfaces of the side walls are curved or flat) in the plane that is defined by the lateral direction A and the longitudinal direction L. For instance, each of the upper and lower vertebral engagement bodies 34 and 36 can at least approximate the circle. In one example, each of the upper and lower vertebral engagement bodies 34 and 36 can define the circle. Whether the cage body 21 approximates a circle or defines a circle, it can be said that the cage body 21 substantially defines a circle shape because a circle can be drawn that overlaps in its entirety the links 60 of the cage body 21 along the transverse direction T. Thus, in one example, no part of the circle is disposed radially inwardly of any of the links, and no part of the circle is disposed radially outward of any of the links 60. The upper and lower vertebral engagement bodies 34 and 36 can be substantially identical to each other in size and shape both when the cage body 21 is in the first transverse position and the expanded transverse position, and when the cage body 21 is in the first lateral position and the expanded lateral position.

It should thus be appreciated that when the cage body 21, and thus the cage 20, is in the expanded lateral position, the cage body 21 can be at least substantially symmetrical about a plane that is defined by the longitudinal direction L and the transverse direction T. Further, respective first locations 112 of the first and second side walls 46 can be spaced from each other a first distance D1 along the lateral direction A. The first distance D1 can be measured along the lateral direction A. The first locations 112 can be spaced from both the trailing end 44 and a midline 114 with respect to the longitudinal direction L. The midline 114 can be equidistantly spaced from the leading and trailing ends 42 and 44, respectively, along the longitudinal direction L. Thus, the midline 114 can be oriented along the lateral direction A. Respective second locations 116 of the first and second side walls 46 can be spaced from each other along the lateral direction A a second distance D2 that is greater than the first distance. The second distance D2 can be measured along the lateral direction A. The second locations 116 are different than the first locations 112, and are thus offset from the first locations 112 along the longitudinal direction L. In one example, the second locations 116 can lie substantially on the midline that is equidistantly spaced from the leading and trailing ends 42 and 44 with respect to the longitudinal direction L.

Respective third locations 118 of the first and second side walls 46 can be spaced from each other along the lateral direction A a third distance D3 that is less than the second distance D2. The third distance D3 can be measured along the lateral direction A. The third locations 118 are different than each of the first locations 112 and the second locations 116, and are thus offset from the first and second locations 112 and 116 along the longitudinal direction L. The second locations 116 can be disposed between the first and third locations 112 and 118 with respect to the longitudinal direction L. For instance, the second locations 116 can be equidistantly spaced from each of the first and third locations 112 and 118 with respect to the longitudinal direction L. The first locations 112 can be spaced from the trailing end 44 an equal distance that the third locations 118 are spaced from the leading end 42. The first distance D1 can thus be equal to the third distance D3.

As described above with respect to FIGS. 5A-5D, the core 26 is flexible, and thus also movable from a respective first lateral position to a respective expanded lateral position. In particular, the core arms 72 are disposed in the respective core-receiving channels 50. Thus, when the cage body 21 moves to the expanded lateral position, the cage body 21 causes the core 26 to similarly move to its respective expanded lateral position. In particular, the core 26 can define a circular profile as described above with respect to the cage body 21. Thus, the core 26 can define respective first, second, and third locations as described above with respect to the cage body 21.

While the actuation member 28 can apply the actuation force to the cage body 21 which, in turn, causes the core to move to its expanded lateral position, it should be appreciated that the actuation member 28 can alternatively apply the actuation force to the core 26 which moves to the respective expanded lateral position. As the core 26 moves to the expanded lateral position, the core 26 can cause the cage body 21 to move to its expanded lateral position.

When the cage 20 is in the expanded lateral position, both the cage body 21 and the core 26 can be annular. Thus, the cage 20 can be annular in the expanded lateral position. Accordingly, the cage 20 can define a through hole 120 extending therethrough along the transverse direction T. The through hole 120 can be filled with a flowable biologic material after insertion into the disc space 22 to assist with fusion to the vertebral bodies 24. Further, flowable biologic material can be introduced through the through hole 108 of the pusher member 32 (see FIGS. 9A-9B) and into the through hole 120 when the cage body 21 is in the expanded lateral position.

It should be appreciated that inner surfaces of certain ones of the links 60 that face the through hole 120 can define a length along a plane that is defined by the longitudinal direction L and the lateral direction A. The links 60 can include outer surfaces opposite the inner surfaces that have a length along the plane that is greater than the length of the inner surfaces. Alternatively, the inner and outer surfaces of one or more of the links 60 can have substantially equal lengths. It should be appreciated that the term "substantially" as used herein can indicate variations appreciated by one having ordinary skill in the art. In one example, variations can be caused by manufacturing tolerances, though it should be appreciated that variations can be caused by other factors as well, including by design.

The intervertebral fusion cage of the present invention may be manufactured from any biocompatible material commonly used in interbody fusion procedures. In some embodiments, the cage is made from a composite comprising 40-99% polyarylethyl ketone PAEK, and 1-60% carbon fiber. Such a cage is radiolucent. Preferably, the polyarylethyl ketone PAEK is selected from the group consisting of polyetherether ketone PEEK, polyether ketone PEKK, polyether ketone ether ketone ketone PEKEKK, and polyether ketone PEK. Preferably, cage is made from woven, long carbon fiber laminates. Preferably, the PAEK and carbon fiber are homogeneously mixed. Preferably, the composite consists essentially of PAEK and carbon fiber. Preferably, the composite comprises 60-80 wt % PAEK and 20-40 wt % carbon fiber, more preferably 65-75 wt % PAEK and 25-35 wt % carbon fiber. In some embodiments, the cage is made from materials used in carbon fibers cages marketed by DePuy Synthes Spine, Raynham, Mass., USA. In some embodiments, the material is PEEK-OPTIMA, available from Invibio of Greenville, N.C.

In other embodiments, the cage is made from a metal such as titanium alloy, such as Ti-6Al-4 alloy, a titanium nitride (TIN) alloy, and a titanium-aluminum-niobium (TAN) alloy. In other embodiments, the cage is made from an allograft material. In some embodiments, the cage is made from ceramic, preferably a ceramic that can be at least partially resorbed, such as HA or TCP. In other embodiments, the ceramic comprises an oxide such as either alumina or zirconia. In some embodiments, the cage is made from a polymer, preferably a polymer that can be at least partially resorbed, such as PLA or PLG, or any suitable alternative implantable polymer.

In preferred embodiments, the cage is provided in a sterile form.

In summary, the cage implant of the present invention distracts the disc space during insertion. It is easy to insert and optimizes clinical performance once in place because it resists migration and subsidence due to the distribution of anatomical loads along the upper and lower vertebral engagement surfaces 34 and 36, has an appropriate stiffness for load sharing, is preferably radiolucent and has a shape that is able to contain injected graft material such as growth factors. In addition, the cage is robust over a wide variation of surgical technique because it will not break even when large forces are applied thereto.

The cage of the present invention is compatible with the broad use of injectable paste-like bone grafting materials, such as BMP-containing pastes because it is designed to be inserted empty and then filled with graft in-situ.

It should be noted that the illustrations and discussions of the embodiments shown in the figures are for exemplary purposes only, and should not be construed limiting the disclosure. One skilled in the art will appreciate that the present disclosure contemplates various embodiments. Additionally, it should be understood that the concepts described above with the above-described embodiments may be employed alone or in combination with any of the other embodiments described above. It should be further appreciated that the various alternative embodiments described above with respect to one illustrated embodiment can apply to all embodiments as described herein, unless otherwise indicated.

We claim:
1. An intervertebral fusion cage comprising:
a cage body that defines a leading end with respect to a direction of insertion into an intervertebral space, a trailing end opposite the leading end along a longitudinal direction, an upper vertebral engagement body that defines an upper vertebral contacting surface, a lower vertebral engagement body that defines a lower vertebral contacting surface spaced from the upper vertebral contacting surface along a transverse direction that is substantially perpendicular with respect to the longitudinal direction, and first and second side walls that extend between the leading end and the trailing end, the first and second side walls opposite each other along a lateral direction that is substantially perpendicular to each of the longitudinal direction and the transverse direction, wherein the lower and upper vertebral engagement bodies are separated from each other by a gap of the cage body that extends from a distal-most surface of the leading end to a proximal-most surface of the trailing end such that the lower and upper vertebral engagement bodies are movable away from each other in their respective entireties along the transverse direction so as to expand the intervertebral fusion cage from a first transverse position to an expanded transverse position, and wherein at least respective portions of the first and second side walls are movable away from each other different distances so as to expand the intervertebral fusion cage from a first lateral position to an expanded lateral position, whereby in the expanded lateral position the first and second side walls are spaced from each other along the lateral direction a first distance at a first location spaced from both the trailing end and a midline between the leading end and the trailing end with respect to the longitudinal direction, and the first and second side walls are spaced from each other along the lateral direction a second distance at a second location between the first location and the leading end, the second location is different than the first location, and the second distance is greater than the first distance.

2. The intervertebral fusion cage of claim 1, wherein the first and second side walls are movable away from each other different distances along their respective lengths such that the first and second side walls are spaced from each other along the lateral direction a third distance at a third location that is disposed between the second location and the leading end, the third distance less than the second distance.

3. The intervertebral fusion cage of claim 2, wherein the first and third locations are spaced from the leading and trailing ends, respectively, the same distance with respect to the longitudinal direction, and the first distance is substantially equal to the third distance.

4. The intervertebral fusion cage of claim 3, wherein the second location is disposed substantially on the midline between the leading end and the trailing end with respect to the longitudinal direction.

5. The intervertebral fusion cage of claim 4, wherein when the intervertebral fusion cage has expanded a maximum distance along the lateral direction, the first and second side walls combine so as to define a substantially circular profile along a plane that includes the longitudinal direction and the lateral direction.

6. The intervertebral fusion cage of claim 1, wherein when the intervertebral fusion cage is in the first lateral position, the first and second side walls are oriented substantially parallel to each other.

7. The intervertebral fusion cage of claim 6, wherein the first and second side walls each comprise a plurality of links and joints that pivotally join adjacent ones of the links to each other, the adjacent ones of the links being adjacent along the longitudinal direction when the intervertebral fusion cage is in the first lateral position.

8. The intervertebral fusion cage of claim 7, wherein when the cage is in the first lateral position,
1) at least a plurality of the links of the first side wall define respective wedges so as to define gaps disposed between adjacent ones of the links of the first side wall;
2) at least a plurality of the links of the second side wall define respective wedges so as to define gaps disposed between adjacent ones of the links of the first side wall;
3) the gaps of the first side wall taper outwardly as they extend toward the second side wall, and
4) the gaps of the second side wall taper outwardly as they extend toward the first side wall.

9. The intervertebral fusion cage of claim 8, wherein the gaps of the first side wall face respective ones of the gaps of the second side wall, and the gaps of the first and second side walls are substantially identical to each other in size and shape.

10. The intervertebral fusion cage of claim 8, wherein outermost ones of the links of the first side wall define respective outermost gaps with respect to the leading end and trailing end, respectively, outermost ones of the links of the second side wall define respective second outermost gaps with respect to the leading end and trailing end.

11. The intervertebral fusion cage of claim 10, wherein the first outermost gaps and the second outermost gaps are substantially identical to each other in size and shape.

12. The intervertebral fusion cage of claim 10, wherein the gaps between adjacent ones of the links are intermediate gaps, and the intermediate gaps and the first and second outermost gaps decrease in size when the cage expands along the lateral direction to the expanded lateral position.

13. The intervertebral fusion cage of claim 1, further comprising:
a core configured for insertion between the upper vertebral contacting surface and the lower vertebral contacting surface, the core having a height along the transverse direction sufficient such that insertion of the core between the upper vertebral engagement body and the lower vertebral engagement body causes the intervertebral fusion cage to expand along the transverse direction.

14. The intervertebral fusion cage of claim 13, wherein the core defines first and second arms that are flexible so as to remain aligned with the first and second side walls, respectively, of the fusion cage when the fusion cage expands from the first lateral position to the expanded lateral position.

15. The intervertebral fusion cage of claim 13, further comprising a post that joins the upper vertebral engagement body to the lower vertebral engagement body at the leading end of the fusion cage, and an actuation body that is coupled to the post and configured to apply a compressive force to the leading end toward the trailing end that causes the fusion cage to expand from the first lateral position to the expanded lateral position.

16. The intervertebral fusion cage of claim 13, comprising frangible ribs attached to the upper and lower vertebral engagement bodies when the fusion cage is in the first transverse position, wherein insertion of the core between the upper vertebral contacting surface and the lower vertebral contacting surface causes the frangible ribs to rupture, thereby allowing the upper and lower vertebral engagement bodies to move away from each other along the transverse direction until the cage is in the expanded transverse position.

17. The intervertebral fusion cage of claim 13, further comprising first and second channels that extend at least into the cage body, wherein the core comprises first and second core arms that are insertable into the first and second channels, respectively, so as to expand the intervertebral fusion cage from the first transverse position to the expanded transverse position.

18. The intervertebral fusion cage of claim 17, wherein each of the side walls defines a respective cage interlocking member, each of the arms of the core defines a respective core interlocking member so as to couple the upper and lower vertebral engagement bodies to the core with respect to movement away from each other along the transverse direction.

19. The intervertebral fusion cage of claim 1, further comprising an actuation member that is coupled to the leading end of the fusion cage, the actuation member configured to apply a compressive force to the leading end toward the trailing end that causes the fusion cage to expand from the first lateral position to the expanded lateral position.

20. An intervertebral fusion cage comprising:
a cage body that defines a leading end with respect to a direction of insertion into an intervertebral space, a trailing end opposite the leading end along a longitudinal direction, an upper vertebral engagement body that defines an upper vertebral contacting surface, a lower vertebral engagement body that defines a lower vertebral contacting surface spaced from the upper vertebral contacting surface along a transverse direction that is substantially perpendicular with respect to the longitudinal direction, and first and second side walls that extend between the leading end and the trailing end, the first and second side walls opposite each other along a lateral direction that is substantially perpendicular to each of the longitudinal direction and the transverse direction,
a core having an insertion height prior to insertion into the cage body, the core configured for insertion into the cage body at the insertion height between the upper vertebral contacting surface and the lower vertebral contacting surface, the insertion height of the core being sufficient along the transverse direction such that insertion of the core between the upper vertebral engagement body and the lower vertebral engagement body at the insertion height causes the core to bear against the upper and lower vertebral engagement bodies, thereby urging the intervertebral fusion cage to expand along the transverse direction,
wherein the cage body is expandable from a first lateral position whereby the side walls extend substantially parallel to each other to an expanded lateral position whereby the first and second side walls move away from each other to a position that defines a substantially circular shape.

21. The intervertebral fusion cage of claim 20, wherein the cage body is responsive to a compressive force applied to the leading and trailing ends so as to move from the first lateral position to the expanded lateral position.

22. The intervertebral fusion cage of claim 20, wherein the lower and upper vertebral engagement bodies are separated from each other by a gap of the cage body that extends from the leading end to the trailing end, such that insertion of the core between the upper vertebral engagement body and the lower vertebral engagement body causes the core to urge the lower and upper vertebral engagement bodies away from each other in their respective entireties, thereby expanding the intervertebral fusion cage along the transverse direction.

23. The intervertebral fusion cage of claim 20, further comprising first and second channels that extend at least into the cage body, wherein the core comprises first and second core arms that are insertable into the first and second channels, respectively, so as to expand the intervertebral fusion cage along the transverse direction.

\* \* \* \* \*